US010927075B2

(12) United States Patent
Mills et al.

(10) Patent No.: US 10,927,075 B2
(45) Date of Patent: Feb. 23, 2021

(54) COMPOSITIONS AND METHODS RELATING TO THE TREATMENT OF CANCER, AUTOIMMUNE DISEASE, AND NEURODEGENERATIVE DISEASE

(71) Applicant: THE JACKSON LABORATORY, Bar Harbor, ME (US)

(72) Inventors: Kevin David Mills, Bar Harbor, ME (US); Muneer Gulamhusein Hasham, Ellsworth, ME (US)

(73) Assignee: THE JACKSON LABORATORY, Bar Harbor, ME (US)

( * ) Notice: Subject to any disclaimer, the term of this patent is extended or adjusted under 35 U.S.C. 154(b) by 0 days.

(21) Appl. No.: 15/534,546

(22) PCT Filed: Dec. 14, 2015

(86) PCT No.: PCT/US2015/065487
§ 371 (c)(1),
(2) Date: Jun. 9, 2017

(87) PCT Pub. No.: WO2016/094897
PCT Pub. Date: Jun. 16, 2016

(65) Prior Publication Data
US 2017/0362172 A1 Dec. 21, 2017

Related U.S. Application Data

(60) Provisional application No. 62/091,026, filed on Dec. 12, 2014.

(51) Int. Cl.
*C07C 311/47* (2006.01)
*C07C 335/20* (2006.01)
*C07D 205/04* (2006.01)
*C07D 295/26* (2006.01)
*C07F 9/38* (2006.01)
*C07C 307/10* (2006.01)
*C07C 335/16* (2006.01)
*C07C 311/39* (2006.01)
*C07C 311/08* (2006.01)
*C07F 9/12* (2006.01)
*C07C 335/22* (2006.01)

(52) U.S. Cl.
CPC .......... *C07C 335/20* (2013.01); *C07C 307/10* (2013.01); *C07C 311/08* (2013.01); *C07C 311/39* (2013.01); *C07C 311/47* (2013.01); *C07C 335/16* (2013.01); *C07C 335/22* (2013.01); *C07D 205/04* (2013.01); *C07D 295/26* (2013.01); *C07F 9/12* (2013.01); *C07F 9/3873* (2013.01)

(58) Field of Classification Search
CPC ... C07C 311/47; C07C 335/20; C07D 205/04; C07D 295/26; C07F 9/38
See application file for complete search history.

(56) References Cited

U.S. PATENT DOCUMENTS

| 3,070,443 | A | * | 12/1962 | Thomanek | ............ | G03F 7/0045 |
| | | | | | | 430/270.1 |
| 3,828,060 | A | | 8/1974 | Lyness et al. | | |
| 5,359,131 | A | * | 10/1994 | Cardin | .................. | C07C 309/42 |
| | | | | | | 562/48 |
| 5,569,786 | A | | 10/1996 | Pettit et al. | | |
| 6,048,903 | A | | 4/2000 | Toppo et al. | | |
| 6,361,815 | B1 | | 3/2002 | Zheng et al. | | |
| 6,552,213 | B1 | | 4/2003 | Deshpande et al. | | |
| 6,844,471 | B2 | | 1/2005 | Deshpande et al. | | |
| 7,803,790 | B2 | * | 9/2010 | Chong | ............... | A61K 31/4709 |
| | | | | | | 514/183 |
| 2002/0058708 | A1 | * | 5/2002 | Inman | .................. | A61K 31/192 |
| | | | | | | 514/568 |
| 2004/0015020 | A1 | | 1/2004 | Deshpande et al. | | |
| 2004/0147788 | A1 | | 7/2004 | Savouret et al. | | |
| 2004/0152629 | A1 | | 8/2004 | Hadfield et al. | | |
| 2009/0182003 | A1 | | 7/2009 | Sinclair et al. | | |
| 2013/0184342 | A1 | | 7/2013 | Mills et al. | | |

FOREIGN PATENT DOCUMENTS

| CN | 102786414 | * | 11/2012 |
| EP | 0331983 B1 | | 12/1994 |
| WO | 2003/039557 A1 | | 5/2003 |
| WO | 2004/021987 A2 | | 3/2004 |
| WO | 2014177593 | * | 11/2014 |

OTHER PUBLICATIONS

Eckermann et al., Stilbenecarboxylate biosynthesis: a New Function in the Family of Chalcone Synthase-Related Proteins, Phytochemistry, vol. 62, No. 3, pp. 271-286 (Year: 2003).*
Holt et al., Fluorescent Whitening Agents Part III: Photodecomposition of Disodium 4,4'-Diacetannidostilbene-2,2'-Disulfonate, Textile Research Journal, vol. 44, No. 3, pp. 181-183 (Year: 1974).*
Oda et al., Intramolecular Quenching of the Photofading of Some Dyes, Journal of the Society of Dyers and Colourists, vol. 101, No. 5-6, pp. 177-179 (Year: 1985).*
STN printout for Reg. No. 1030827-49-6 (Year: 2008).*
CAPLUS printout for Tang et al., Electron-Impact Mass-Spectroscopic (EIMS) Study of Aromatic Sulfonic Acids by a New Derivatization Method, Huaxue Tongbao, vol. 1, pp. 41-45 (Year: 1991).*
Badger et al., Journal of Pharmacology and Experiemtnal Therapeutics, 291(3):1380-1386 (1999). "Idoxifene, a novel selective estrogen receptor modulator, is effective in a rat model of adjuvant-induced arthritis."
Budgaard Design of Prodrugs Chapter 1, (1985).

(Continued)

*Primary Examiner* — Brenda L Coleman
(74) *Attorney, Agent, or Firm* — Nixon Peabody LLP; David S. Resnick; Nicole D. Kling

(57) ABSTRACT

Described herein are methods and compositions relating to the treatment of e.g., cancer, autoimmune disease, immune deficiency, and/or neurodegenerative disease. In some embodiments, the methods of treatment relate to administering a compound as described herein. In some embodiments, the subject treated according to the methods described herein is a subject determined to have an increased level of DNA damage.

14 Claims, 23 Drawing Sheets

(56) References Cited

OTHER PUBLICATIONS

Cancercompas (https://cancercompass.com/leukemia-information/side-effects.htm) 2016.
Cecil Textbook of Medicine 20th Ed., vol. 1 (1996).
Dorwald, Side Reactions in Organic Synthesis: A Guide to Successful Synthesis Design (2005).
Eddarir et al., "Fluorinated resveratrol and pterostilbene." Tetrahedron Lett., 42:9127-9130 (2001).
Feldhahn et al., "Activation-induced cytidine deaminase acts as a mutator in BCR-ABL1-transformed acute lymphoblastic leukemia cells." The Journal of Experimental Medicine 204(5):1157-1166 (2007).
Greeve et al., "Expression of activation-induced cytidine deaminase in human B-cell non-Hodgkin lymphomas", Blood, 101:9(1): 3574-3580 (2003).
Gura et al., Science 278 (1997).
Hasham et al., Nature Immunology, 11(9):820-826 (2010). "Widespread genomic breaks generated by activation-Induced cytidine deaminase are prevented by homologous recombination."
Horvat et al., "Tumour cell proliferation is abolished by inhibitors of Na+ H+ and HCO3—Cl— exchange." European Journal of Cancer 29(1):132-137 (1993).
Hwang et al., Molecular and Cellular Biochemistry, 327(1-2):135-144 (2009). "Reduction of anion exchange 2 expression induces apoptosis of human hepatocellular biochemistry."
Ishida et al., Nucleic Acids Research, 37(10):3367-3376 (2009). "DIDS, a chemical compound that inhibits RAD51—mediated homologous pairing and strand exchange."
Jiang et al., "Suppression of cell proliferation with induction of p21 by Cl(-) channel blockers in human leukemic cells", European Journal of Pharmacology 488(1-3):27-34 (2004).
Johnson et al., British J. of Cancer 1424-1431 (2001).
Kim et al., International Immunopharmacology, 8(12):1695-1702 (2008). "Piceatannol, a stilbene present in grapes, attenuates dextran sulfate sodium-induced colitis."
Klein, "The consequences of Rad51 overexpression for normal and tumor cells", DNA Repair 7(5):686-693 (2008).
Lao, et al., Chinese Journal of Biologicals, 22(7):654-658 (2009). "Autophagy Pathway of Raji Cell Death Induced by Resveratrol."
Leuenberger et al., Modern Pathology, 23(2):177-186 (2010). "AID protein expression in chronic lymphocytic leukemia/small lymphocytic lymphoma is associated with poor prognosis and complex genetic alterations."
Li et al., "Crystal Struture of an Archaeal Rad51 Homologue in Complex with a Metatungstate Inhibitor", Biochemistry, 48(29):6805-6810 (2009).
Li et al., "British Journal of Pharmacology, 160(6):1352-1361 (2010). "2, 3", 4, 4", 5", -Pentamethoxy-trans-stilbene, a resveratrol derivative, inhibits colitis-associated colorectal carcinogenesis in mice."
Liu et al., Molecular and Cellular Biochemistry, 308(1-2):117-125 (2007). "Anion exchanger inhibitor DIDS induces human poorly-differentiated malignant hepatocellular carcinoma HA22T cell apoptosis."
Lockwood "www.rn.org, Leukemia: AML, CML, ALL and CLL" (2015).
Medina-Gundrum et al., Investigational New Drugs 23:3-9 (2005).
Palacios, F. et al., "High expression of AID and active class switch recombination might account for a more aggressive disease in unmutated CLL patients: link with an activated microenvironment in CLL disease." Blood 115(22): 4488-4496 (2010).
Roberti et al., "Synthesis and biological evaluation of resveratrol and analogues as apoptosis-inducing agents." J. Med. Chem. 46(16):3546-54 (2003).
Roman et al., British Journal of Haematology, 117(842-852 (2002). Analysis of reseratol-induced apoposis of human B-cell chronic leukaemia.
Silverman "Prodrugs and Drugs Delivery System," in The Organic Chemistry of Drug Design and Drug Action352-401 (1992).
Solladie et al., "A re-investigation of resveratrol synthesis by Perkins reaction. Application to the synthesis of aryl cinnamic acids." Tetrahedron 59:3315-3321 (2003).
Thomas et al., "Manganese triacetate oxidative lactonisation of electron-rich stilbenes possessing catechol and resorcinol substitution (resveratrol analogues)." Tetrahedron Lett. 43:3151-3155 (2002).
Wang et al., Chinese Pharmacological Bulletin, 26(3):346-352 (2010). "The study of resveratrol on acute myeloblastic leukemia by modulating SATA3."
Wieder et al., "Piceatannol, a hydroxylated analog of the chemopreventitive agent resveratrol, is a potent inducer of apoptosis in the lymphoma cell line BJAB and in primary, leukemic lymphoblasts", Leukemia 15:1735-1742 (2001).
Wiese et al., "Promotion of homologous recombination and genomic stability by RAD51AP1 via RAD51 recombinase enhancement", Molecular Cell 28(3):482-490 (2007).
Yu et al., "Convenient preparation of trans-arylalkenes via palladium(II)-catalyzed isomerization of cis-arylalkenes. Meier et al., Bis-(stilbenyl)squaraines-Novel Pigments with Extended Conjugation." Tetrahedron Lett., 37(8):1191-1194 (1996). J. Org. Chem. 67(13):4627-29 (2002).
Froeyen et al., "RNA as a target for drug design, the example of Tat-TAR interaction." Current Topics in Medicinal chemistry 2(10):1123-1145 (2002).
Gunosewoyo et al. ,"Molecular probes for P2X7 receptor studies." Current Medicinal Chemistry 14(14):1505-1523 (2007).
Soo et al. "Visible light-induced hole injection into rectifying molecular wires anchored on Co3O4 and SiO2 nanoparticles." Journal of the American Chemical Society 134(41):17104-17116 (2012).
Thompson et al., "Inhibitors of the glutamate vesicular transporter (VGLUT)." Current Medicinal Chemistry 12 (18):2041-2056 (2005).
Wrobel et al. "Synthesis of (bis) sulfonic acid,(bis) benzamides as follicle-stimulating hormone (FSH) antagonists." Bioorganic & Medicinal Chemistry 10(3):639-656 (2002).
Cooper GM. The Cell: A Molecular Approach. 2nd Edition, Sunderland (MA): Sinauer Associates, Chapter 5, Replication, Maintenance, and Rearrangements of Genomic DNA. Available from: https://www.ncbi.nlm.nih.gov/books/NBK9900/ (2000).
Cooper GM. The Cell: A Molecular Approach. 2nd edition. Sunderland (MA): Sinauer Associates. Glossary. Available from: https://www.ncbi.nlm.nih.gov/books/NBK9926/ (2000).
Noell. "Studies on visual cell viability and differentiation." Annals of the New York Academy of Sciences 74(2): 337-361 (1958).
Riss et al. "Cell viability assays." In Assay Guidance Manual [Internet]. Eli Lilly & Company and the National Center for Advancing Translational Sciences: 1-25 (2016).

* cited by examiner

Fig. 4

| Analyte | Group | Route | Dose Level | $C_{max}$ (ng/mL) | SE $C_{max}$ (ng/mL) | $T_{max}$ (hr) | $AUC_{all}$ (hr*ng/mL) | SE $AUC_{all}$ (hr*ng/mL) | $AUC_{INF}$ (hr*ng/mL) | Half-life (hr) | F (Fraction) |
|---|---|---|---|---|---|---|---|---|---|---|---|
| C-1523 | 2 | PO | 2 | 7.01 | 0.968 | 1.00 | 22.8 | 4.52 | 24.2 | 1.66ᵃ | 0.0129 |
| DIDS | 4 | PO | 2 | 36.1 | 10.3 | 4.00 | 150 | 38.0 | NC | NC | 0.00521 |

| Group | Route | Dose (mg/kg) | Animal ID | $C_{max}$ (ng/mL) | $T_{max}$ (hr) | $AUC_{all}$ (hr*ng/mL) | $AUC_{inf}$ (hr*ng/mL) | Half-life (hr) | F |
|---|---|---|---|---|---|---|---|---|---|
| 2 | PO | 2 | 2M001 | 5.79 | 2 | 39.6 | NC | NC | 0.0203 |
| | | | 2M002 | 5.70 | 2 | 17.1 | NC | NC | 0.00898 |
| | | | 2M003 | 3.24 | 2 | 13.0 | NC | NC | 0.00667 |
| | | | N | 3 | 3 | 3 | 0 | 0 | 3 |
| | | | Mean | 4.90 | 2.0 | 23.2 | NC | NC | 0.0119 |
| | | | SD | 1.42 | 0.0 | 14.3 | NC | NC | 0.0073 |

Fig. 5

| Analyte | Group | Route | Dose Level | $C_0$ (ng/mL) | $AUC_{all}$ (hr*ng/mL) | SE $AUC_{all}$ (hr*ng/mL) | $AUC_{INF}$ (hr*ng/mL) | CL (mL/min/kg) | Vss (L/kg) | Half-life (hr) |
|---|---|---|---|---|---|---|---|---|---|---|
| C-1523 | 1 | IV | 1 | 999 | 881 | 110 | 876 | 19.0 | 0.733 | 0.463 |
| DIDS | 3 | IV | 1 | 2830 | 14400 | 1260 | 17500 | 0.955 | 0.739 | 10.3 |

| Group | Route | Dose (mg/kg) | Animal ID | $C_0$ (ng/mL) | $AUC_{all}$ (hr*ng/mL) | $AUC_{INF}$ (hr*ng/mL) | CL (mL/min/kg) | Vss (L/kg) | Half-life (hr) |
|---|---|---|---|---|---|---|---|---|---|
| 1 | IV | 1 | 1M001 | 5530 | 760 | 753 | 22.1 | 0.462 | 1.80 |
| | | | 1M002 | 8120 | 1050 | 1040 | 16.0 | 0.258 | 1.04 |
| | | | 1M003 | 8040 | 1120 | 1120 | 14.9 | 0.172 | 0.69 |
| | | | N | 3 | 3 | 3 | 3 | 3 | 3 |
| | | | Mean | 7230 | 977 | 971 | 17.7 | 0.293 | 1.18 |
| | | | SD | 1420 | 191 | 193 | 3.9 | 0.144 | 0.72 |

| Group | Test Article | Route | Dose (mg/kg) | Time (h) | Plasma Concentration (ng/mL) by Subject | | | | | |
|---|---|---|---|---|---|---|---|---|---|---|
| | | | | | 1M001 | 1M002 | 1M003 | Mean | SD | N |
| 1 | C-15231a | IV | 2 | 0.083 | 9570 | 9050 | 5410 | 8010 | 2270 | 3 |
| | | | | 0.25 | 2500 | 3960 | 1750 | 2740 | 1120 | 3 |
| | | | | 0.5 | 859 | 1830 | 680 | 1120 | 620 | 3 |
| | | | | 1 | 187 | 254 | 195 | 212 | 37 | 3 |
| | | | | 2 | 30.2 | 144 | 77.3 | 83.8 | 57.2 | 3 |
| | | | | 4 | 15.3 | 62.6 | 22.9 | 33.6 | 25.4 | 3 |
| | | | | 8 | BLQ | 6.67 | BLQ | 6.67 | n=1 | 1 |
| | | | | 24 | BLQ | BLQ | BLQ | BLQ | — | 0 |

| Group | Test Article | Route | Dose (mg/kg) | Time (h) | Plasma Concentration (ng/mL) by Subject | | | | | |
|---|---|---|---|---|---|---|---|---|---|---|
| | | | | | 2M001 | 2M002 | 2M003 | Mean | SD | N |
| 2 | C-15231a | IV | 10 | 0.083 | 47700 | 53500 | 44700 | 48600 | 5000 | 3 |
| | | | | 0.25 | 16500 | 13100 | 8400 | 12700 | 3100 | 3 |
| | | | | 0.5 | 3080 | 7610 | 3010 | 4840 | 2630 | 3 |
| | | | | 1 | 1290 | 2240 | 1370 | 1630 | 530 | 3 |
| | | | | 2 | 336 | 326 | 644 | 435 | 180 | 3 |
| | | | | 4 | 19.1 | 147 | 101 | 89.0 | 64.8 | 3 |
| | | | | 8 | 47.0 | 44.2 | 58.4 | 49.9 | 7.5 | 3 |
| | | | | 24 | 13.2 | 8.66 | 15.7 | 12.5 | 3.6 | 3 |

| Group | Test Article | Route | Dose (mg/kg) | Time (h) | Plasma Concentration (ng/mL) by Subject | | | | | |
|---|---|---|---|---|---|---|---|---|---|---|
| | | | | | 3M001 | 3M002 | 3M003 | Mean | SD | N |
| 3 | C-15231a | IV | 20 | 0.083 | 78300 | 69100 | 12100 | 53200 | 35900 | 3 |
| | | | | 0.25 | 20900 | 19800 | 20200 | 20300 | 600 | 3 |
| | | | | 0.5 | 10500 | 6220 | 12000 | 9570 | 3000 | 3 |
| | | | | 1 | 2560 | 3930 | 7120 | 4600 | 2330 | 3 |
| | | | | 2 | 2330 | 1310 | 4310 | 2720 | 1510 | 3 |
| | | | | 4 | 1060 | 454 | 1680 | 1060 | 620 | 3 |
| | | | | 8 | 199 | 212 | 400 | 271 | 120 | 3 |
| | | | | 24 | 87.8 | 48.1 | 152 | 95.9 | 53.4 | 3 |

Fig. 6

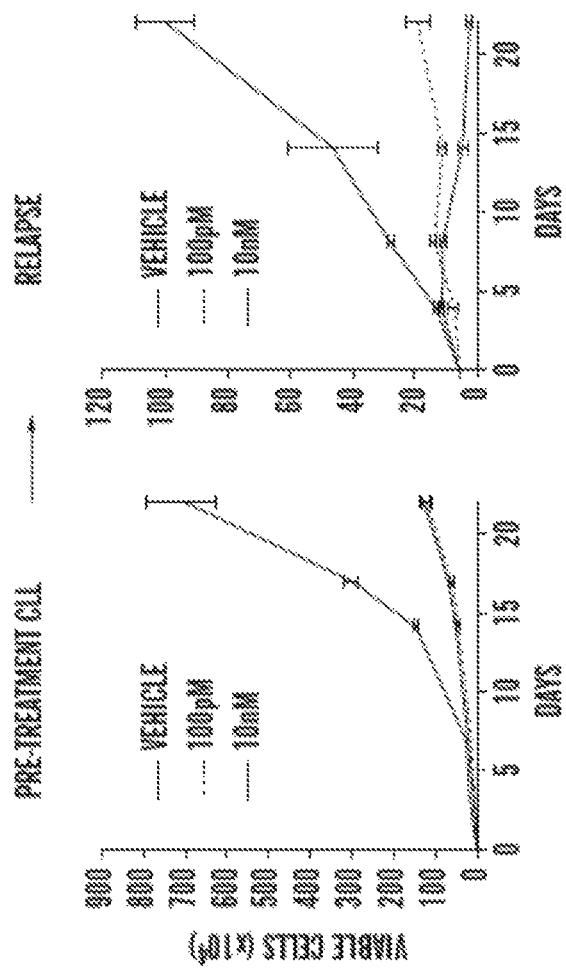
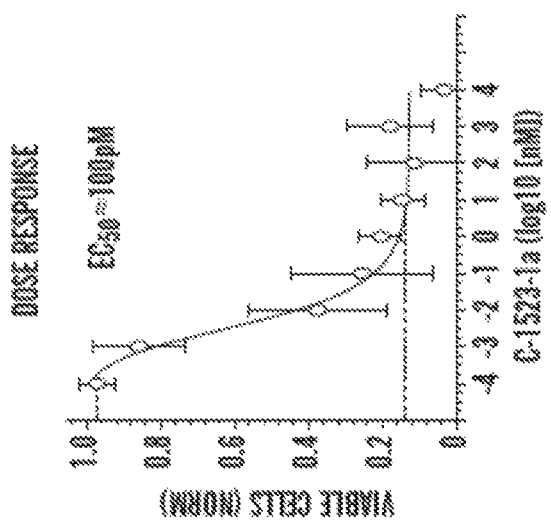
FIG. 8

C-1523-1a compared to Ibrutinib in Targeting B Lymphoid Subsets

COMPOSITIONS AND METHODS RELATING TO THE TREATMENT OF CANCER, AUTOIMMUNE DISEASE, AND NEURODEGENERATIVE DISEASE

CROSS-REFERENCE TO RELATED APPLICATIONS

This application is a 35 U.S.C. § 371 National Phase Entry Application of International Application No. PCT/US15/065487 filed Dec. 14, 2015, which designates the U.S. and claims benefit under 35 U.S.C. § 119(e) of U.S. Provisional Application No. 62/091,026 filed Dec. 12, 2014, the contents of which are incorporated herein by reference in their entireties.

GOVERNMENT SUPPORT

This invention was made with government support under Grant No. R41CA183197 awarded by the National Cancer Institute. The U.S. government has certain rights in the invention.

TECHNICAL FIELD

The technology described herein relates to the treatment of, e.g., cancer, autoimmune disorders, and/or neurodegenerative diseases by inhibiting DNA repair mechanisms.

BACKGROUND

In 2010, there were an estimated 137,000 new cases of leukemia, lymphoma and multiple myeloma, and more than 54,000 deaths from these cancers in the United States alone. The current standard of care in leukemia/lymphoma treatment often involves intensive, long-term chemotherapy, which can be physically taxing for the patient. Common side effects of conventional chemotherapy include immune system disruption, myelosuppression, bone marrow destruction, nausea, fatigue, liver toxicity, weight loss, hair loss, long-term cognitive impairment and therapy-related secondary tumors. A major problem with standard chemotherapy is the damage done to otherwise healthy cells and tissues in the cancer patient. Current treatment often fails to achieve long-term remission, and patients who do survive routinely experience long-lasting chemotherapy-related health concerns that prevent them from ever being truly well. Selective targeting of the therapy specifically to the cancer cells can ameliorate most of these devastating side effects. Unfortunately, with few exceptions, selective targeting is technically difficult or impossible. Additional or alternative approaches to selectively target cancer cells, while minimizing off-target side effects, are therefore desperately needed.

SUMMARY

Described herein are compounds that inhibit DNA repair mechanisms, e.g. double-strand break repair, and methods of using such compounds, e.g. to treat cancer, autoimmune diseases, and/or neurodegenerative diseases. This inhibition of DNA repair makes such compounds deleterious only to cells experiencing elevated levels of DNA damage, a characteristic of cells which contribute to and/or cause the pathology of such diseases. Accordingly, provided herein are compounds and methods relating to selectively inhibiting and/or killing cells with increased levels of DNA damage and/or increased levels and/or activity of DNA editing enzymes, e.g. for the treatment of cancer.

The methods and compounds described herein relate to the killing of cells with elevated levels of DNA damage, including, e.g. cells with increased levels and/or activity of a DNA editing enzyme, cells with abnormal metabolism, and/or cells treated with a DNA damaging agent (e.g. radiation or chemotherapy).

In one aspect, described herein is a compound of Formula I:

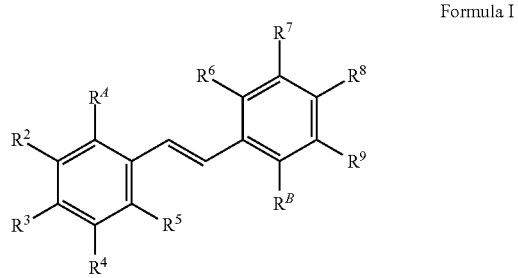

Formula I wherein $R^A$ and $R^B$ are $SO_2N(R^{22})_2$, or $R^A$ and $R^B$ is $SO_3R^{23}$ and the other is hydrogen or $SO_3R^{23}$, or one of $R^A$ and $R^B$ is $SO_3^-Y^+$ and the other is hydrogen, or one of $R^A$ is $R^B$ is $CO_2^-Y^+$ and the other is hydrogen or $CO_2^-Y^+$, or one of $R^A$ and $R^B$ is $PO_3^-(Y^+)_2$ and the other is hydrogen or $PO_3^-(Y^+)_2$; $R^2$, $R^3$, $R^4$, $R^5$, $R^6$, $R^7$, $R^8$ and $R^9$ are independently hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{12})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl, provided that $R^3$ and $R^8$ are not the same; $R^{21}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl; $R^{22}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl; $R^{23}$ is independently for each occurrence optionally substituted linear or branched $C_1$-$C_{10}$ alkyl; $Y^+$ is for each occurrence a cation; and pharmaceutically acceptable salts thereof.

In some embodiments, $R^3$ and $R^8$ are selected independently from the group consisting of hydrogen, hetercyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$, wherein $R^{21}$ is H or $C_1$-$C_4$alkyl and $R^{22}$ can be H or $C_1$-$C_{10}$ alkyl.

In some embodiments, $R^3$ and $R^8$ are selected independently from the group consisting of hydrogen, OH, $OCH_3$, N=C=S, $NH_2$, $NHCH_3$, $NO_2$, NH-octadecane, NHC(O)$CH_3$, NHC(O)CH($CH_3$)$_2$, NHC(O)$CH_2OCH_3$, $NHSO_2CH_3$, $NHSO_2$-cyclopropane, $NHSO_2CH(CH_3)_2$, $NHSO_2N(CH_3)_2$, NHC(S)NHCH$_3$, NHC(S)NHCH(CH$_3$)$_2$, NHC(S)NH-cyclopropane, NHC(O)NHCH$_3$, NHC(O)NHCH(CH$_3$)$_2$, benzoxazolyl, and NHC(O)NH-cyclopropane.

In some embodiments, one of R$^3$ and R$^8$ is NHC(O)CH$_3$ and the other is NHC(O)CH$_3$ or NHC(S)NHCH(CH$_3$)$_2$. In some embodiments, R$^3$ and R$^8$ are different. In some embodiments, at least one of R$_2$, R$_4$, R$_5$, R$_6$, R$_7$, and R$_9$ is hydrogen. In some embodiments, R$_2$, R$_4$, R$_5$, R$_6$, R$_7$, and R$_9$ all are hydrogen.

In some embodiments, R$^{22}$ is selected independently for each occurrence from the group consisting of hydrogen, methyl, ethyl, propyl, isopropyl, butyl, isobutyl, pentyl, t-butyl, and cyclopropyl; or the two R$^{22}$ together with the nitrogen they are attached to form an optionally substituted 3-8 membered heterocyclyl. In some embodiments, R$^{23}$ is independently for each occurrence methyl, ethyl, propyl, isopropyl, butyl, isobutyl, pentyl, t-butyl, or cyclopropyl. In some embodiments, Y$^+$ is selected independently for each occurrence from the group consisting of sodium, potassium, aluminum, calcium, lithium, magnesium, barium, zinc, ammonium, aminium, and any combinations thereof.

In some embodiments, R$^A$ is SO$_3$R$^{23}$; R$^B$ is hydrogen or SO$_3$R$^{23}$; and each R$^{23}$ is independently isopropyl or t-butyl. In some embodiments, R$^A$ is SO$_3$R$^{23}$; R$^B$ is hydrogen or SO$_3$R$^{23}$; and R$_2$, R$_4$, R$_5$, R$_6$, R$_7$, and R$_9$ are hydrogen. In some embodiments, R$^A$ is SO$_3$R$^{23}$; R$^B$ is hydrogen or SO$_3$R$^{23}$; each R$^{23}$ is independently isopropyl or t-butyl; and R$_2$, R$_4$, R$_5$, R$_6$, R$_7$, and R$_9$ are hydrogen. In some embodiments, one of R$^A$ and R$^B$ is SO$_3^-$Y$^+$ and the other is hydrogen; and one of R$^3$ and R$^8$ is NHC(O)CH$_3$ and the other is NHC(S)NHCH(CH$_3$)$_2$. In some embodiments, one of R$^A$ and R$^B$ is SO$_3^-$Y$^+$ and the other is hydrogen; and R$_2$, R$_4$, R$_5$, R$_6$, R$_7$, and R$_9$ are hydrogen. In some embodiments, one of R$^A$ and R$^B$ is SO$_3^-$Y$^+$ and the other is hydrogen; one of R$^3$ and R$^8$ is NHC(O)CH$_3$ and the other is NHC(S)NHCH(CH$_3$)$_2$; and R$_2$, R$_4$, R$_5$, R$_6$, R$_7$, and R$_9$ are hydrogen. In some embodiments, one of R$^A$ and R$^B$ is CO$_2^-$Y$^+$ and the other is hydrogen or CO$_2^-$Y$^+$; and one of R$^3$ and R$^8$ is NHC(O)CH$_3$ and the other is NHC(S)NHCH(CH$_3$)$_2$. In some embodiments, one of R$^A$ and R$^B$ is CO$_2^-$Y$^+$ and the other is hydrogen or CO$_2^-$Y$^+$; and R$_2$, R$_4$, R$_5$, R$_6$, R$_7$, and R$_9$ are hydrogen. In some embodiments, one of R$^A$ and R$^B$ is CO$_2^-$Y$^+$ and the other is hydrogen or CO$_2^-$Y$^+$; one of R$^3$ and R$^8$ is NHC(O)CH$_3$ and the other is NHC(S)NHCH(CH$_3$)$_2$; and R$_2$, R$_4$, R$_5$, R$_6$, R$_7$, and R$_9$ are hydrogen. In some embodiments, one of R$^A$ and R$^B$ is PO$_3^-$Y$^+$ and the other is hydrogen or PO$_3^-$Y$^+$; and one of R$^3$ and R$^8$ is NHC(O)CH$_3$ and the other is NHC(S)NHCH(CH$_3$)$_2$. In some embodiments, one of R$^A$ and R$^B$ is PO$_3^-$Y$^+$ and the other is hydrogen or PO$_3^-$Y$^+$; and R$_2$, R$_4$, R$_5$, R$_6$, R$_7$, and R$_9$ are hydrogen. In some embodiments, one of R$^A$ and R$^B$ is PO$_3^-$Y$^+$ and the other is hydrogen or PO$_3^-$Y$^+$; one of R$^3$ and R$^8$ is NHC(O)CH$_3$ and the other is NHC(S)NHCH(CH$_3$)$_2$; and R$_2$, R$_4$, R$_5$, R$_6$, R$_7$, and R$_9$ are hydrogen.

In some embodiments, the compound is selected from the group consisting of

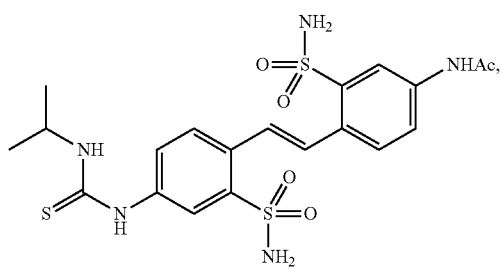

-continued

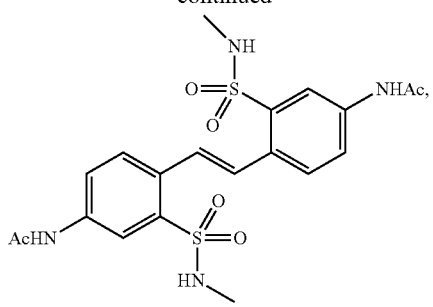

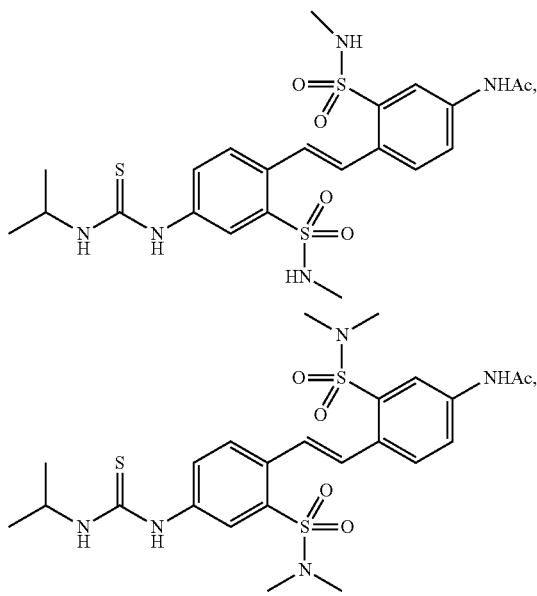

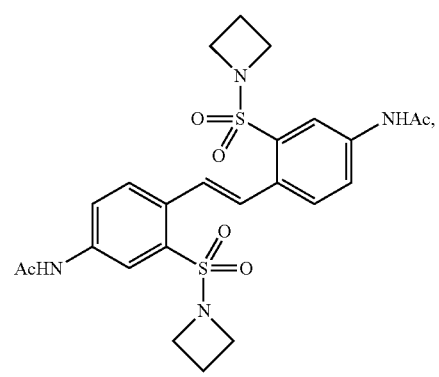

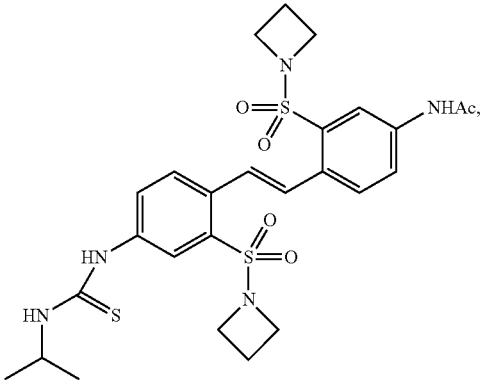

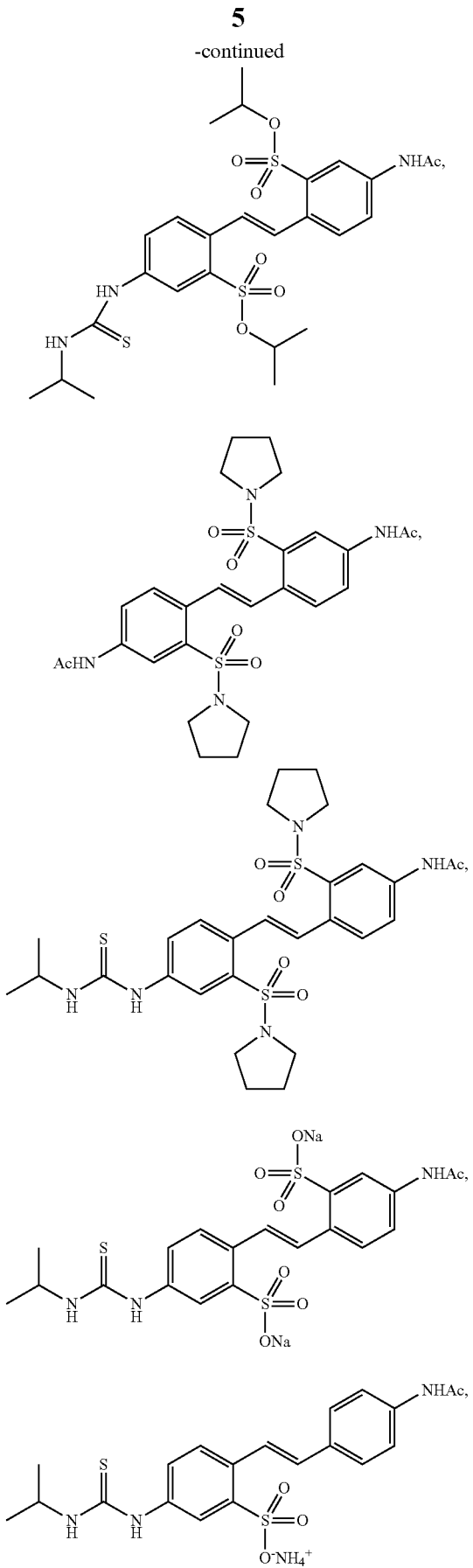

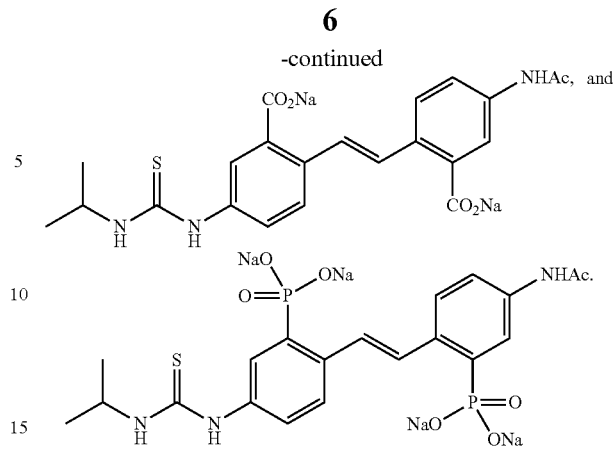

In one aspect, described herein is a method of treating cancer, autoimmune disease, immune deficiency, or neurodegenerative disease, the method comprising administering a therapeutically effective dose of a composition as described herein to a subject in need of treatment for cancer, autoimmune disease, immune deficiency, or neurodegenerative disease.

In some embodiments, the subject is determined to have an increased level of DNA damage occurring in one or more cell types relative to a reference level. In some embodiments, the subject is determined to have an increased level of DNA damage occurring in a cell selected from the group consisting of: a cancer cell; an immune cell; an autoimmune cell; or a nervous system cell. In some embodiments, the DNA damage is selected from the group consisting of: single-stranded DNA breaks, double-strand DNA breaks, and DNA mutations.

In some embodiments, a subject is determined to have an increased level of DNA damage if the subject is determined to have an increased level and/or activity of a DNA damage process or DNA editing enzyme. In some embodiments, the DNA editing enzyme is selected from the group consisting of: activation induced cytidine deaminase (AID or AICDA), APOBEC2, APOBEC3A, APOBEC3C, APOBEC3D, APOBEC3F, APOBEC3G, APOBEC3H, APOBEC4, a Type 1 Topoisomerase, a Type 2 Topoisomerase, Recombination Activating Gene 1 (RAG1), and Recombination Activating Gene 2 (RAG2).

In some embodiments, a subject is determined to have an increased level of DNA damage if the subject has been exposed to a DNA damaging agent selected from the group consisting of: a viral infection with a DNA integrating virus; exposure to a DNA damaging chemical; exposure to a chemotherapeutic agent; and exposure to ionizing or ultraviolet radiation.

In some embodiments, the DNA damage is a double strand break. In some embodiments, the DNA damage enzyme is activation-induced cytidine deaminase (AID). In some embodiments, an increased level of AID is a detectable level of AID. In some embodiments, an increased level of AID is a level of AID which is statistically significantly higher than the level of AID expressed in unactivated B cells or a normal non-immune cell from a healthy subject. In some embodiments, the level of AID is the level in a blood cell or B cell.

In some embodiments, the cancer is selected from the group consisting of: lymphoma, leukemia, and a plasma cell neoplasm. In some embodiments, the lymphoma is selected from the group consisting of: Non-Hodgkin's lymphoma; Burkitt's lymphoma, small lymphocytic lymphoma; lymphoplasmacytic lymphoma; MALT lymphoma; follicular lymphoma; diffuse large B-cell lymphoma; and T-cell lymphoma. In some embodiments, the leukemia is selected from the group consisting of: acute lymphoblastic leukemia (ALL), Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL). In some embodiments, the plasma cell neoplasm is selected from the group consisting of: multiple myeloma; plasma cell myeloma; plasma cell leukemia; and plasmacytoma. In some embodiments, the subject has a cancer selected from the group consisting of: epithelial cell cancer; colon cancer, liver cancer, gastric cancer; intestinal cancer; esophageal cancer; breast cancer; ovarian cancer; head and neck cancer; lung cancer; and thyroid cancer.

In some embodiments, the autoimmune disease is selected from the group consisting of: lupus erythematosus: Wiskott-Aldrich syndrome; autoimmune lymphoproliferative syndrome; myasthenia gravis; rheumatoid arthritis (RA); lupus nephritis; multiple sclerosis; systemic lupus erythematosis, discoid lupus, subacute cutaneous lupus erythematosus, cutaneous lupus erythematosus including chilblain lupus erythematosus, chronic arthritis, Sjogren's syndrome, inflammatory chronic rhinosinusitis, colitis, celiac disease, inflammatory bowel disease, Barrett's esophagus, inflammatory gastritis autoimmune nephritis, autoimmune vasculitis, autoimmune hepatitis, autoimmune carditis, autoimmune encephalitis, autoimmune diabetes, autoimmune diabetes nephritis, and autoimmune mediated hematological disease.

BRIEF DESCRIPTION OF THE DRAWINGS

FIGS. 4-6 depict bioavailability data from studies with the indicated compounds via multiple routes of administration.

FIG. 8 depicts graphs of cell viability in response to administration of C-1523-1a.

FIG. 9 depicts microscopy images of a blood smear from a CLL patient shown in the presence of malignant B-cells and a graph demonstrating cell viability in response to administration of ibrutinib and C-1523-1a.

FIG. 10 depicts a graph of MEC2 cell viability in response to the indicated doses of C-1523 and C-1523-1a.

FIG. 11 depicts bioavailability data from studies C-1523-1a administered intravenously.

FIG. 12A depicts a schematic summary of functional group modifications made to parent compound, DIDS, in order to generate derivative library for screening. FIG. 12B depicts a differential plot showing compound screening data at 10 µM for each compound tested for AID+/+ versus AID−/− (activation-induced cytidine deaminase) primary mouse B cells. Viability was assessed via MultiTox Fluor assay and viability is represented as relative fluorescence units (RFU) as measured by plate reader assay. RFU is plotted for AID−/−(y axis) versus AID+/+ (x axis) are plotted, with each data point representing an individual derivative. Compounds considered as strong candidates would allow for high retained viability in AID−/− cells while having very low viability in AID+/+ cells. The point representing C-1523, one of the strongest candidate molecules identified in the screen, is indicated with an arrow. FIG. 12C depicts the structure of C-1523. FIG. 12D depicts a bar chart representing the relative viability (AID+/AID−) of B cells following treatment with 10 µM of each compound from the library as represented in FIG. 12B. The data point representing C-1523 is indicated.

FIG. 13A depicts a viability analysis of C-1523-treated CH12-F3 cells 24 h after 0 or 2.5 Gy IR. Data are normalized to the fraction of cells for each IR dose that received DMSO vehicle only; error bars represent the SEM for three independent experiments. FIG. 13B depicts detection of RAD51 by immunofluorescence in primary mouse B cells 24 h after 0 or 2.5 Gy IR and treatment with C-1523 (100 nM) or vehicle. RAD51 staining is in red, nuclear DNA (DAPI-stained) is in blue. Scale bar: 10 µM.

FIGS. 14A-14B depict representative images of metaphases from HEK293T cells treated either with DMSO vehicle (FIG. 14A) or 100 nM C-1523 (FIG. 14B). Inset in FIG. 14A is a magnification of a single chromosome, as indicated by dashed lines, in order to more clearly demonstrate differential chromatid labeling and SCE events. Individual SCE events are indicated with arrowheads. Twenty metaphases from three individual experiments were scored for each treatment. FIG. 14C depicts the quantitation of median SCE per chromosome from metaphases scored as in FIGS. 14A and 14B. Error bars represent the SEM of three individual experiments. P values are given for unpaired Student's t test for significance. FIGS. 14D-14E depict DR-GFP assay in mouse ES cells (FIG. 14D) and human U2OS cells (FIG. 14E). Error bars represent the SEM of three individual experiments. P values are given for unpaired Student's t test for significance.

FIG. 15A depicts an analysis of primary WT (AID+/+, closed markers) and AID−/− (open markers) murine B cell proliferation under activating conditions (αCD40 and IL-4 on days 0 and 2) and treated with the indicated doses of C-1523 for 4 days. Measurement of cell proliferation was determined by Trypan Blue staining and counting of viable, non-staining, cells via hemocytometer. Data are represented as the mean cell count for each condition. FIG. 15B depicts data from experiments in which primary B cells from A were stained with PI on day 4 and analyzed via flow cytometry for the percentage of cells that were non-viable, PI-positive (PI+). FIG. 15C depicts RT-PCR analysis of AID expression in cultured human cell lines. Water (H2O) and RNA from HEK293T cells were employed as negative controls for template and AID expression, respectively, and human activated B lymphocyte RNA (Stim B) was used as a positive control. GAPDH expression was included as a loading control. FIG. 15D depicts viability analysis of CCRF-SB, MEC-1, and MEC-2 cells after 6 days in culture with the indicated concentrations of C-1523, 150 µM DIDS, or DMSO vehicle. Viability was determined by Trypan Blue staining and counting via hemocytometer. FIG. 15E depicts representative immunofluorescence images of phosphorylated γH2AX (green) and nuclei (DAPI, blue) in primary murine splenic B cells from AID−/− (left) or AID+/+ (WT, right) mice. Cells were activated with αCD40 and IL-4 and treated with 100 nM C-1523 for 3 d. Scale bars, 10 µM. FIG. 15F depicts quantitation of foci observed in AID−/− and WT cells represented in FIG. 15E. Data were grouped into categories of cells with low (1-2 foci per nucleus), moderate (3-10 foci per nucleus), or high (>10 foci per nucleus) amounts of DNA damage. Error bars represent the SEM for three independent experiments.

FIG. 16A depicts the measurement of viability of primary WT (AID+/+, circle markers), AID−/− (square markers), and p53−/− (triangle markers) B cells under activating conditions (αCD40 and IL-4 on days 0 and 2) and treated with either DMSO (filled in markers) or 100 nM C-1523 (open markers). Measurement of cell viability was determined by Trypan Blue staining and counting of viable, non-staining, cells via hemocytometer. Data are represented as the mean cell count for each condition. FIG. 16B depicts analysis of cell death on day 4 of cells treated as in FIG. 16A. Cell death was measured by Trypan Blue staining and counting of blue, dead cells via hemocytometer. FIG. 16C depicts quantitation of active caspase-3 (AC3) in primary B cells via immunofluorescence assay. Left, positive (WT, 10 Gy IR) and negative (0 Gy, and p53−/− 10 Gy) controls for AC3 induction. Right, measurement of AC3 via immunofluorescence in WT, AID−/−, and p53−/− B cells 3 days after activation (αCD40 and IL-4) and treatment with DMSO or 100 nM C-1523. Error bars represent the SEM for three independent experiments.

FIG. 17A depicts a schematic for the fold-change (FC) analysis performed on RNASeq data from the indicated treatment groups. RNA was prepared from cells 60 hours after activation (αCD40 and IL-4) and treatment with DMSO or 100 nM C-1523. Pathway analysis was performed by Ingenuity Pathway Analysis (IPA). FIGS. 17B-17D depict the top 10 pathways for the Unique to FC1 (FIG. 17B) and FC2 (FIG. 17C) analysis and all pathways for the FC1>FC2 (DOWN) and F2>FC1 (UP) analysis (FIG. 17D). Within each bar (in white), is the ratio of genes from that pathway implicated by IPA. The dashed line indicates the 0.05 significance threshold for significant (bars crossing it) vs non-significant pathways. The mechanism of cell death is non-apoptotic and is via mitotic catastrophe.

FIG. 18A depicts representative images used for micronuclei (MN) scoring. Top panels, examples of MN-negative and -positive cells. Activated WT B cells were treated with DMSO (middle panel) or cyclophosphamide (lower panel) for three days, and then imaged for micronuclei formation. Micronuclei are indicated by arrowheads. FIG. 18B depicts the quantitation of WT (dark gray bars) AID−/− (light gray bars), and p53−/− (black bars) cells scored as in FIG. 18A. Cells were treated with cyclophosphamide (5 µg/mL, as a positive control), DMSO, or 100 nM C-1523 for three days. FIG. 18C depicts the quantitation of MN assay in MEC-1 cells. Cells were treated as in FIG. 18B. 500 nuclei were scored for each sample, and data are represented as the average fraction of micronuclei in each sample. Data bars represent the SEM for three individual experiments.

DETAILED DESCRIPTION

Figure 1:
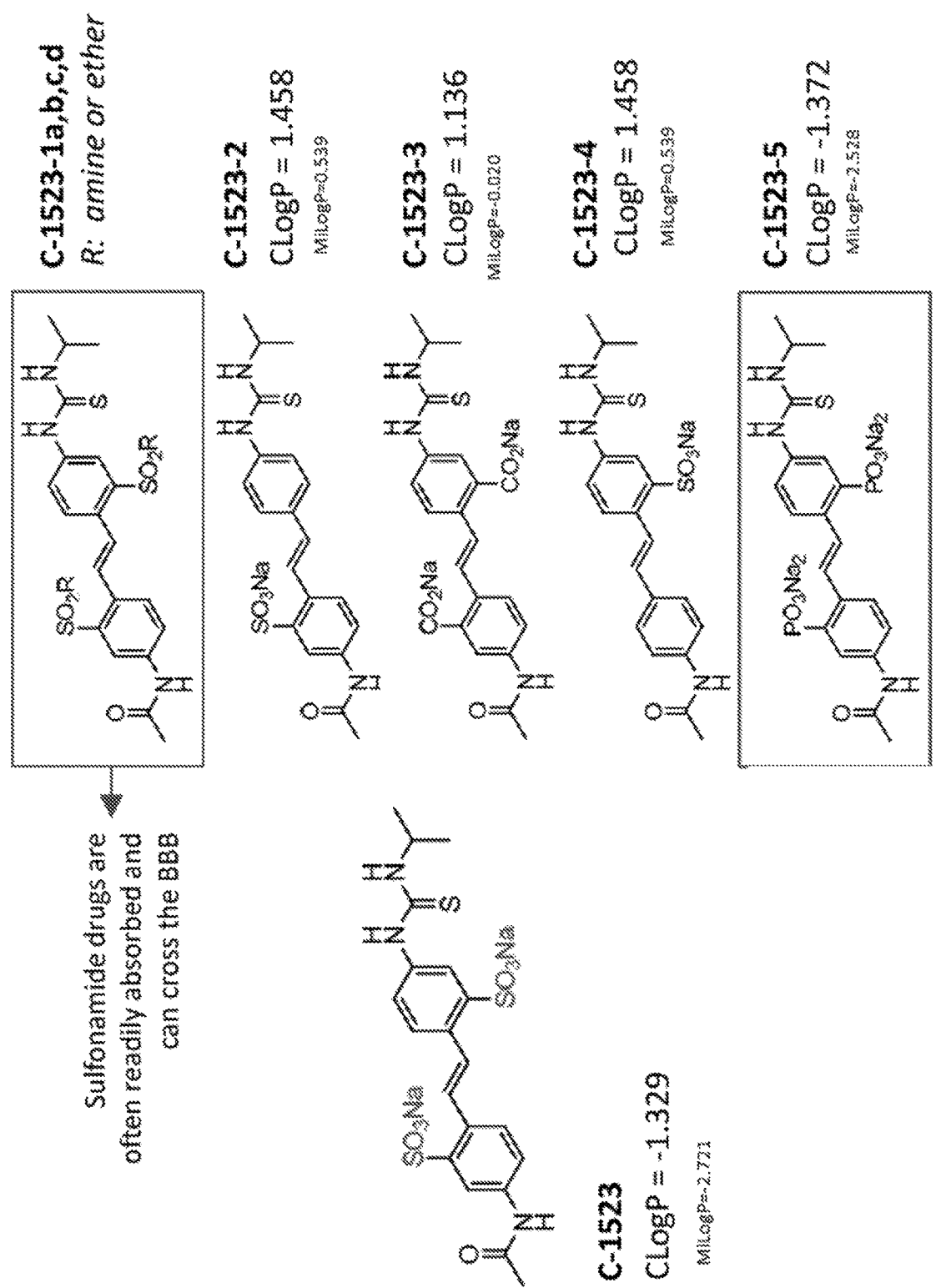
FIG. 1 depicts a schematic of certain compounds described herein.

As described herein, inhibition of endogenous DNA repair mechanisms is a therapeutic approach for treating a number of diseases, e.g., cancer. Described herein are inhibitors of DNA repair and methods of treating cancer, autoimmune disease, immune deficiency, or neurodegenerative disease with such inhibitors.

In one aspect, described herein is a composition comprising a compound of Formula I:

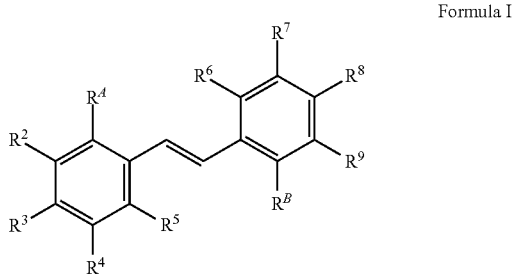

Formula I

In compounds of Formula I, at least one of $R^A$ and $R^B$ is not hydrogen.

$R^A$ can be hydrogen or $SO_2R^1$, $CO_2^-Y^+$, $PO_3^-(Y^+)_m$, wherein m is 2.

$R^B$ can be hydrogen or $SO_2R^{10}$, $CO_2^-Y^+$, $PO_3^-(Y^+)_m$, wherein m is 2.

$R^1$ can be $N(R^{22})_2$ or $OR^{23}$. In some embodiments, $R^1$ is $N(R^{22})_2$ and $R^{22}$ are independently H or $C_1$-$C_4$ alkyl, $C(O)(CH_2)_nCH_3$ wherein n=0, 1, 2, 3, 4, 5, or 6, or $R^{22}$ together with the nitrogen they are attached to form an optionally substituted 3-8 membered heterocyclyl. In some embodiments, $R^1$ is $NH_2$, $NHCH_3$, $NHCH(CH_3)_2$, $N(CH_3)_2$, pyrrolidinyl, $C(O)(CH_2)_2CH_3$, $C(O)(CH)_n(CH)_3$ wherein n=1, 2, 3, or azetidinyl. In some embodiments, $R^1$ is $OR^{23}$, wherein $R^{23}$ is $C_1$-$C_4$ alkyl. In some embodiments, $R^{23}$ is methyl, ethyl, propyl, isopropyl, butyl, isobutyl, pentyl, t-butyl, cyclopropyl. In one preferred embodiments, $R^{23}$ is isopropyl.

$R^2$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^2$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^2$ is hydrogen, OH, $OCH_3$, $NO_2$, $NH_2$, $OP(O)(OH)_2$. In some embodiments, $R^2$ is $C_1$-$C_4$ alkyl. In some embodiments, $R^2$ is methyl, ethyl, n-propyl, i-propyl, n-butyl, i-butyl or t-butyl. In some embodiments, $R^2$ is $SO_3H$, or $SO_3^-Y^+$, wherein Y can be sodium, potassium, aluminum, calcium, lithium, magnesium, barium, or zinc. In some embodiments, $R^2$ is $CO_2H$, or $CO_2^-Y^+$, wherein Y can be sodium, potassium, aluminum, calcium, lithium, magnesium, barium, or zinc. In some embodiments, $R^2$ is optionally substituted aryl. In some embodiments, aryl is cyclopentadiene, or phenyl. In some embodiments, $R^2$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^3$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^3$ is hydrogen, hetercyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, or $NHSO_2N(R^{22})_2$, wherein $R^{21}$ and $R^{22}$ are independently H or $C_1$-$C_4$ alkyl. In some embodiments, $R^3$ is hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, benzoxazolyl, or $NHC(O)NH$-cyclopropane. In some embodiments, $R^3$ is $C_1$-$C_4$ alkyl. In some embodiments, $R^3$ is methyl, ethyl, n-propyl, i-propyl, n-butyl, i-butyl or t-butyl. In some embodiments, $R^3$ is $SO_3H$, or $SO_3^-Y^+$, wherein Y can be sodium, potassium, aluminum, calcium, lithium, magnesium, barium, or zinc. In some embodiments, $R^3$ is $CO_2H$, or $CO_2^-Y^+$, wherein Y can be sodium, potassium, aluminum, calcium, lithium, magnesium, barium, or zinc. In some embodiments, $R^3$ is optionally substituted aryl. In some embodiments, aryl is cylcopentadiene, or phenyl. In some embodiments, $R^3$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^4$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^4$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^4$ is hydrogen, OH, $OCH_3$, $NO_2$, $NH_2$, $OP(O)(OH)_2$. In some embodiments, $R^4$ is $C_1$-$C_4$ alkyl. In some embodiments, $R^4$ is methyl, ethyl, n-propyl, i-propyl, n-butyl, i-butyl or t-butyl. In some embodiments, $R^4$ is $SO_3H$, or $SO_3^-Y^+$, wherein Y can be sodium, potassium, aluminum, calcium, lithium, magnesium, barium, or zinc. In some embodiments, $R^4$ is $CO_2H$, or $CO_2^-Y^+$, wherein Y can be sodium, potassium, aluminum, calcium, lithium, magnesium, barium, or zinc. In some embodiments, $R^4$ is optionally substituted aryl. In some embodiments, aryl is cylcopentadiene, or phenyl. In some embodiments, $R^4$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^5$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^5$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^5$ is hydrogen, OH, $OCH_3$, $NO_2$, $NH_2$, $OP(O)(OH)_2$. In some embodiments, $R^5$ is $C_1$-$C_4$ alkyl. In some embodiments, $R^5$ is methyl, ethyl, n-propyl, i-propyl, n-butyl, i-butyl or t-butyl. In some embodiments, $R^5$ is $SO_3H$, or $SO_3^-Y^+$, wherein Y can be sodium, potassium, aluminum, calcium, lithium, magnesium, barium, or zinc. In some embodiments, $R^5$ is $CO_2H$, or $CO_2^-Y^+$, wherein Y can be sodium, potassium, aluminum, calcium, lithium, magnesium, barium, or zinc. In some embodiments, $R^5$ is optionally substituted aryl. In some embodiments, aryl is cylcopentadiene, or phenyl. In some embodiments, $R^5$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^6$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^6$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^6$ is hydrogen, OH, $OCH_3$, $NO_2$, $NH_2$, $OP(O)(OH)_2$. In some embodiments, $R^6$ is $C_1$-$C_4$ alkyl. In some embodiments, $R^6$ is methyl, ethyl, n-propyl, i-propyl, n-butyl, i-butyl or t-butyl. In some embodiments, $R^6$ is $SO_3H$, or $SO_3^-Y^+$, wherein Y can be sodium, potassium, aluminum, calcium, lithium, magnesium, barium, or zinc. In some embodiments, $R^6$ is $CO_2H$, or $CO_2^-Y^+$, wherein Y can be sodium, potassium, aluminum, calcium, lithium, magnesium, barium, or zinc. In some embodiments, $R^6$ is optionally substituted aryl. In some embodiments, aryl is cylcopentadiene, or phenyl. In some embodiments, $R^6$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^7$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^7$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^7$ is hydrogen, OH, $OCH_3$, $NO_2$, $NH_2$, $OP(O)(OH)_2$. In some embodiments, $R^7$ is $C_1$-$C_4$ alkyl. In some embodiments, $R^7$ is methyl, ethyl, n-propyl, i-propyl, n-butyl, i-butyl or t-butyl. In some embodiments, $R^7$ is $SO_3H$, or $SO_3^-Y^+$, wherein Y can be sodium, potassium, aluminum, calcium, lithium, magnesium, barium, or zinc. In some embodiments, $R^7$ is $CO_2H$, or $CO_2^-Y^+$, wherein Y can be sodium, potassium, aluminum, calcium, lithium, magnesium, barium, or zinc. In some embodiments, $R^7$ is optionally substituted aryl. In some embodiments, aryl is cylcopentadiene, or phenyl. In some embodiments, $R^7$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^8$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^8$ is hydrogen, hetercyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, or $NHSO_2N(R^{22})_2$, wherein $R^{21}$ and $R^{22}$ are independently H or $C_1$-$C_4$ alkyl. In some embodiments, $R^8$ is hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, benzoxazolyl, or $NHC(O)NH$-cyclopropane. In some embodiments, $R^8$ is $C_1$-$C_4$ alkyl. In some embodiments, $R^8$ is methyl, ethyl, n-propyl, i-propyl, n-butyl, i-butyl or t-butyl. In some embodiments, $R^1$ is $SO_3H$, or $SO_3^-Y^+$, wherein Y can be sodium, potassium, aluminum, calcium, lithium, magnesium, barium, or zinc. In some embodiments, $R^8$ is $CO_2H$, or $CO_2^-Y^+$, wherein Y can be sodium, potassium, aluminum, calcium, lithium, magnesium, barium, or zinc. In some embodiments, $R^8$ is optionally substituted aryl. In some embodiments, aryl is cylcopentadiene, or phenyl. In some embodiments, $R^8$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^9$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^9$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^9$ is hydrogen, OH, $OCH_3$, $NO_2$, $NH_2$, $OP(O)(OH)_2$. In some embodiments, $R^9$ is $C_1$-$C_4$ alkyl. In some embodiments, $R^9$ is methyl, ethyl, n-propyl, i-propyl, n-butyl, i-butyl or t-butyl. In some embodiments, $R^1$ is $SO_3H$, or $SO_3^-Y^+$, wherein Y can be sodium, potassium, aluminum, calcium, lithium, magnesium, barium, or zinc. In some embodiments, $R^9$ is $CO_2H$, or $CO_2^-Y^+$, wherein Y can be sodium, potassium, aluminum, calcium, lithium, magnesium, barium, or zinc. In some embodiments, $R^9$ is optionally substituted aryl. In some embodiments, aryl is cylcopentadiene, or phenyl. In some embodiments, $R^9$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^{10}$ can be $N(R^{22})_2$ or $OR^{23}$. In some embodiments, $R^{10}$ is $N(R^{22})_2$ and $R^{22}$ are independently H or $C_1$-$C_4$ alkyl, $C(O)CH_2)_nCH_3$ wherein n=0, 1, 2, 3, 4, 5, 6, or $R^{22}$ together with the nitrogen they are attached to form an optionally substituted 3-8 membered heterocyclyl. In some embodiments, $R^{10}$ is $NH_2$, $NHCH_3$, $NHCH(CH_3)_2$, $N(CH_3)_2$, pyrrolidinyl, $C(O)(CH_2)_2CH_3$, $C(O)(CH)_n(CH)_3$ wherein n=1, 2, 3, or azetidinyl. In some embodiments, $R^{10}$ is $OR^{23}$, wherein $R^{23}$ is $C_1$-$C_4$ alkyl. In some embodiments, $R^{23}$ is methyl, ethyl, propyl, isopropyl, butyl, isobutyl, pentyl, t-butyl, cyclopropyl. In one preferred embodiment, $R^{23}$ is isopropyl.

Each $R^{21}$ can be selected independently from the group consisting of hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, and any combinations thereof. Preferably, $R^{21}$ is hydrogen or a linear or branched $C_1$-$C_{10}$ alkyl. In some embodiments, $R^{21}$ can be methyl, ethyl, propyl, isopropyl, butyl, isobutyl, pentyl, t-butyl, cyclopropyl, or $CH_2OCH_3$.

Each $R^{22}$ can be selected independently from the group consisting of hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, and any combinations thereof. Preferably, $R^{22}$ is hydrogen or a linear or branched $C_1$-$C_{10}$ alkyl. In some embodiments, $R^{22}$ can be hydrogen, methyl, ethyl, propyl, isopropyl, butyl, isobutyl, pentyl, t-butyl, or cyclopropyl. In some embodiments, the two $R^{22}$ together with the nitrogen they are attached to form an optionally substituted 3-8 membered heterocyclyl.

Each $R^{23}$ can be selected independently from the group consisting of hydrogen, $C_1$-$C_6$ alkyl. In some embodiments, $R^{23}$ is methyl, ethyl, propyl, isopropyl, butyl, isobutyl, pentyl, t-butyl, cyclopropyl. In one preferred embodiment, $R^{23}$ is isopropyl. In another embodiment, $R^{23}$ is t-butyl.

Each $Y^+$ is independently a cation, e.g., a monovalent cation. Exemplary cations include, but are not limited to, sodium, potassium, aluminum, calcium, lithium, magnesium, barium, zinc, ammonium and aminium. In some embodiments, $R^3$ and $R^8$ can be same or different. In some embodiments, at least one of $R^3$ and $R^8$ is not hydrogen. In some embodiments, both of $R^3$ and $R^8$ are not hydrogen. In some embodiments, $R^3$ and $R^8$ are selected independently from the group consisting of hydrogen, hetercyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R22)_2$, wherein $R^{21}$ can be H or $C_1$-$C_4$ alkyl and $R^{22}$ can be H or $C_1$-$C_{10}$ alkyl. For example, $R^3$ and $R^8$ can be selected independently from the group consisting of hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, benzoxazolyl, or $NHC(O)NH$-cyclopropane.

In some embodiments, $R^3$ and $R^8$ are selected independently from the group consisting of hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, benzoxazolyl, or $NHC(O)NH$-cyclopropane. For example, one of $R^3$ and $R^8$ can be H and the other can be $NH_2$, one of $R^3$ and $R^8$ can be H and the other can be $NHCH_3$, one of $R^3$ and $R^8$ can be H and the other can be $N(CH_3)_2$, one of $R^3$ and $R^8$ can be H and the other can be $NHC(O)CH_3$, one of $R^3$ and $R^8$ can be H and the other can be $NHC(O)CH(CH_3)_2$, one of $R^3$ and $R^8$ can be H and the other can be $NHC(O)CH_2OCH_3$, one of $R^3$ and $R^8$ can be H and the other can be $NHSO_2$—$CH_3$, one of $R^3$ and $R^8$ can be H and the other can be $NHSO_2$—$CH(CH_3)_2$, one of $R^3$ and $R^8$ can be H and the other can be $NHSO_2$-cyclopropane, one of $R^3$ and $R^8$ can be H and the other can be $NHSO_2$—$NHCH_3$, one of $R^3$ and $R^8$ can be H and the other can be $NHSO_2$—$N(CH_3)_2$, one of $R^3$ and $R^8$ can be H and the other can be $NHSO_2$—$NHCH(CH_3)_2$, one of $R^3$ and $R^8$ can be H and the other can be $NHSO_2$—NH-cyclopropane, one of $R^3$ and $R^8$ can be H and the other can be $NHC(S)NH$—$CH_3$, one of $R^3$ and $R^8$ can be H and the other can be $NHC(S)NH$—$CH(CH_3)_2$, one of $R^3$ and $R^8$ can be H and the other can be $NHC(S)NH$-cyclopropane, one of $R^3$ and $R^8$ can be H and the other can be $NHC(O)NH$—$CH_3$, one of $R^3$ and $R^8$ can be H and the other can be $NHC(O)NH$—$CH(CH_3)_2$, one of $R^3$ and $R^8$ can be H and the other can be $NHC(O)NH$-cyclopropane, one of $R^3$ and $R^8$ can be $NH_2$ and the other can be $NHCH_3$, one of $R^3$ and $R^8$ can be $NH_2$ and the other can be $N(CH_3)_2$, one of $R^3$ and $R^8$ can be $NH_2$ and the other can be $NHC(O)CH_3$, one of $R^3$ and $R^8$ can be $NH_2$ and the other can be $NHC(O)CH(CH_3)_2$, one of $R^3$ and $R^8$ can be $NH_2$ and the other can be $NHC(O)CH_2OCH_3$, one of $R^3$ and $R^8$ can be $NH_2$ and the other can be $NHSO_2$—$CH_3$, one of $R^3$ and $R^8$ can be $NH_2$ and the other can be $NHSO_2$—$CH(CH_3)_2$, one of $R^3$ and $R^8$ can be $NH_2$ and the other can be $NHSO_2$-cyclopropane, one of $R^3$ and $R^8$ can be $NH_2$ and the other can be $NHSO_2$—$NHCH_3$, one of $R^3$ and $R^8$ can be $NH_2$ and the other can be $NHSO_2$—$N(CH_3)_2$, one of $R^3$ and $R^8$ can be $NH_2$ and the other can be $NHSO_2$—$NHCH(CH_3)_2$, one of $R^3$ and $R^8$ can be $NH_2$ and the other can be $NHSO_2$—NH-cyclopropane, one of $R^3$ and $R^8$ can be $NH_2$ and the other can be $NHC(S)NH$—$CH_3$, one of $R^3$ and $R^8$ can be $NH_2$ and the other can be $NHC(S)NH$—$CH(CH_3)_2$, one of $R^3$ and $R^8$ can be $NH_2$ and the other can be $NHC(S)NH$-cyclopropane, one of $R^3$ and $R^8$ can be $NH_2$ and the other can be $NHC(O)NH$—$CH_3$, one of $R^3$ and $R^8$ can be $NH_2$ and the other can be $NHC(O)NH$—$CH(CH_3)_2$, one of $R^3$ and $R^8$ can be $NH_2$ and the other can be NHC(O)NH-cyclopropane, one of $R^3$ and $R^8$ can be NHCH$_3$ and the other can be N(CH$_3$)$_2$, one of $R^3$ and $R^8$ can be NHCH$_3$ and the other can be NHC(O)CH$_3$, one of $R^3$ and $R^8$ can be NHCH$_3$ and the other can be NHC(O)CH(CH$_3$)$_2$, one of $R^3$ and $R^8$ can be NHCH$_3$ and the other can be NHC(O)CH$_2$OCH$_3$, one of $R^3$ and $R^8$ can be NHCH$_3$ and the other can be NHSO$_2$—CH$_3$, one of $R^3$ and $R^8$ can be NHCH$_3$ and the other can be NHSO$_2$—CH(CH$_3$)$_2$, one of $R^3$ and $R^8$ can be NHCH$_3$ and the other can be NHSO$_2$-cyclopropane, one of $R^3$ and $R^8$ can be NHCH$_3$ and the other can be NHSO$_2$—NHCH$_3$, one of $R^3$ and $R^8$ can be NHCH$_3$ and the other can be NHSO$_2$—N(CH$_3$)$_2$, one of $R^3$ and $R^8$ can be NHCH$_3$ and the other can be NHSO$_2$—NHCH(CH$_3$)$_2$, one of $R^3$ and $R^8$ can be NHCH$_3$ and the other can be NHSO$_2$—NH-cyclopropane, one of $R^3$ and $R^8$ can be NHCH$_3$ and the other can be NHC(S)NH—CH$_3$, one of $R^3$ and $R^8$ can be NHCH$_3$ and the other can be NHC(S)NH—CH(CH$_3$)$_2$, one of $R^3$ and $R^8$ can be NHCH$_3$ and the other can be NHC(S)NH-cyclopropane, one of $R^3$ and $R^8$ can be NHCH$_3$ and the other can be NHC(O)NH—CH$_3$, one of $R^3$ and $R^8$ can be NHCH$_3$ and the other can be NHC(O)NH—CH(CH$_3$)$_2$, one of $R^3$ and $R^8$ can be NHCH$_3$ and the other can be NHC(O)NH-cyclopropane, one of $R^3$ and $R^8$ can be N(CH$_3$)$_2$ and the other can be NHC(O)CH$_3$, one of $R^3$ and $R^8$ can be N(CH$_3$)$_2$ and the other can be NHC(O)CH(CH$_3$)$_2$, one of $R^3$ and $R^8$ can be N(CH$_3$)$_2$ and the other can be NHC(O)CH$_2$OCH$_3$, one of $R^3$ and $R^8$ can be N(CH$_3$)$_2$ and the other can be NHSO$_2$—CH$_3$, one of $R^3$ and $R^8$ can be N(CH$_3$)$_2$ and the other can be NHSO$_2$—CH(CH$_3$)$_2$, one of $R^3$ and $R^8$ can be N(CH$_3$)$_2$ and the other can be NHSO$_2$-cyclopropane, one of $R^3$ and $R^8$ can be N(CH$_3$)$_2$ and the other can be NHSO$_2$—NHCH$_3$, one of $R^3$ and $R^8$ can be N(CH$_3$)$_2$ and the other can be NHSO$_2$—N(CH$_3$)$_2$, one of $R^3$ and $R^8$ can be N(CH$_3$)$_2$ and the other can be NHSO$_2$—NHCH(CH$_3$)$_2$, one of $R^3$ and $R^8$ can be N(CH$_3$)$_2$ and the other can be NHSO$_2$—NH-cyclopropane, one of $R^3$ and $R^8$ can be N(CH$_3$)$_2$ and the other can be NHC(S)NH—CH$_3$, one of $R^3$ and $R^8$ can be N(CH$_3$)$_2$ and the other can be NHC(S)NH—CH(CH$_3$)$_2$, one of $R^3$ and $R^8$ can be N(CH$_3$)$_2$ and the other can be NHC(S)NH-cyclopropane, one of $R^3$ and $R^8$ can be N(CH$_3$)$_2$ and the other can be NHC(O)NH—CH$_3$, one of $R^3$ and $R^8$ can be N(CH$_3$)$_2$ and the other can be NHC(O)NH—CH(CH$_3$)$_2$, one of $R^3$ and $R^8$ can be N(CH$_3$)$_2$ and the other can be NHC(O)NH-cyclopropane, one of $R^3$ and $R^8$ can be NHC(O)CH$_3$ and the other can be NHC(O)CH(CH$_3$)$_2$, one of $R^3$ and $R^8$ can be NHC(O)CH$_3$ and the other can be NHC(O)CH$_2$OCH$_3$, one of $R^3$ and $R^8$ can be NHC(O)CH$_3$ and the other can be NHSO$_2$—CH$_3$, one of $R^3$ and $R^8$ can be NHC(O)CH$_3$ and the other can be NHSO$_2$—CH(CH$_3$)$_2$, one of $R^3$ and $R^8$ can be NHC(O)CH$_3$ and the other can be NHSO$_2$-cyclopropane, one of $R^3$ and $R^8$ can be NHC(O)CH$_3$ and the other can be NHSO$_2$—NHCH$_3$, one of $R^3$ and $R^8$ can be NHC(O)CH$_3$ and the other can be NHSO$_2$—N(CH$_3$)$_2$, one of $R^3$ and $R^8$ can be NHC(O)CH$_3$ and the other can be NHSO$_2$—NHCH(CH$_3$)$_2$, one of $R^3$ and $R^8$ can be NHC(O)CH$_3$ and the other can be NHSO$_2$—NH-cyclopropane, one of $R^3$ and $R^8$ can be NHC(O)CH$_3$ and the other can be NHC(S)NH—CH$_3$, one of $R^3$ and $R^8$ can be NHC(O)CH$_3$ and the other can be NHC(S)NH—CH(CH$_3$)$_2$, one of $R^3$ and $R^8$ can be NHC(O)CH$_3$ and the other can be NHC(S)NH-cyclopropane, one of $R^3$ and $R^8$ can be NHC(O)CH$_3$ and the other can be NHC(O)NH—CH$_3$, one of $R^3$ and $R^8$ can be NHC(O)CH$_3$ and the other can be NHC(O)NH—CH(CH$_3$)$_2$, one of $R^3$ and $R^8$ can be NHC(O)CH$_3$ and the other can be NHC(O)NH-cyclopropane, one of $R^3$ and $R^8$ can be NHC(O)CH(CH$_3$)$_2$ and the other can be NHC(O)CH$_2$OCH$_3$, one of $R^3$ and $R^8$ can be NHC(O)CH(CH$_3$)$_2$ and the other can be NHSO$_2$—CH$_3$, one of $R^3$ and $R^8$ can be NHC(O)CH(CH$_3$)$_2$ and the other can be NHSO$_2$—CH(CH$_3$)$_2$, one of $R^3$ and $R^8$ can be NHC(O)CH(CH$_3$)$_2$ and the other can be NHSO$_2$-cyclopropane, one of $R^3$ and $R^8$ can be NHC(O)CH(CH$_3$)$_2$ and the other can be NHSO$_2$—NHCH$_3$, one of $R^3$ and $R^8$ can be NHC(O)CH(CH$_3$)$_2$ and the other can be NHSO$_2$—N(CH$_3$)$_2$, one of $R^3$ and $R^8$ can be NHC(O)CH(CH$_3$)$_2$ and the other can be NHSO$_2$—NHCH(CH$_3$)$_2$, one of $R^3$ and $R^8$ can be NHC(O)CH(CH$_3$)$_2$ and the other can be NHSO$_2$—NH-cyclopropane, one of $R^3$ and $R^8$ can be NHC(O)CH(CH$_3$)$_2$ and the other can be NHC(S)NH—CH$_3$, one of $R^3$ and $R^8$ can be NHC(O)CH(CH$_3$)$_2$ and the other can be NHC(S)NH—CH(CH$_3$)$_2$, one of $R^3$ and $R^8$ can be NHC(O)CH(CH$_3$)$_2$ and the other can be NHC(S)NH-cyclopropane, one of $R^3$ and $R^8$ can be NHC(O)CH(CH$_3$)$_2$ and the other can be NHC(O)NH—CH$_3$, one of $R^3$ and $R^8$ can be NHC(O)CH(CH$_3$)$_2$ and the other can be NHC(O)NH—CH(CH$_3$)$_2$, one of $R^3$ and $R^8$ can be NHC(O)CH(CH$_3$)$_2$ and the other can be NHC(O)NH-cyclopropane, one of $R^3$ and $R^8$ can be NHC(O)CH$_2$OCH$_3$ and the other can be NHSO$_2$—CH$_3$, one of $R^3$ and $R^8$ can be NHC(O)CH$_2$OCH$_3$ and the other can be NHSO$_2$—CH(CH$_3$)$_2$, one of $R^3$ and $R^8$ can be NHC(O)CH$_2$OCH$_3$ and the other can be NHSO$_2$-cyclopropane, one of $R^3$ and $R^8$ can be NHC(O)CH$_2$OCH$_3$ and the other can be NHSO$_2$—NHCH$_3$, one of $R^3$ and $R^8$ can be NHC(O)CH$_2$OCH$_3$ and the other can be NHSO$_2$—N(CH$_3$)$_2$, one of $R^3$ and $R^8$ can be NHC(O)CH$_2$OCH$_3$ and the other can be NHSO$_2$—NHCH(CH$_3$)$_2$, one of $R^3$ and $R^8$ can be NHC(O)CH$_2$OCH$_3$ and the other can be NHSO$_2$—NH-cyclopropane, one of $R^3$ and $R^8$ can be NHC(O)CH$_2$OCH$_3$ and the other can be NHC(S)NH—CH$_3$, one of $R^3$ and $R^8$ can be NHC(O)CH$_2$OCH$_3$ and the other can be NHC(S)NH—CH(CH$_3$)$_2$, one of $R^3$ and $R^8$ can be NHC(O)CH$_2$OCH$_3$ and the other can be NHC(S)NH-cyclopropane, one of $R^3$ and $R^8$ can be NHC(O)CH$_2$OCH$_3$ and the other can be NHC(O)NH—CH$_3$, one of $R^3$ and $R^8$ can be NHC(O)CH$_2$OCH$_3$ and the other can be NHC(O)NH—CH(CH$_3$)$_2$, one of $R^3$ and $R^8$ can be NHC(O)CH$_2$OCH$_3$ and the other can be NHC(O)NH-cyclopropane, one of $R^3$ and $R^8$ can be NHSO$_2$—CH$_3$ and the other can be NHSO$_2$—CH(CH$_3$)$_2$, one of $R^3$ and $R^8$ can be NHSO$_2$—CH$_3$ and the other can be NHSO$_2$-cyclopropane, one of $R^3$ and $R^8$ can be NHSO$_2$—CH$_3$ and the other can be NHSO$_2$—NHCH$_3$, one of $R^3$ and $R^8$ can be NHSO$_2$—CH$_3$ and the other can be NHSO$_2$—N(CH$_3$)$_2$, one of $R^3$ and $R^8$ can be NHSO$_2$—CH$_3$ and the other can be NHSO$_2$—NHCH(CH$_3$)$_2$, one of $R^3$ and $R^8$ can be NHSO$_2$—CH$_3$ and the other can be NHSO$_2$—NH-cyclopropane, one of $R^3$ and $R^8$ can be NHSO$_2$—CH$_3$ and the other can be NHC(S)NH—CH$_3$, one of $R^3$ and $R^8$ can be NHSO$_2$—CH$_3$ and the other can be NHC(S)NH—CH(CH$_3$)$_2$, one of $R^3$ and $R^8$ can be NHSO$_2$—CH$_3$ and the other can be NHC(S)NH-cyclopropane, one of $R^3$ and $R^8$ can be NHSO$_2$—CH$_3$ and the other can be NHC(O)NH—CH$_3$, one of $R^3$ and $R^8$ can be NHSO$_2$—CH$_3$ and the other can be NHC(O)NH—CH(CH$_3$)$_2$, one of $R^3$ and $R^8$ can be NHSO$_2$—CH$_3$ and the other can be NHC(O)NH-cyclopropane, one of $R^3$ and $R^8$ can be NHSO$_2$—CH(CH$_3$)$_2$ and the other can be NHSO$_2$-cyclopropane, one of $R^3$ and $R^8$ can be NHSO$_2$—CH(CH$_3$)$_2$ and the other can be NHSO$_2$—NHCH$_3$, one of $R^3$ and $R^8$ can be NHSO$_2$—CH(CH$_3$)$_2$ and the other can be NHSO$_2$—N(CH$_3$)$_2$, one of $R^3$ and $R^8$ can be NHSO$_2$—CH(CH$_3$)$_2$ and the other can be NHSO$_2$—NHCH(CH$_3$)$_2$, one of $R^3$ and $R^8$ can be NHSO$_2$—CH(CH$_3$)$_2$ and the other can be NHSO$_2$—NH-cyclopropane, one of $R^3$ and $R^8$ can be NHSO$_2$—CH(CH$_3$)$_2$ and the other can be NHC(S)NH—CH$_3$, one of $R^3$ and $R^8$ can be NHSO$_2$—CH(CH$_3$)$_2$ and the other can be NHC(S)NH—CH(CH$_3$)$_2$, one of $R^3$ and R$^8$ can be NHSO$_2$—CH(CH$_3$)$_2$ and the other can be NHC(S)NH-cyclopropane, one of R$^3$ and R$^8$ can be NHSO$_2$—CH(CH$_3$)$_2$ and the other can be NHC(O)NH—CH$_3$, one of R$^3$ and R$^8$ can be NHSO$_2$—CH(CH$_3$)$_2$ and the other can be NHC(O)NH—CH(CH$_3$)$_2$, one of R$^3$ and R$^8$ can be NHSO$_2$—CH(CH$_3$)$_2$ and the other can be NHC(O)NH-cyclopropane, one of R$^3$ and R$^8$ can be NHSO$_2$-cyclopropane and the other can be NHSO$_2$—NHCH$_3$, one of R$^3$ and R$^8$ can be NHSO$_2$-cyclopropane and the other can be NHSO$_2$—N(CH$_3$)$_2$, one of R$^3$ and R$^8$ can be NHSO$_2$-cyclopropane and the other can be NHSO$_2$—NHCH(CH$_3$)$_2$, one of R$^3$ and R$^8$ can be NHSO$_2$-cyclopropane and the other can be NHSO$_2$—NH-cyclopropane, one of R$^3$ and R$^8$ can be NHSO$_2$-cyclopropane and the other can be NHC(S)NH—CH$_3$, one of R$^3$ and R$^8$ can be NHSO$_2$-cyclopropane and the other can be NHC(S)NH—CH(CH$_3$)$_2$, one of R$^3$ and R$^8$ can be NHSO$_2$-cyclopropane and the other can be NHC(S)NH-cyclopropane, one of R$^3$ and R$^8$ can be NHSO$_2$-cyclopropane and the other can be NHC(O)NH—CH$_3$, one of R$^3$ and R$^8$ can be NHSO$_2$-cyclopropane and the other can be NHC(O)NH—CH(CH$_3$)$_2$, one of R$^3$ and R$^8$ can be NHSO$_2$-cyclopropane and the other can be NHC(O)NH-cyclopropane, one of R$^3$ and R$^8$ can be NHSO$_2$—NHCH$_3$ and the other can be NHSO$_2$—N(CH$_3$)$_2$, one of R$^3$ and R$^8$ can be NHSO$_2$—NHCH$_3$ and the other can be NHSO$_2$—NHCH(CH$_3$)$_2$, one of R$^3$ and R$^8$ can be NHSO$_2$—NHCH$_3$ and the other can be NHSO$_2$—NH-cyclopropane, one of R$^3$ and R$^8$ can be NHSO$_2$—NHCH$_3$ and the other can be NHC(S)NH—CH$_3$, one of R$^3$ and R$^8$ can be NHSO$_2$—NHCH$_3$ and the other can be NHC(S)NH—CH(CH$_3$)$_2$, one of R$^3$ and R$^8$ can be NHSO$_2$—NHCH$_3$ and the other can be NHC(S)NH-cyclopropane, one of R$^3$ and R$^8$ can be NHSO$_2$—NHCH$_3$ and the other can be NHC(O)NH—CH$_3$, one of R$^3$ and R$^8$ can be NHSO$_2$—NHCH$_3$ and the other can be NHC(O)NH—CH(CH$_3$)$_2$, one of R$^3$ and R$^8$ can be NHSO$_2$—NHCH$_3$ and the other can be NHC(O)NH-cyclopropane, one of R$^3$ and R$^8$ can be NHSO$_2$—N(CH$_3$)$_2$ and the other can be NHSO$_2$—NHCH(CH$_3$)$_2$, one of R$^3$ and R$^8$ can be NHSO$_2$—N(CH$_3$)$_2$ and the other can be NHSO$_2$—NH-cyclopropane, one of R$^3$ and R$^8$ can be NHSO$_2$—N(CH$_3$)$_2$ and the other can be NHC(S)NH—CH$_3$, one of R$^3$ and R$^8$ can be NHSO$_2$—N(CH$_3$)$_2$ and the other can be NHC(S)NH—CH(CH$_3$)$_2$, one of R$^3$ and R$^8$ can be NHSO$_2$—N(CH$_3$)$_2$ and the other can be NHC(S)NH-cyclopropane, one of R$^3$ and R$^8$ can be NHSO$_2$—N(CH$_3$)$_2$ and the other can be NHC(O)NH—CH$_3$, one of R$^3$ and R$^8$ can be NHSO$_2$—N(CH$_3$)$_2$ and the other can be NHC(O)NH—CH(CH$_3$)$_2$, one of R$^3$ and R$^8$ can be NHSO$_2$—N(CH$_3$)$_2$ and the other can be NHC(O)NH-cyclopropane, one of R$^3$ and R$^8$ can be NHSO$_2$—NHCH(CH$_3$)$_2$ and the other can be NHSO$_2$—NH-cyclopropane, one of R$^3$ and R$^8$ can be NHSO$_2$—NHCH(CH$_3$)$_2$ and the other can be NHC(S)NH—CH$_3$, one of R$^3$ and R$^8$ can be NHSO$_2$—NHCH(CH$_3$)$_2$ and the other can be NHC(S)NH—CH(CH$_3$)$_2$, one of R$^3$ and R$^8$ can be NHSO$_2$—NHCH(CH$_3$)$_2$ and the other can be NHC(S)NH-cyclopropane, one of R$^3$ and R$^8$ can be NHSO$_2$—NHCH(CH$_3$)$_2$ and the other can be NHC(O)NH—CH$_3$, one of R$^3$ and R$^8$ can be NHSO$_2$—NHCH(CH$_3$)$_2$ and the other can be NHC(O)NH—CH(CH$_3$)$_2$, one of R$^3$ and R$^8$ can be NHSO$_2$—NHCH(CH$_3$)$_2$ and the other can be NHC(O)NH-cyclopropane, one of R$^3$ and R$^8$ can be NHSO$_2$—NH-cyclopropane and the other can be NHC(S)NH—CH$_3$, one of R$^3$ and R$^8$ can be NHSO$_2$—NH-cyclopropane and the other can be NHC(S)NH—CH(CH$_3$)$_2$, one of R$^3$ and R$^8$ can be NHSO$_2$—NH-cyclopropane and the other can be NHC(S)NH-cyclopropane, one of R$^3$ and R$^8$ can be NHSO$_2$—NH-cyclopropane and the other can be NHC(O)NH—CH$_3$, one of R$^3$ and R$^8$ can be NHSO$_2$—NH-cyclopropane and the other can be NHC(O)NH—CH(CH$_3$)$_2$, one of R$^3$ and R$^8$ can be NHSO$_2$—NH-cyclopropane and the other can be NHC(O)NH-cyclopropane, one of R$^3$ and R$^8$ can be NHC(S)NHCH$_3$ and the other can be NHC(S)NH—CH(CH$_3$)$_2$, one of R$^3$ and R$^8$ can be NHC(S)NHCH$_3$ and the other can be NHC(S)NH-cyclopropane, one of R$^3$ and R$^8$ can be NHC(S)NHCH$_3$ and the other can be NHC(O)NH—CH$_3$, one of R$^3$ and R$^8$ can be NHC(S)NHCH$_3$ and the other can be NHC(O)NH—CH(CH$_3$)$_2$, one of R$^3$ and R$^8$ can be NHC(S)NHCH$_3$ and the other can be NHC(O)NH-cyclopropane, one of R$^3$ and R$^8$ can be NHC(S)NH—CH(CH$_3$)$_2$ and the other can be NHC(S)NH-cyclopropane, one of R$^3$ and R$^8$ can be NHC(S)NH—CH(CH$_3$)$_2$ and the other can be NHC(O)NH—CH$_3$, one of R$^3$ and R$^8$ can be NHC(S)NH—CH(CH$_3$)$_2$ and the other can be NHC(O)NH—CH(CH$_3$)$_2$, one of R$^3$ and R$^8$ can be NHC(S)NH—CH(CH$_3$)$_2$ and the other can be NHC(O)NH-cyclopropane, one of R$^3$ and R$^8$ can be NHC(O)NH—CH$_3$ and the other can be NHC(O)NH—CH(CH$_3$)$_2$, one of R$^3$ and R$^8$ can be NHC(O)NH—CH$_3$ and the other can be NHC(O)NH-cyclopropane, or one of R$^3$ and R$^8$ can be NHC(O)NH—CH(CH$_3$)$_2$ and the other can be NHC(O)NH—CH(CH$_3$)$_2$.

In some embodiments, R$^A$ is SO$_2$R$^1$ and R$^B$ is hydrogen or SO$_2$R$^{10}$. In some embodiments, R$^A$ is SO$_2$R$^1$ and R$^B$ is SO$_2$R$^{10}$.

In some embodiments, R$^A$ is SO$_2$R$^1$, R$^B$ is hydrogen or SO$_2$R$^{10}$, and at least one of R$^1$ and R$^{10}$ (e.g., one or both) is N(R$^{22}$)$_2$. In some embodiments, at least one of R$^1$ and R$^{10}$ (e.g., one or both) can be N(R$^{22}$)$_2$ and R$^3$ and R$^8$ are selected independently from the group consisting of hydrogen, heterocyclyl, OR$^{21}$, NO$_2$, N(R$^{22}$)$_2$, N═C═S, NHC(O)R$^{21}$, NHSO$_2$R$^{21}$, N(R$^{22}$)$_2$, NHC(O)N(R$^{22}$)$_2$, NHC(S)N(R$^{22}$)$_2$, and NHSO$_2$N(R$^{22}$)$_2$, wherein R$^{21}$ and R$^{22}$ are independently H or C$_1$-C$_4$ alkyl. For example, at least one (e.g., one or both) of R$^1$ and R$^{10}$ can be N(R$^{22}$)$_2$ and R$^3$ and R$^8$ can be selected independently from the group consisting of hydrogen, OH, OCH$_3$, N═C═S, NH$_2$, NHCH$_3$, NO$_2$, NH-octadecane, NHC(O)CH$_3$, NHC(O)CH(CH$_3$)$_2$, NHC(O)CH$_2$OCH$_3$, NHSO$_2$CH$_3$, NHSO$_2$-cyclopropane, NHSO$_2$CH(CH$_3$)$_2$, NHSO$_2$N(CH$_3$)$_2$, NHC(S)NHCH$_3$, NHC(S)NHCH(CH$_3$)$_2$, NHC(S)NH-cyclopropane, NHC(O)NHCH$_3$, NHC(O)NHCH(CH$_3$)$_2$, benzoxazolyl, or NHC(O)NH-cyclopropane.

In some embodiments, R$^A$ is SO$_2$R$^1$, R$^B$ is hydrogen or SO$_2$R$^{10}$, and at least one of R$^1$ and R$^{10}$ (e.g., one or both) can be N(R$^{22}$)$_2$, and R$^3$ and R$^8$ are selected independently from the group consisting of hydrogen, N═C═S, NHC(O)R$^{21}$, NHSO$_2$R$^{21}$, N(R$^{22}$)$_2$, NHC(O)N(R$^{22}$)$_2$, NHC(S)N(R$^{22}$)$_2$, and NHSO$_2$N(R$^{22}$)$_2$. For example, at least one (e.g., one or both) of R$^1$ and R$^{10}$ can be N(R$^{22}$)$_2$, and R$^3$ and R$^8$ are the same and can be selected from the group consisting of hydrogen, N═C═S, NH$_2$, NHC(O)CH$_3$, NHC(O)CH(CH$_3$)$_2$, NHC(O)CH$_2$OCH$_3$, NHSO$_2$CH$_3$, NHSO$_2$-cyclopropane, NHSO$_2$CH(CH$_3$)$_2$, NHSO$_2$N(CH$_3$)$_2$, NHC(S)NHCH$_3$, NHC(S)NHCH(CH$_3$)$_2$, NHC(S)NH-cyclopropane, NHC(O)NHCH$_3$, NHC(O)NHCH(CH$_3$)$_2$, and NHC(O)NH-cyclopropane. In another non-limiting example, at least one (e.g., one or both) of R$^1$ and R$^{10}$ can be N(R$^{22}$) and R$^3$ and R$^8$ are different and can be selected from the group consisting of hydrogen, N═C═S, NH$_2$, NHC(O)CH$_3$, NHC(O)CH(CH$_3$)$_2$, NHC(O)CH$_2$OCH$_3$, NHSO$_2$CH$_3$, NHSO$_2$-cyclopropane, NHSO$_2$CH(CH$_3$)$_2$, NHSO$_2$N(CH$_3$)$_2$, NHC(S)NHCH$_3$, NHC(S)NHCH(CH$_3$)$_2$, NHC(S)NH-cyclopropane, NHC(O)NHCH$_3$, NHC(O)NHCH(CH$_3$)$_2$, and NHC(O)NH-cyclopropane.

In some embodiments, $R^A$ is $SO_2R^1$, $R^B$ is hydrogen or $SO_2R^{10}$, at least one of $R^1$ and $R^{10}$ is $N(R^{22})_2$, and $R^3$ and $R^8$ are selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. For example, at least one (e.g., one or both) of $R^1$ and $R^{10}$ can be $N(R^{22})_2$, and $R^3$ and $R^8$ are the same and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane. In another non-limiting example, at least one (e.g., one or both) of $R^1$ and $R^{10}$ can be $N(R^{22})_2$, and $R^3$ and $R^8$ are different and can be selected from the group consisting of hydrogen, N=C=S, $NH_2$, $NHC(O)CH_3$, $NHC(O)CH(CH_3)_2$, NHC($O$)$CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane.

In some embodiments, $R^A$ is $SO_2R^1$, $R^B$ is $SO_2R^{10}$, and at least one of $R^1$ and $R^{10}$ (e.g., one or both) is $N(R^{22})_2$. In some embodiments, at least one of $R^1$ and $R^{10}$ (e.g., one or both) can be $N(R^{22})_2$ and $R^3$ and $R^8$ are selected independently from the group consisting of hydrogen, heterocyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$, wherein $R^{21}$ and $R^{22}$ are independently H or $C_1$-$C_4$ alkyl. For example, at least one (e.g., one or both) of $R^1$ and $R^{10}$ can be $N(R^{22})_2$ and $R^3$ and $R^8$ can be selected independently from the group consisting of hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, benzoxazolyl, or $NHC(O)NH$-cyclopropane.

In some embodiments, $R^A$ is $SO_2R^1$, $R^B$ is $SO_2R^{10}$, and at least one of $R^1$ and $R^{10}$ (e.g., one or both) can be $N(R^{22})_2$, and $R^3$ and $R^8$ are selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. For example, at least one (e.g., one or both) of $R^1$ and $R^{10}$ can be $N(R^{22})_2$, and $R^3$ and $R^8$ are the same and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane. In another non-limiting example, at least one (e.g., one or both) of $R^1$ and $R^{10}$ can be $SO_2R^{21}$ and $R^3$ and $R^8$ are different and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane.

In some embodiments, $R^A$ is $SO_2R^1$, $R^B$ is $SO_2R^{10}$, at least one of $R^1$ and $R^{10}$ is $N(R^{22})_2$, and $R^3$ and $R^8$ are selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. For example, at least one (e.g., one or both) of $R^1$ and $R^{10}$ can be $N(R^{22})_2$, and $R^3$ and $R^8$ are the same and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane. In another non-limiting example, at least one (e.g., one or both) of $R^1$ and $R^{10}$ can be $N(R^{22})_2$, and $R^3$ and $R^8$ are different and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane.

In some embodiments, $R^A$ is $SO_2R^1$, $R^B$ is $SO_2R^{10}$, and at least one of $R^1$ and $R^{10}$ (e.g., one or both) is $OR^{23}$. In some embodiments, at least one of $R^1$ and $R^{10}$ (e.g., one or both) can be $OR^{23}$ and $R^3$ and $R^8$ are selected independently from the group consisting of hydrogen, heterocyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$, wherein $R^{21}$ and $R^{22}$ are independently H or $C_1$-$C_4$ alkyl. For example, at least one (e.g., one or both) of $R^1$ and $R^{10}$ can be $OR^{23}$ and $R^3$ and $R^8$ can be selected independently from the group consisting of hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, benzoxazolyl, or $NHC(O)NH$-cyclopropane.

In some embodiments, $R^A$ is $SO_2R^1$, $R^B$ is $SO_2R^{10}$, and at least one of $R^1$ and $R^{10}$ (e.g., one or both) can be $OR^{23}$, and $R^3$ and $R^8$ are selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. For example, at least one (e.g., one or both) of $R^1$ and $R^{10}$ can be $OR^{23}$, and $R^3$ and $R^8$ are the same and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane. In another non-limiting example, at least one (e.g., one or both) of $R^1$ and $R^{10}$ can be $OR^{23}$ and $R^3$ and $R^8$ are different and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane.

In some embodiments, $R^A$ is $SO_2R^1$, $R^B$ is $SO_2R^{10}$, at least one of $R^1$ and $R^{10}$ is $OR^{23}$, and $R^3$ and $R^8$ are selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. For example, at least one (e.g., one or both) of $R^1$ and $R^{10}$ can $OR^{23}$, and $R^3$ and $R^8$ are the same and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, and $NHC(O)NH$-cyclopropane. In another non-limiting example, at least one (e.g., one or both) of $R^1$ and $R^{10}$ can be $OR^{23}$, and $R^3$ and $R^8$ are different and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, NHC(S)$NHCH_3$, NHC(S)$NHCH(CH_3)_2$, NHC(S)NH-cyclopropane, NHC(O)$NHCH_3$, NHC(O)$NHCH(CH_3)_2$, and NHC(O)NH-cyclopropane.

In some embodiments, $R^A$ $SO_2R^1$, $R^B$ is hydrogen or $SO_2R^{10}$, $R^1$ and $R^{10}$ are $OR^{23}$, and $R^{23}$ is isopropyl or t-butyl.

In some embodiments, one of $R^A$ and $R^B$ is $SO_3Y^+$ and the other is hydrogen or $SO_3Y^+$. In some embodiments, one of $R^A$ and $R^B$ is $SO_3Y^+$ and the other is hydrogen. In some embodiments, one of $R^A$ and $R^B$ is $SO_3Y^+$ and the other is hydrogen or $SO_3^-Y^+$, and $Y^+$ is $Na^+$. In some embodiments, one of $R^A$ and $R^B$ is $SO_3^-Y^+$ and the other is hydrogen or $SO_3^-Y^+$, and $R^3$ and $R^8$ are different.

In some embodiments, one of $R^A$ or $R^B$ is $SO_3Y^+$ and the other is hydrogen or $SO_3^-Y^+$, and $R^3$ and $R^8$ can be selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. In some embodiments, one of $R^A$ or $R^B$ is $SO_3^-Y^+$ and the other is hydrogen or $SO_3^-Y^+$, and $R^3$ and $R^8$ can be selected independently from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, NHC(S)$NHCH_3$, NHC(S)$NHCH(CH_3)_2$, NHC(S)NH-cyclopropane, NHC(O)$NHCH_3$, NHC(O)$NHCH(CH_3)_2$, and NHC(O)NH-cyclopropane.

In one embodiment, one of $R^A$ and $R^B$ is $SO_3^-Y^+$ and the other is hydrogen, $R^3$ is $NHC(O)CH_3$ and $R^8$ is NHC(S)$NHCH(CH_3)_2$.

In some embodiments, one of $R^A$ and $R^B$ is $CO_2^-Y^+$ and the other is hydrogen or $CO_2^-Y^+$.

In some embodiments, $R^A$ and $R^B$ are $CO_2^-Y^+$. In some embodiments, one of $R^A$ and $R^B$ is $CO_2^-Y^+$ and the other is hydrogen or $CO_2^-Y^+$, and $Y^+$ is $Na^+$. In some embodiments, one of $R^A$ and $R^B$ is $CO_2^-Y^+$ and the other is hydrogen or $CO_2^-Y^+$, and $R^3$ and $R^8$ are different.

In some embodiments, one of $R^A$ or $R^B$ is $CO_2^-Y^+$ and the other is hydrogen or $CO_2^-Y^+$, and $R^3$ and $R^8$ can be selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. In some embodiments, one of $R^A$ or $R^B$ is $CO_2^-Y^+$ and the other is hydrogen or $CO_2^-Y^+$, and $R^3$ and $R^8$ can be selected independently from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, NHC(S)$NHCH_3$, NHC(S)$NHCH(CH_3)_2$, NHC(S)NH-cyclopropane, NHC(O)$NHCH_3$, NHC(O)$NHCH(CH_3)_2$, and NHC(O)NH-cyclopropane.

In one embodiment, $R^A$ and $R^B$ are $CO_2^-Y^+$, $R^3$ is NHC(O)$CH_3$ and $R^8$ is NHC(S)$NHCH(CH_3)_2$.

In some embodiments, one of $R^A$ and $R^B$ is $PO_2^-(Y^+)_2$ and the other is hydrogen or $PO_2^-(Y^+)_2$. In some embodiments, $R^A$ and $R^B$ are $PO_2^-(Y^+)_2$. In some embodiments, one of $R^A$ and $R^B$ is $PO_2^-(Y^+)_2$ and the other is hydrogen or $PO_2^-(Y^+)_2$, and $Y^+$ is $Na^+$. In some embodiments, one of $R^A$ and $R^B$ is $PO_2^-(Y^+)_2$ and the other is hydrogen or $PO_2^-(Y^+)_2$, and $R^3$ and $R^8$ are different.

In some embodiments, one of $R^A$ or $R^B$ is $PO_2^-(Y^+)_2$ and the other is hydrogen or $PO_2^-(Y^+)_2$, and $R^3$ and $R^8$ can be selected independently from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. In some embodiments, one of $R^A$ or $R^B$ is $PO_2^-(Y^+)_2$ and the other is hydrogen or $PO_2^-(Y^+)_2$, and $R^3$ and $R^8$ can be selected independently from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, NHC(S)$NHCH_3$, NHC(S)$NHCH(CH_3)_2$, NHC(S)NH-cyclopropane, NHC(O)$NHCH_3$, NHC(O)$NHCH(CH_3)_2$, and NHC(O)NH-cyclopropane.

In one embodiment, $R^A$ and $R^B$ are $PO_2^-(Y^+)_2$, $R^3$ is NHC(O)$CH_3$ and $R^8$ is NHC(S)$NHCH(CH_3)_2$.

In some embodiments, $R^2$-$R^9$ are all different. In some other embodiments, at least two of (e.g., two, three four, five, six or seven of) $R^2$-$R^9$ are same.

In some embodiments, at least one of (e.g., one, two, three, four, five or six of) $R^2$, $R^4$, $R^5$, $R^6$, $R^7$, $R^8$ and $R^6$, and $R^3$ or $R^4$ are the same. In some embodiments, $R^2$ and $R^9$, or $R^4$ and $R^7$, or $R^5$ and $R^6$ are the same. In some embodiments, at least two of $R^2$, $R^4$ and $R^5$ are same. In some embodiments, at least two of $R^6$, $R^7$ and $R^9$ are same.

In some embodiments, $R^2$, $R^4$, $R^5$, $R^6$, $R^7$, $R^8$ and $R^6$ all are different.

In some embodiments, at least one of (e.g., 1, 2, 3, 4, 5, 6, or 7) $R^2$-$R^9$ is hydrogen, hydroxyl, or methoxy. In some embodiments, $R^2$, $R^4$, $R^5$, $R^6$, $R^7$ and $R^9$ are all hydrogen.

The compounds of Formula (I) include pharmaceutically acceptable salts, stereoisomer mixtures, and enantiomers thereof. The compounds of the technology described herein can also include physiologically acceptable salts of the compounds of Formula (I). The compounds of Formula (I) can be present as a racemic mixture or as a substantially pure stereoisomer or enantiomer.

Some exemplary compounds of Formula (I) include, but are not limited to, those shown in Table 1.

TABLE 1

Some exemplary compounds of Formula I

| No. | Compound structure | Compound Name |
|---|---|---|
| 1a (C-1523-1a) | 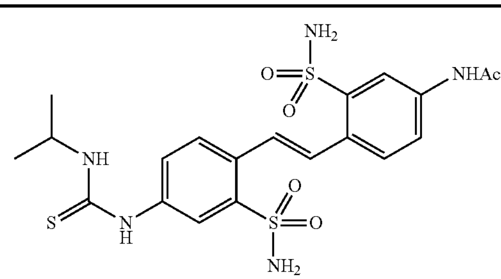 | (E)-N-(4-(4-(3-isopropylthioureido)-2-sulfamoylstyryl)-3-sulfamoylphenyl)acetamide |

TABLE 1-continued

Some exemplary compounds of Formula I

| No. | Compound structure | Compound Name |
| --- | --- | --- |
| 1b-1 (C-1523-1b-1) | 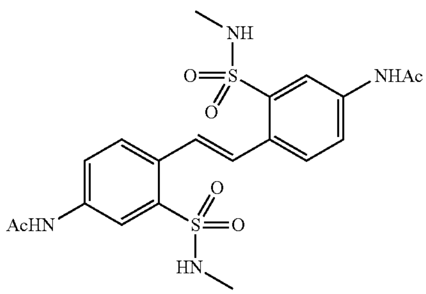 [SMILES: CNS(=O)(=O)c1cc(NC(C)=O)ccc1/C=C/c1ccc(NC(C)=O)cc1S(=O)(=O)NC] | (E)-N,N'-(ethene-1,2-diylbis(3-(N-methylsulfamoyl)-4,1-phenylene))diacetamide |
| 1b (C-1523-1b) | 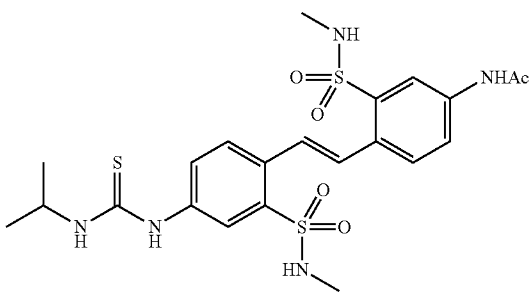 [SMILES: CNS(=O)(=O)c1cc(NC(C)=O)ccc1/C=C/c1ccc(NC(=S)NC(C)C)cc1S(=O)(=O)NC] | (E)-N-(4-(4-(3-isopropylthioureido)-2-(N-methylsulfamoyl)styryl)-3-(N-methylsulfamoyl)phenyl)acetamide |
| 1c (C-1523-1c) | 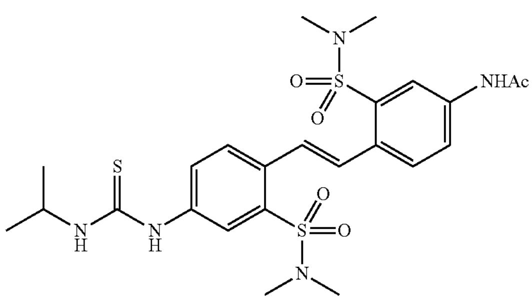 [SMILES: CC(=O)Nc1ccc(/C=C/c2ccc(NC(=S)NC(C)C)cc2S(=O)(=O)N(C)C)c(S(=O)(=O)N(C)C)c1] | (E)-N-(3-(N,N-dimethylsulfamoyl)-4-(2-(N,N-dimethylsulfamoyl)-4-(3-isopropylthioureido)styryl)phenyl)acetamide |
| 1e-1 (C-1523-1e-1) | 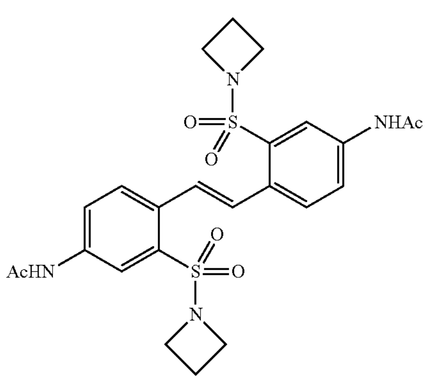 [SMILES: CC(=O)Nc1ccc(/C=C/c2ccc(NC(C)=O)cc2S(=O)(=O)N2CCC2)c(S(=O)(=O)N2CCC2)c1] | (E)-N,N'-(ethene-1,2-diylbis(3-(azetidin-1-ylsulfonyl)-4,1-phenylene))diacetamide |

TABLE 1-continued

Some exemplary compounds of Formula I

| No. | Compound structure | Compound Name |
|---|---|---|
| 1e (C-1523-1e) | 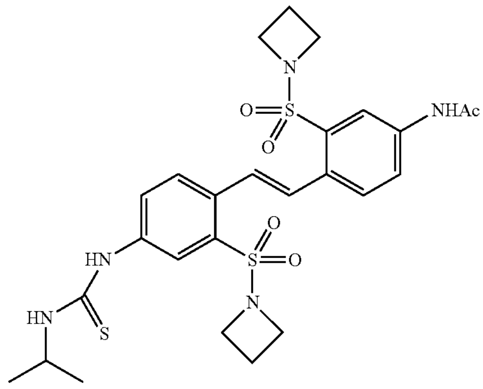 [SMILES: CC(=O)Nc1ccc(/C=C/c2ccc(NC(=S)NC(C)C)cc2S(=O)(=O)N2CCC2)c(S(=O)(=O)N2CCC2)c1] | (E)-N-(3-(azetidin-1-ylsulfonyl)-4-(2-(azetidin-1-ylsulfonyl)-4-(3-isopropylthioureido)styryl)phenyl)acetamide |
| 1d (C-1523-1d) | 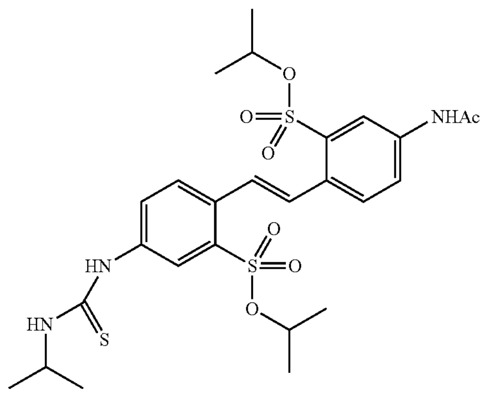 [SMILES: CC(=O)Nc1ccc(/C=C/c2ccc(NC(=S)NC(C)C)cc2S(=O)(=O)OC(C)C)c(S(=O)(=O)OC(C)C)c1] | (E)-isopropyl 5-acetamido-2-(2-(isopropoxysulfonyl)-4-(3-isopropylthioureido)styryl)benzenesulfonate |
| 1f-1 (C-1523-1f-1) | 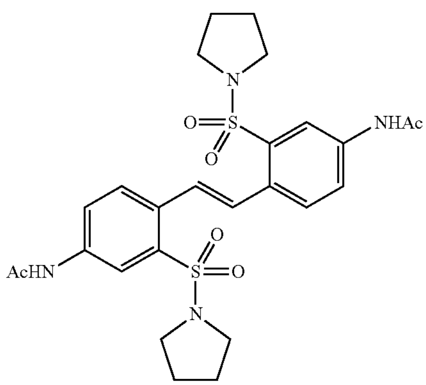 [SMILES: CC(=O)Nc1ccc(/C=C/c2ccc(NC(C)=O)cc2S(=O)(=O)N2CCCC2)c(S(=O)(=O)N2CCCC2)c1] | (E)-N,N'-(ethene-1,2-diylbis(3-(pyrrolidin-1-ylsulfonyl)-4,1-phenylene))diacetamide |
| 1f (C-1523-1f) | 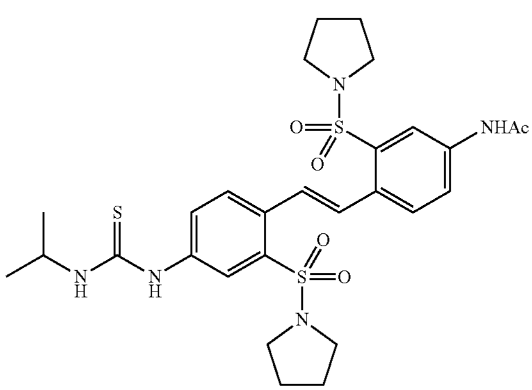 [SMILES: CC(=O)Nc1ccc(/C=C/c2ccc(NC(=S)NC(C)C)cc2S(=O)(=O)N2CCCC2)c(S(=O)(=O)N2CCCC2)c1] | (E)-N-(4-(4-(3-isopropylthioureido)-2-(pyrrolidin-1-ylsulfonyl)styryl)-3-(pyrrolidin-1-ylsulfonyl)phenyl)acetamide |

TABLE 1-continued

Some exemplary compounds of Formula I

| No. | Compound structure | Compound Name |
|---|---|---|
| 2 (C-1523-2) | 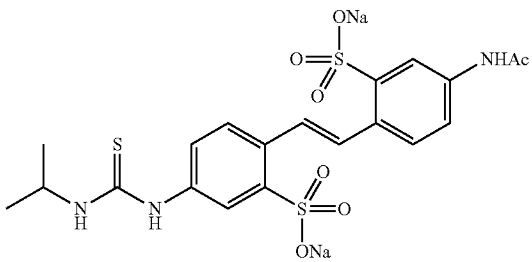 | sodium (E)-5-acetamido-2-(4-(3-isopropylthioureido)-2-sulfonatostyryl)benzenesulfonate |
| 3-1 (C-1523-3-1) | 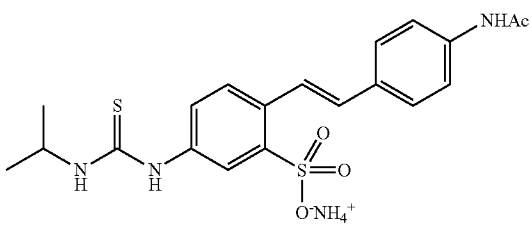 | ammonium (E)-2-(4-acetamidostyryl)-5-(3-isopropylthioureido)benzenesulfonate |
| 4 (C-1523-4) | 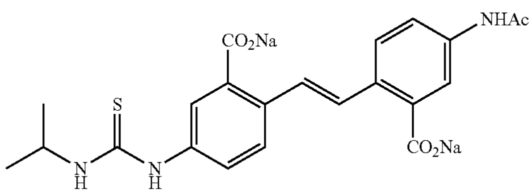 | sodium (E)-5-acetamido-2-(2-carboxylato-4-(3-isopropylthioureido)styryl)benzoate |
| 5 (C-1523-5) | 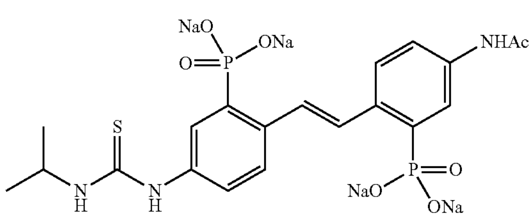 | sodium (E)-5-acetamido-2-(4-(3-isopropylthioureido)-2-sulfonatostyryl)benzenephosphonate |

TABLE 2

| | | |
|---|---|---|
| C-1523-1A | | (E)-5-acetamido-2-(4-(3-isopropylthioureido)-sulfonatostyryl)benzenesulfonamide |

TABLE 2-continued

| | | |
|---|---|---|
| C-1523-1A-D1/ CYT1-02-086-1A (6a) | 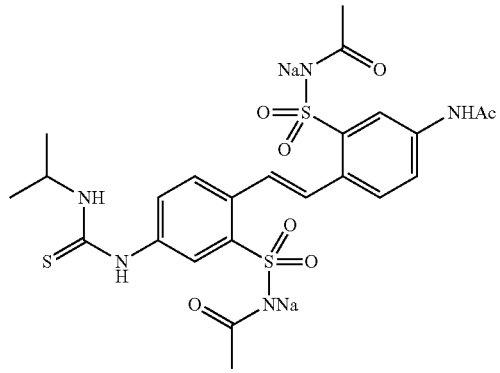 | disodium (E)-N-((5-acetamido-2-(2-(N-acetylsulfamoyl)-4-(3-isopropylthioureido)styryl)phenyl)sulfonyl)acetamide |
| C-1523-1A-D2/ CYT1-02-086-1B (7a) | 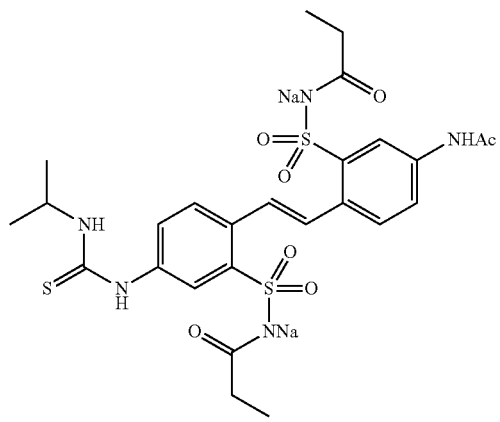 | disodium (E)-((2-(4-acetamido-2-(N-propionylsulfamoyl)styryl)-5-(3-isopropylthioureido)phenyl)sulfonyl)(propionyl)amide |
| C-1523-1A-D3/ CYT1-02-086-1C (8a) | 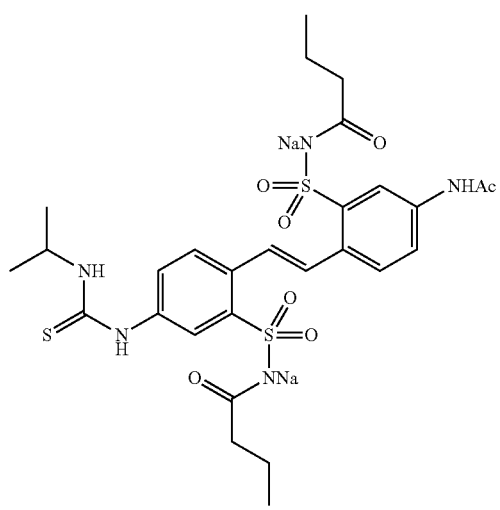 | disodium (E)-((2-(4-acetamido-2-(N-butyrylsulfamoyl)styryl)-5-(3-isopropylthioureido)phenyl)sulfonyl)(butyryl)amide |

TABLE 2-continued

| | | |
|---|---|---|
| C-1523-1A-D4/ CYT1-01-004 (9a) | 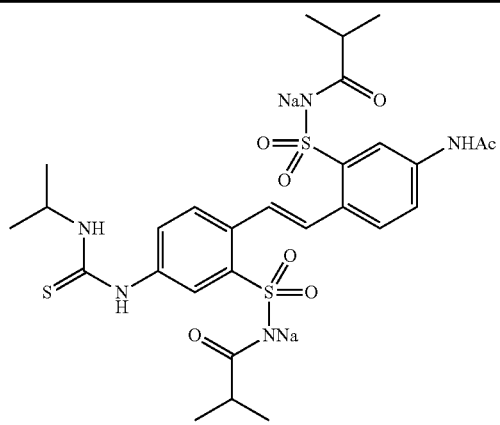 | disodium (E)-((5-acetamido-2-(2-(N-isobutyrylsulfamoyl)-4-(3-isopropylthioureido)styryl)phenyl)sulfonyl)(isobutyryl)amide |

Methods of making stilbenes are well known in the art and are described, for example in U.S. Pat. Nos. 7,321,050; 6,022,998; 6,177,220; 5,068,300; 3,387,050; 5,563,298; 7,820,848; 8,101,804; 6,218,108; and 7,714,161; U.S. Patent Publications 2007/0276172 and 2004/0143023; Likhtenstein, Gertz I. "Stilbenes Synthesis and Applications" in Kirk-Othmer Encyclopedia of Chemical Technology. 2000, John Wiley & Sons, Inc.; Likhtenshtein, G. "Stilbenes Preparation and Analysis" in "Applications in Chemistry, Life Sciences and Materials Science" 2010, Wiley-VCH; which are incorporated by reference herein in their entireties. Synthesis of stilbenes and stilbene derivatives is also available as a commercial service (e.g. Mercachem, Nijmegen, Netherlands; Proteros, Martinsried, Germany; AMRI, Albany, N.Y.; WuXi Apptec, Shanghai, China; and Richman Chemical Inc., Gwynedd, Pa.). In some embodiments, a stilbene may be further functionalized to amide and sulfonamide derivatives.

In some embodiments, relative to DIDS, the compound can comprise a linking double bondm, sulfonates, and asymmetric substituents at the 4- and 4' positions. In some embodiments, the compound does not comprise, relative to DIDS, a proton in place of one or more sulfonates. In some embodiments, relative to DIDS, the compound does not comprise symmetrically substituted groups at the 4 and 4' positions.

In one aspect, described herein is a method of treating cancer, autoimmune disease, immune deficiency, or neurodegenerative disease, the method comprising administering a therapeutically effective dose of a composition as described herein, e.g., a composition comprising a compound having the structure of Formula I, to a subject in need of treatment for cancer, autoimmune disease, immune deficiency, or neurodegenerative disease.

In some embodiments, the subject can be a subject determined to have an increased level of DNA damage occurring in one or more cell types relative to a reference level. As used herein, "DNA damage" refers to breaks, nicks, and mutations of the DNA present in a cell. In some embodiments, the DNA damage can comprise one or more of single-strand breaks (e.g., "nicks"), double strand breaks (DSBs), and mutations. In some embodiments, the DNA damage can be one or more DSBs. As used herein, "mutation" refers to a change or difference in the genetic material of a cell as compared to a reference wildtype cell, e.g. a deletion, an insertion, a SNP, a gene rearrangement, and/or the introduction of an exogenous gene or sequence.

In some embodiments, the subject can be determined to have an increased level of DNA damage if the subject is determined to have an increased level and/or activity of a DNA damage process or DNA editing enzyme. As used herein, "DNA damage process" refers to any activity or process in a cell which causes one or more types of DNA damage to occur.

In some embodiments, an increased level of DNA damage can be an increased level of mutations, e.g., by determining the overall mutation status in all or a portion of the genome of a cell. An overall mutation status at least 2% greater, e.g. 2% greater or more, 3% greater or more, 5% greater or more, 10% greater or more, or 20% greater or more than the overall mutation status in a reference cell can be indicative of an increased, elevated, and/or significant level of a DNA editing enzyme activity. In some embodiments, the level of hyper mutations can be determined. In some embodiments, the overall mutation status in the whole genome or a portion thereof can be determined using FISH, whole genome sequencing, high throughput sequencing, exome sequencing, hybridization, and/or PCR. In some embodiments the activity of a DNA editing enzyme can be measured by determining the level of hypermutations in the specific target genes including, but not limited to IGH, BCL6, MYC, BCL11A, CD93, PIM1 and/or PAX5. In certain embodiments the DNA editing enzyme is AID. In some embodiments, a level of mutation in specific target genes including IGH, BCL6, MYC, BCL11A, CD93, PIM1 and/or PAX5 which is at least 2% greater, e.g. 2% greater or more, 3% greater or more, 5% greater or more, 10% greater or more, or 20% greater or more than the level of mutation in IGH, BCL6, MYC, BCL11A, CD93, PIM1 and/or PAX5 in a reference cell can be indicative of an increased, elevated, and/or significant level of AID activity.

In some embodiments, an increased level of DNA damage can be an increased level of double strand breaks (DSBs). The level of DSBs can be determined, by way of non-limiting example, by karyotyping, by γ-H2AX foci formation, and/or by using FISH analysis to detect DNA double strand breaks, e.g. DNA breakage detection fish (DBD-FISH) (Volpi and Bridger, BioTechniques, Vol. 45, No. 4, October 2008, pp. 385-409).

In some embodiments, an increased level of DNA damage can be an increased level of single strand breaks. The level of single-strand breaks in DNA can be determined, by way of non-limiting example, by COMET assays, FISH, or the use of single-strand break-specific probes. Detection of DNA breaks, both single and double-stranded is known in the art and described further, at, e.g., Kumari et al. EXCLI Journal 2009 7:44-62 and Motalleb et al. Research Journal of Applied Sciences, Engineering and Technology. 2012 4:1888-1894; each of which is incorporated by reference herein in its entirety.

In some embodiments, an increased level or activity of a DNA damage process can comprise an increased level and/or activity of a DNA editing enzyme. In some embodiments, the technology described herein is directed to treating cells having an active DNA editing enzyme with a compound having the structure of Formula I. In some embodiments, the technology described herein is directed to treating cells having an increased level and/or activity of a DNA editing enzyme with a compound having the structure of Formula I. As used herein, "DNA editing enzyme" refers to an enzyme which normally catalyzes the mutation, exchange or excision of DNA segments, particularly enzymes which can generate or promote the generation of point mutations, DNA single strand breaks, DNA double-strand breaks or protein-DNA adducts. A DNA editing enzyme, as referred to herein, is not necessarily site-specific in its action. Similarly, it is not necessarily cell specific. In some embodiments, the cell is a B cell expressing a detectable amount of such an enzyme.

Non-limiting examples of DNA editing enzymes include, but are not limited to Recombination Activating Gene 1 (RAG1; NCBI Gene ID: 5896), Recombination Activating Gene 1 (RAG2; NCBI Gene ID: 5897), Sporulation-specific protein 11 (SPO11; NCBI Gene ID: 23626), APOBEC family members a Type 1 Topoisomerase; a Type 2 Topoisomerase; and/or AID. In some embodiments, the DNA editing enzyme can be AID.

In some embodiments, the DNA editing enzyme can be a member of the APOBEC (apolipoprotein B mRNA editing enzyme, catalytic polypeptide-like) family. As used herein "APOBEC family" refers to a family of cytidine deaminase enzymes having an N-terminal zinc-dependent cytidine deaminase catalytic domain comprising and a C-terminal pseudocatalytic domain. Non-limiting examples of APOBEC family members include AID, APOBEC1 (e.g., NCBI Gene ID: 339), APOBEC2 (e.g., NCBI Gene ID: 10930), APOBEC3A (e.g., NCBI Gene ID: 200315), APOBEC3C (e.g., NCBI Gene ID: 27350), APOBEC3E (e.g., NCBI Gene ID: 140564), APOBEC3F (e.g., NCBI Gene ID:200316), APOBEC3G (e.g., NCBI Gene ID: 60489), APOBEC3H (e.g., NCBI Gene ID: 164668), and APOBEC4 (e.g., NCBI Gene ID: 403314).

In some embodiments, the DNA editing enzyme can be a Type 1 topoisomerase. In some embodiments, the DNA editing enzyme can be a Type 2 topoisomerase. Topoisomerases generate breaks in DNA to help uncoil or relax the strand. Type II topoisomerases hydrolyze ATP to generate DSB cuts, while Type I topoisomerases generate single-stranded breaks. Non-limiting examples of Type II topoisomerases can include topoisomerase II (e.g., NCBI Gene ID: 7153 and 7155). Non-limiting examples of Type I topoisomerases can include topoisomerase I (e.g., NCBI Gene ID: 7150).

Embodiments of the technology described herein are based on the discovery that the compounds described herein can inhibit DNA repair mechanisms, e.g., homologous repair. Activation-induced cytidine deaminase (AID, or AICDA, also known as ARP2, CDA2 or HIGM2), a DNA-editing enzyme that is a member of the apolipoprotein B mRNA editing enzymes, catalytic polypeptide-like (APOBEC), will cause widespread genomic breaks and cell death in cells with diminished homologous recombination ability (e.g. cells with diminished DNA double strand break repair abilities). Accordingly, provided herein is a method of causing cell death comprising detecting increased expression of a DNA-editing enzyme (e.g. AID) in a cell and thereafter contacting the cell with a compound having the structure of Formula I; thereby resulting in cell death. Accordingly, provided herein is a method of causing cell death comprising increasing expression of a DNA-editing enzyme (e.g. AID) in a cell and thereafter contacting the cell with a compound having the structure of Formula I; thereby resulting in cell death. Accordingly, provided herein is a method of causing cell death comprising administering to a cell a therapeutically effective amount of a DNA editing enzyme (e.g. AID) and thereafter contacting the cell with a compound having the structure of Formula I; thereby resulting in cell death.

AID, encoded by the AICDA gene (NCBI Gene ID: 57379), is required for proper B-cell function and is most prominently expressed in centroblast B-cells. The protein is involved in somatic hypermutation, gene conversion, and class-switch recombination of immunoglobulin genes. AID is normally expressed almost exclusively in antigen-activated germinal center B-cells, where it initiates immunoglobulin isotype class switching (Manis et al. 2002, Trends Immunol, 23, 31-39; Chaudhuri and Alt, Nat Rev Immunol, 2004, 4, 541-552; Longerich et al., Curr Opin Immunol, 2006, 18, 164-174; Chaudhuri et al., Adv Immunol 2007, 94, 157-214). AID is required for somatic hypermutation and immunoglobulin class switching in activated B cells. AID expression is regulated by CD40 ligand, B-cell receptor, IL4R, or Toll-like receptor stimulation (Crouch et al., J Exp Med 2007 204:1145-1156; Muramatsu et al., J Biol Chem 1999 274:18470-6). After activation, AID is transiently upregulated, induces point mutations or DNA double strand breaks in a sequence non-specific manner within immunoglobulin genes, and is then downregulated (Longerich et al., Curr Opin Immunol, 2006, 18, 164-176; Chaudhuri et al., Adv Immunol 2007, 94, 157-214). Overall, AID is active in only a tiny population of normal cells (antigen-activated B-cells) at any given time. The genomic rearrangements and mutations controlled by AID lead to the development of antigen-recognition diversity, receptor editing and lymphoid effector function required for functional adaptive immunity (Mills, et al. Immunol Rev 2003 194:77-95). Recently it has been reported that AID has off-target point mutation activities (Liu, M. et al., Nature 2008, 451, 841-845; Liu and Schatz, Trends Immunol. 2009, 30, 173-181; Perez-Duran et al., Carcinogenesis. 2007, 28(12):2427-33). Robbiani et al. has reported off-target activities of AID in B-cells, especially c-myc/IgH translocations (Robbiani et al., Mol Cell 2009, 36(4):631-41). AID expression accelerates the rate of tumor development in Bcl6 transgenic mice (Pasqualucci et al., 2008, Nat. Genet. 40, 108-112). However, deregulated AID does not necessarily cause malignancy or translocation-associated cancer on its own in B cells (Muto et al., 2006, Proc. Natl. Acad. Sci. USA 103, 2752-2757; Okazaki et al., 2003, J. Exp. Med. 197, 1173-1181; Shen et al., 2008, Mol. Immunol. 45, 1883-1892). In addition, despite its obligate role in c-myc/IgH translocation, AID is not required for the development of plasmacytosis or plasmacytoma in IL-6 transgenic or pristane-treated mice, respectively (Kovalchuk et al., 2007, J. Exp. Med. 204, 2989-3001; Ramiro et al., 2004, J. Exp. Med. 200, 1103-1110). However, most human B cell lymphoma-associated translocations do not involve c-myc, and many do not involve Ig genes (Kuppers, 2005, Oncogene 20, 5580-5594).

Overexpression of AID has been reported in chronic lymphocytic leukemia (CLL) (Hancer et al. Leuk Lymphoma. 2011 January; 52(1):79-84; Heintel et al., Leukemia. 2004 April; 18(4):756-62). Further, AID expression has been shown to be correlated with blast crisis B lineage leukemia and therapy resistance in myeloid leukemia and to be associated with generally poor prognosis in chronic B lymphocytic leukemia (Mao et al., Br J Dermatol 2001, 145: 117-122; Chaudhuri et al., Nature 2004, 430:992-8). Further expression of AID in tumor cells from a variety of cancers has been reported including but not limited to lung, breast, gastric, colon, intestinal, liver cancer and choriangiocarcinoma (Greeve et al., Blood 2003, 1010, 3574-3580; Feldhahn et al., J Exp Med 2007, 204, 1157-1166; Kotani et al., PNAS USA 2007, 104, 1616-1620; Engels et al., 2008, Appl Immunohistochem Mol Morphol 16, 521-529; Klemm et al., 2009, Cancer Cell 6, 232-245; Palacios et al., 2010, Blood 115(22), 4488-4496; Leuenberger et al., 2009, Mod Pathol 32, 177-186; Gruber et al., 2010, Cancer Res 70, 7411-7420; inflammatory cancer (Marusawa 2008, Int J Biochem Cell Biol. 40, 399-402); follicular lymphoma (Hardianti et al., 2004, Leukemia 18, 826-831; Shikata et al., 2012, Cancer Sci. 103(3):415-21); thyroid cancer (Qiu et al. 2012, Mod Pathol 25(1),36-45); breast cancer (Borchert et al. 2011, BMC Cancer 11:347); Marusawa, et al., 2011, Adv Immunol 111:109-41; Zhang et al. 2012, Hum Pathol 43(3):423-34; Komori et al., 2008, Hepatology 47(3):888-896; Hockley 2010, Leukemia 24(5):1084-6; adult T-cell leukemia (Nakamura et al., 2011, Br J Dermatol. 165(2):437-9). All of the references in the foregoing paragraph are incorporated by reference herein in their entireties.

Elevated levels of AID have been reported in arthritis (Xu et al. Scand. J. Immunol. 2009, 296, 2033-6) and in the MRL/Fas(lpr/lpr) mouse lupus model (White et al. 2011, Autoimmunity 44(8), 585-98). All of the references in the foregoing paragraph are incorporated by reference herein in their entireties.

When DSB repair is inhibited, the extent of the DSBs generated by AID is much higher than previously suspected and the extent of genomic damage is so severe as to result in cell death. Accordingly, in one embodiment of the technology described herein, there is provided a method of treatment comprising; (a) selecting a subject having cells that express elevated levels of activation-induced cytidine deaminase (AID); and (b) administering a therapeutically effective amount of an inhibitor of double strand break repair (e.g. a compound having the structure of Formula I) to the subject; wherein an elevated level of AID is a level of AID that is higher than the level of AID in cells of the same type from a healthy individual. In some embodiments, the cells expressing elevated levels of AID are B cells. In some embodiments, the B cell expressing elevated levels of AID is a cancerous B cells or a B cell associated with autoimmune disease. In some embodiments, the subject can be a human subject.

Methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g. cancerous B cells and/or autoimmune cells. Accordingly, as described herein, in one embodiment there is a provided a treatment paradigm that selectively induces self-destruction of certain diseased cells, while reducing the unintended side effects in healthy tissues.

In some embodiments, an increased level and/or activity of a DNA editing enzyme can be an increased level of DNA editing enzyme mRNA. mRNA levels can be assessed using, e.g., biochemical and molecular biology techniques such as Northern blotting or other hybridization assays, nuclease protection assay, reverse transcription (quantitative RT-PCR) techniques, RNA-Seq, high throughput sequencing and the like. Such assays are well known to those in the art. In one embodiment, nuclear "run-on" (or "run-off") transcription assays are used (see e.g. Methods in Molecular Biology, Volume: 49, Sep. 27, 1995, Page Range: 229-238). Arrays can also be used; arrays, and methods of analyzing mRNA using such arrays have been described previously, e.g. in EP0834575, EP0834576, WO96/31622, U.S. Pat. No. 5,837,832 or WO98/30883. WO97/10365 provides methods for monitoring of expression levels of a multiplicity of genes using high density oligonucleotide arrays.

In one embodiment, one or more cells from the subject to be tested are obtained and RNA is isolated from the cells. When obtaining the cells, it is preferable to obtain a sample containing predominantly cells of the desired type, e.g., a sample of cells in which at least about 50%, preferably at least about 60%, even more preferably at least about 70%, 80% and even more preferably, at least about 90% of the cells are of the desired type. Tissue samples can be obtained according to methods known in the art.

It is also possible to obtain a cell sample from a subject, and then to enrich it in the desired cell type. For example, cells can be isolated from other cells using a variety of techniques, such as isolation with an antibody binding to an epitope on the cell surface of the desired cell type. Where the desired cells are in a solid tissue, particular cells can be dissected out, e.g., by microdissection, or laser capture microdissection (LCM).

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly-become degraded. Accordingly, in a preferred embodiment, the tissue or cells obtained from a subject is snap frozen or treated with RNAlater as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190: 199. Care to avoid RNA degradation must be taken, e.g., by inclusion of RNAsin.

The RNA sample can then be enriched in a particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the QuickExtract® kit (Epicentre Biotechnologies, Madison, Wis.; Oligotex Direct mRNA kit, Qiagen, Valencia, Calif.).

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize mRNA transcripts of a regulatable protein, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the gene encoding the protein to be assayed. As herein used, the term "stringent conditions" means hybridization will occur only if there is at least 95% identity in nucleotide sequences. In another embodiment, hybridization under "stringent conditions" occurs when there is at least 97% identity between the sequences.

In some embodiments, an increased level and/or activity of a DNA editing enzyme can be an increased level of a DNA editing enzyme polypeptide. The level of protein expressed from a gene can be assessed, for example by Western blotting, by an immunological detection of the protein, ELISA (enzyme-linked immunosorbent assay), radioimmunoassay (RIA) or other immunoassays and fluorescence-activated cell analysis (FACS), mass spectrometry, or protein sequencing to detect protein.

In some embodiments, a subject can be determined to have an increased level of DNA damage occurring in one or more cell types relative to a reference level if the subject has been exposed to an agent that is known to cause such DNA damage. Non-limiting examples of such agents can include a viral infection with a DNA integrating virus (e.g. adeno-associated virus, retrovirus, human T-lymphotropic virus, HIV-1, oncovirus, hepatitis virus, hepatitis B virus); DNA damaging chemicals (e.g. acetalaldehyde, polycyclin aromatic hydrocarbons, benzenes, nitrosamines, tobacco smoke, alflatoxin, and the like); DNA damaging chemotherapeutic agents (e.g. bleomycin, mitomycin, nitrogen mustards (e.g. mechlorethamine, cyclophosphamide, melphalan, chlorambucil, ifosfamide and busulfan), nitrosoureas (e.g., N-Nitroso-N-methylurea (MNU), carmustine (BCNU), lomustine (CCNU) and semustine (MeCCNU), fotemustine and streptozotocin), tetrazines (e.g., dacarbazine, mitozolomide and temozolomide), aziridines (e.g., thiotepa, mytomycin and diaziquone (AZQ)), cisplatins (e.g., cisplatin, carboplatin and oxaliplatin) procarbazine and hexamethylmelamine); and ionizing or ultraviolet radiation. Exposure to such agents can be the result of an accident, infection and/or environmental exposure or the result of a therapeutic administration of such agents.

In some embodiments, the increased level of DNA damage can be occurring in a cell type affected by the cancer, autoimmune disease, and/or neurodegenerative disease. In some embodiments, the subject is determined to have an increased level of DNA damage occurring in a cell selected from the group consisting of: a cancer cell; an immune system cell; or a nervous system cell.

In some embodiments, the DNA editing enzyme can be AID. In some embodiments, the level of AID can be the level of AID in a blood cell. In some embodiments, the level of AID can be the level of AID in a B cell.

In some embodiments, an increased level of AID can be a detectable level of AID, e.g., as described below herein.

In some embodiments, an increased level of AID is a level of AID which is statistically significantly higher than the level of AID expressed in unactivated B cells, e.g., unactivated B cells from the same subject or a healthy subject. In some embodiments, an increased level of AID is a level of AID which is statistically significantly higher than the level of AID expressed in a normal non-immune cell from the same subject. In some embodiments, an increased level of AID is a level of AID which is statistically significantly higher than the level of AID expressed in a normal non-immune cell from a healthy subject.

In some embodiments, the levels of a DNA editing enzyme in the cells expressing an elevated level of a DNA editing enzyme are significantly higher than normal cells from a healthy subject. In some embodiments, the levels of a DNA editing enzyme in the cells expressing an elevated level of a DNA editing enzyme are significantly higher than the levels of a DNA editing enzyme expressed in unactivated B cells from a healthy subject. In some embodiments, the levels of a DNA editing enzyme in the B cells expressing an elevated level of a DNA editing enzyme are significantly higher than the levels of AID expressed in unactivated B cells from a healthy subject.

In some embodiments, the subject can be a human subject.

Methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g. cancerous B cells and/or autoimmune cells. Accordingly, as described herein, in one embodiment there is a provided a treatment paradigm that selectively induces self-destruction of certain diseased cells, while reducing the unintended side effects in healthy tissues.

In some embodiments, an increased level and/or activity of a DNA editing enzyme can be an increased level of DNA editing enzyme mRNA. mRNA levels can be assessed using, e.g., biochemical and molecular biology techniques such as Northern blotting or other hybridization assays, nuclease protection assay, reverse transcription (quantitative RT-PCR) techniques, RNA-Seq, high throughput sequencing and the like. Such assays are well known to those in the art. In one embodiment, nuclear "run-on" (or "run-off") transcription assays are used (see e.g. Methods in Molecular Biology, Volume: 49, Sep. 27, 1995, Page Range: 229-238). Arrays can also be used; arrays, and methods of analyzing mRNA using such arrays have been described previously, e.g. in EP0834575, EP0834576, WO96/31622, U.S. Pat. No. 5,837,832 or WO98/30883. WO97/10365 provides methods for monitoring of expression levels of a multiplicity of genes using high density oligonucleotide arrays.

In one embodiment, one or more cells from the subject to be tested are obtained and RNA is isolated from the cells. When obtaining the cells, it is preferable to obtain a sample containing predominantly cells of the desired type, e.g., a sample of cells in which at least about 50%, preferably at least about 60%, even more preferably at least about 70%, 80% and even more preferably, at least about 90% of the cells are of the desired type. Tissue samples can be obtained according to methods known in the art.

It is also possible to obtain a cell sample from a subject, and then to enrich it in the desired cell type. For example, cells can be isolated from other cells using a variety of techniques, such as isolation with an antibody binding to an epitope on the cell surface of the desired cell type. Where the desired cells are in a solid tissue, particular cells can be dissected out, e.g., by microdissection, or laser capture microdissection (LCM).

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly-become degraded. Accordingly, in a preferred embodiment, the tissue or cells obtained from a subject is snap frozen or treated with RNAlater as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190: 199. Care to avoid RNA degradation must be taken, e.g., by inclusion of RNAsin.

The RNA sample can then be enriched in a particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the QuickExtract® kit (Epicentre Biotechnologies, Madison, Wis.; Oligotex Direct mRNA kit, Qiagen, Valencia, Calif.).

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize mRNA transcripts of a regulatable protein, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the gene encoding the protein to be assayed. As herein used, the term "stringent conditions" means hybridization will occur only if there is at least 95% identity in nucleotide sequences. In another embodiment, hybridization under "stringent conditions" occurs when there is at least 97% identity between the sequences.

Also provided herein are methods for determining if a condition in a subject, e.g. a cancer, neurodegenerative disease, or autoimmune disease, will be responsive to treatment by an a compound having the structure of Formula I by determining the level of a DNA editing enzyme (e.g. AID) protein, mRNA and/or activity in the cells of that subject. The presence of high levels of a DNA editing enzyme in the subject's cells (test sample) can be indicative that the subject will be responsive to treatment by a compound having a structure of Formula I. The level of a DNA editing enzyme can be determined by assessing the level in a biological sample obtained from a subject and comparing the observed levels to the levels of a DNA editing enzyme found in a control reference sample. In some embodiments the DNA editing enzyme is AID.

In one embodiment, the condition (e.g. cancer or autoimmune disease) to be treated is already known to those of skill in the art to have high levels of a DNA editing enzyme, and thus treatment with an inhibitor of DSB repair is indicated without the need to measure levels of a DNA editing enzyme protein, mRNA, and/or expression in a biological sample obtained from the patient. In certain embodiments the DNA editing enzyme is AID.

As used herein, a "biological sample" refers to a sample of biological material obtained from a patient, preferably a human patient, including a tissue sample (e.g., a tissue biopsy, such as, an aspiration biopsy, a brush biopsy, a surface biopsy, a needle biopsy, a punch biopsy, an excision biopsy, an open biopsy, an incision biopsy or an endoscopic biopsy) or cell samples (e.g. epithelial cells or lymphocytes). Biological samples can also be biological fluid samples e.g. semen, urine, blood, serum, saliva, cerebrospinal fluid, and supernatant from cell lysate, e.g. lymphocyte fraction. Some embodiments of the technology described herein also encompass the use of isolates of a biological sample in the methods described herein.

In some embodiments, a control and/or reference level can be the level in a healthy individual or population of individuals. In some embodiments, a control and/or reference level can be the level in a healthy cell or population of healthy cells of the same type. In some embodiments, the control and/or reference level can be the level in a control and/or reference sample. The control and/or reference sample can be a biological sample (of the same type) that is obtained from a healthy individual, i.e. an individual that does not have cancer or an autoimmune disease. The control reference sample can also be a standard sample that contains the same concentration of a DNA editing enzyme that is normally found in a biological sample of the same type and that is obtained from a healthy individual. For example, there can be a standard reference control sample for the amounts of a DNA editing enzyme normally found in biological samples such as particular cell fractions (e.g. lymphocytes), semen, urine, blood, cerebral spinal fluid, or tissue. In one embodiment, the control reference sample is a standard reference sample that contains a mean or median concentration of a DNA editing enzyme mRNA or a DNA editing enzyme protein found in cells from a population of healthy individuals that do not have cancer or an autoimmune disease. In one embodiment, e.g., when the cells are B cells, the reference level is the level of a DNA editing enzyme protein or mRNA found in a population of unactivated B-lymphocytes from a healthy individual. In one embodiment, the control reference sample is a biological sample of the patient from healthy cells or tissue from the patient, e.g. if the patient has lymphoma, a cheek swab or skin biopsy can be used as a reference sample. In some embodiments, the levels of a DNA editing enzyme mRNA, protein, and/or activity found in a population of B-cells undergoing class switching are not suitable control reference samples.

Cells obtained from a subject are characterized as having increased, or elevated levels of a DNA editing enzyme protein and/or mRNA if the level of a DNA editing enzyme protein, a DNA editing enzyme mRNA, and/or a DNA editing enzyme activity detected in the subject's cells (e.g. a biological sample comprising cancerous or autoimmune cells), is higher by a statistically significant amount, than the level of a DNA editing enzyme protein, mRNA and/or activity found in a reference control sample representative of the level of a DNA editing enzyme in cells of the same type from a healthy subject. The levels of a DNA editing enzyme can be represented by arbitrary units, for example as units obtained from a densitometer, luminometer, or an ELISA plate reader etc.

As used herein, the terms, a "high level" an "elevated level", and/or "increased level" of a DNA editing enzyme protein, mRNA, and/or activity are used interchangeably and refer to amounts of a DNA editing enzyme protein, mRNA, and/or activity that are significantly greater than the amounts of a DNA editing enzyme protein, mRNA, and/or activity present in a control reference sample representative of the levels of a DNA editing enzyme in cells of the same type from a healthy individual.

In some embodiments, the control reference sample can comprise healthy cells of the same type as the cells for which a DNA editing enzyme levels are to be determined. In some embodiments, the cells of the control reference sample can be of similar age, developmental status, sex, and/or cell type as the cells for which the level of a DNA editing enzyme expression is to be determined. In some embodiments, the control reference sample can be obtained from a healthy organism of similar age, developmental status, and/or sex as the subject organism for which the level of a DNA editing enzyme expression is to be determined. In some embodiments, the test sample and control reference sample are of the same type, that is, obtained from the same biological source, and comprising the same composition, e.g. the same number and type of cells.

In some embodiments, the control reference sample can comprise healthy, unactivated and/or non-transformed B cells. In some embodiments, an elevated level of a DNA editing enzyme is a level significantly greater than that in a healthy, unactivated and/or non-transformed B cell. In some embodiments, B-cells undergoing class-switching are not considered to be useful reference samples. In a certain embodiment the DNA editing enzyme is AID.

In most normal cells AID protein/mRNA are not detectable, therefore in some embodiments, mere detection of AID can be considered to be an increased level as compared to there being no detectable levels in cells from a healthy individual. In some embodiments, an elevated level of AID can be the level of AID which is detectable using an RT-PCR assay.

In some embodiments, a detectable level of AID can be 1 pg of AID mRNA per 1 mL of blood or more, e.g. 10 pg/mL, 100 pg/mL, 1 ng/mL, 10 ng/mL or more. In some embodiments, a detectable level of AID can be 10 pg of AID mRNA per 1 mL of blood or more. In some embodiments, a detectable level of AID can be 100 pg of AID mRNA per 1 mL of blood or more. In some embodiments, a detectable level of AID can be 1 ng of AID mRNA per 1 mL of blood or more. In some embodiments, a detectable level of AID can be 10 ng of AID mRNA per 1 mL of blood or more. In some embodiments, a detectable level of AID can be 100 ng of AID mRNA per 1 mL of blood or more.

In some embodiments, a detectable level of AID can be 5 copies (e.g. transcripts) of AID mRNA per cell or more, e.g. 10 copies, 100 copies, 1,000 copies or more per cell.

In some embodiments, a detectable level of AID can be, as measured by immunohistochemistry, 1 AID polypeptide per 20 square microns in a tissue section or more e.g. 1 polypeptide, 10 polypeptides, 100 polypeptides, 1,000 polypeptides or more per 20 square microns in a tissue section.

In some embodiments, a detectable level of AID can be 0.1 pg of AID polypeptide per mL of blood or serum or more, e.g. 0.1 pg, 1 pg, 10 pg, 100 pg, 1 ng, 10 ng, or more per mL of blood. In some embodiments, a detectable level of AID can be 0.1 pg or more of AID polypeptide per mL of blood or serum. In some embodiments, a detectable level of AID can be 10 pg or more of AID polypeptide per mL of blood. In some embodiments, a detectable level of AID can be 100 pg or more of AID polypeptide per mL of blood. In some embodiments, a detectable level of AID can be 1 ng or more of AID polypeptide per mL of blood. In some embodiments, a detectable level of AID can be 10 ng or more of AID polypeptide per mL of blood. In some embodiments, a detectable level of AID can be 100 ng or more of AID polypeptide per mL of blood.

In some embodiments, a sample comprising serum can first be depleted of serum albumin to increase sensitivity. In some embodiments, a sample comprising blood can be enriched for B-cells or for cancerous cells before detecting the level of a DNA editing enzyme. In some embodiments, numeric expression values can be quantified and analyzed with software (e.g., Microsoft EXCEL® spreadsheet and Affymetrix GENECHIP® software).

In some embodiments, a subject is a candidate for treatment according to the methods described herein if the levels of a DNA editing enzyme in the cells of a subject are significantly greater than the levels of DNA editing enzyme present in the control reference sample. In some embodiments, a subject is a candidate for treatment according to the methods described herein if the levels of DNA editing enzyme in the cells of a subject are at least 1.5-fold, 2-fold, 5-fold, 10-fold greater than the levels of DNA editing enzyme present in the control reference sample, e.g. 1.5-fold or greater, 2-fold or greater, 3-fold or greater, 4-fold or greater, 5-fold or greater, or 6-fold or greater.

In some embodiments, a healthy subject and/or a subject not in need of treatment according to the methods described herein can be one whose cells do not express a detectable level of a DNA editing enzyme. In some embodiments, the DNA editing enzyme can be AID.

The technology described herein can relate to the use of at least one compound having the structure of Formula I and compositions comprising at least one compound having the structure of Formula I for the treatment of a cancer having increased levels of DNA damage and/or increased levels and/or activity of a DNA editing enzyme (e.g. increased AID protein or mRNA). For example, a composition containing a compound having the structure of Formula I is used to reduce the tumor size, tumor growth, cancer cell count, cancer cell expansion or metastasis of a cancer. For example, a composition containing a compound having the structure of Formula I is used to reduce the severity, duration, or number of symptoms associated with one of the following, which are offered by way of example only; a B-cell cancer, a leukemia, a lymphoma, a colon cancer, a liver cancer, a gastric cancer, an intestinal cancer, a breast cancer, a lung cancer, a thyroid cancer, a brain cancer, a renal cancer, a melanoma, a prostate cancer or a cholangiocarcinoma. The technology described herein can also relate to the use of at least one compound having the structure of Formula I to increase life expectancy or increase time to remission in patients treated with the compound as compared to patients not treated with the compound.

As described above herein, some embodiments of the invention relate to methods of treatment comprising (a) selecting a subject having cells that have increased DNA damage and/or increased levels and/or activity of DNA editing enzyme, e.g. activation-induced cytidine deaminase (AID); and (b) administering a therapeutically effective amount of a compound having the structure of Formula I to the subject. Some embodiments of the invention relate to methods of treatment comprising (a) selecting a subject having cells that express an elevated level of DNA editing enzyme, e.g. activation-induced cytidine deaminase (AID); and (b) administering a therapeutically effective amount of a compound having the structure of Formula I to the subject wherein an elevated level of a DNA editing enzyme is a level of a DNA editing enzyme that is higher than the level of a DNA editing enzyme in cells of the same type from a healthy individual.

In some embodiments, the methods of treatment comprise (a) selecting a subject having B cells that express a DNA editing enzyme; and (b) administering a therapeutically effective amount of a compound having the structure of Formula I to the subject. In some embodiments, the methods of treatment comprise (a) selecting a subject having B cells that express an elevated level of a DNA editing enzyme; and (b) administering a therapeutically effective amount of a compound having the structure of Formula I to the subject; wherein an elevated level of a DNA editing enzyme is a level of a DNA editing enzyme that is higher than the level of a DNA editing enzyme in B cells from a healthy individual. In some embodiments, the cells that express a DNA editing enzyme are cancerous cells. In some embodiments, the B cells that express a DNA editing enzyme are cancerous cells. In some embodiments the DNA editing enzyme is AID. As used herein, the term "cancerous cell" refers to cells that proliferate in an unregulated manner. In some embodiments, a subject having cancerous B cells that express elevated levels of a DNA editing enzyme can be a subject having or diagnosed as having a B-cell cancer (e.g. B cell lymphoma or leukemia), as described below herein. In some embodiments the high level of a DNA editing enzyme is detected in blood, serum or a biopsy sample.

In certain embodiments, the methods described herein selectively treat B-cell neoplasms, lymphomas, and leukemias by exploiting recombination and DNA repair systems to induce tumor cell self-destruction. This approach takes advantage of the finding that the DNA editing enzyme induces widespread genomic breaks and cell death in primary B-cells with diminished homologous recombination ability. As described herein, the inventors have determined that where a population of cells characterized by increased DNA damage and/or an increased level and/or activity of a DNA editing enzyme (e.g. increased expression of AID) is treated with a compound as described herein, cell death results. Accordingly, provided herein are methods for treating patients with cancer, e.g., patients with cancer having increased levels of DNA damage and/or increased levels and/or activity of a DNA editing enzyme with a compound as described herein.

In certain embodiments, the cancer to be treated is a type with high expression of a DNA editing enzyme. In certain embodiments, the cancer to be treated is a B-cell neoplasm. In certain embodiments, the cancer to be treated is a lymphoma.

In certain embodiments, the cancer to be treated is Burkitt's lymphoma, follicular lymphoma, MALT lymphoma, multiple myeloma, small lymphocytic lymphoma, lymphoplasmacytic lymphoma, plasma cell myeloma, large B-cell lymphoma and/or T-cell lymphoma. Lymphoma is a malignancy in the lymphatic cells of the immune system (e.g. B cells, T cells, or natural killer (NK) cells). Lymphomas often originate in the lymph nodes and present as solid tumors. They can metastasize to other organs such as the brain, bone, or skin. Extranodal sites are often located in the abdomen. Lymphomas are closely related to the lymphoid leukemias and in some cases a particular form of cancer is categorized as both a lymphoma and a leukemia.

Several classification systems exist for lymphomas with the most recent being the World Health Organization classification developed in 2001 and updated in 2008 (Jaffe, E. S., et al., (Eds.) World Health Organization Classification of Tumors, Pathology and Genetics of tumors of hematopoietic and lymphoid tissues IARC Press: Lyon, France 2001). The WHO system divides lymphomas into three primary categories; mature B-cell lymphomas, mature T-cell lymphomas and mature NK cell lymphomas. Included in separate categories are Hodgkin lymphomas (comprised of abnormal B cells) and a number of other less common lymphomas.

Lymphoma can be diagnosed by a biopsy. Tissue obtained from the biopsy is subjected to histological examination to determine the presence, type, and arrangement of malignant cells. The cells are also tested to determine if they are lymphocytes and if so, what type of lymphocyte. Additional tests to determine the scope of the lymphoma and where it is located in the body can include additional biopsies, nuclear medicine, X-rays, CT scans or MRI (see US Patent Publication US2003/0129665). Hodgkin's lymphoma can be diagnosed by the presence of Reed-Sternberg cells in addition to other abnormal cell patterns characteristic of the disease. Markers and histological signs that differentiate each type of lymphoma are known to those skilled in the art (Jaffe, E. S., et al. (Eds.) World Health Organization Classification of Tumors, Pathology and Genetics of tumors of hematopoietic and lymphoid tissues IARC Press: Lyon, France 2001).

In certain embodiments the cancer to be treated is a leukemia. Leukemias are malignant neoplasms of hematopoietic tissues. Leukemias are categorized into two predominant forms: chronic and acute. Acute leukemia is characterized by the rapid increase of immature blood cells, which impairs the ability of the bone marrow to produce healthy blood cells. Chronic leukemia is characterized by the build up of relatively mature, yet abnormal, white blood cells. Abnormal cells are produced at a much higher rate than normal cells and result in the accumulation of abnormal white blood cells in the blood. Notwithstanding these classifications, however, the pathological impairment of normal hematopoiesis is the hallmark of all leukemias.

Further, leukemias are subdivided according to which blood cell is affected. For example, leukemias can be divided into lymphoblastic or lymphocytic leukemias and myeloid or myelogenous leukemias. In lymphoblastic or lymphocytic leukemias, a pre-lymphocyte cell is typically affected, which impairs the infection-fighting properties of cells derived from lymphocytes. Most lymphocytic leukemias involve B cells, a specific subtype of lymphocyte. In myeloid or myelogenous leukemias, white blood cell precursors are often affected as are some other types of red cells, and platelets. Thus, leukemias can be generally subdivided into four categories: acute lymphoblastic leukemia (ALL), chronic lymphocytic leukemia (CLL), and chronic myelogeneous leukemia (CML). Specific manifestations of each subtype can involve B cells. In some embodiments, the term leukemia includes Burkitt's leukemia; chronic lymphocytic leukemia (CLL), acute myelogenous leukemia (AML); B-cell acute lymphocytic leukemia (B-ALL) and T-cell acute lymphoblastic leukemia (T-ALL). In one embodiment, the term leukemia as described herein also encompasses hairy cell leukemia, which is often considered to be outside of the above-described classification scheme.

Leukemias can be diagnosed by any method known in the art. Typically, a complete blood count (CBC) test is initially performed. A CBC counts the number of white blood cells, red blood cells, and platelets in a blood sample. A sample of blood with high numbers of white blood cells and low levels of red blood cells or platelets can indicate leukemia, and abnormal liver and kidney function tests will indicate if the leukemia has affected those organs. Flow cytometry can also be used for a more precise diagnosis, for example, by using mature myeloid markers such as CD11b and Gr-1 to determine cell type, cell number, and/or cell morphology. Markers and histological signs that differentiate each type of cancer are known to those skilled in the art (Jaffe, E. S., et al. (Eds.) World Health Organization Classification of Tumors, Pathology and Genetics of tumors of hematopoietic and lymphoid tissues IARC Press: Lyon, France 2001). For AML, there would be a drop in red blood cells, platelets, and normal white blood cells. These symptoms include fatigue, shortness of breath, easy bruising and bleeding, and increased risk of infection. The symptoms of are caused by replacement of normal bone marrow with leukemic cells, which are mainly immature abnormal white blood cells that accumulate in the bone marrow and interfere with the production of normal blood cells.

In certain embodiments the cancer to be treated is B-cell neoplasms, B-cell leukemia, B-cell acute lymphoblastic leukemia, chronic lymphocytic leukemia, chronic myelogenous leukemia, Burkitt's leukemia, acute myelogenous leukemia and/or T-ALL. The maturation of B cells most typically ceases or substantially decreases when the foreign antigen has been neutralized. Occasionally, however, proliferation of a particular B cell will continue unabated; such proliferation can result in a cancer referred to as "B-cell lymphoma" or a "B-cell leukemia." In certain embodiments the cancer to be treated is chronic lymphocytic leukemia (CLL) or chronic myelogenous leukemia (CML).

In one embodiment, a bone marrow biopsy is used to assist in diagnosis of leukemia. A bone marrow biopsy sample can include bone marrow tissue or a mixture of bone marrow and bone. In another embodiment, cytogenetics is used to examine the chromosomes in individual cells. Cytogenetic testing uses a sample taken from a blood draw or a bone marrow or lymph node biopsy. The sample's chromosomes are microscopically examined for abnormalities that indicate damage to the cells' DNA and to support a diagnosis of leukemia. In another embodiment, a spinal tap can be used in the diagnosis of leukemia. Typically, a sample of cerebrospinal fluid is taken from the lower back (the lumbar area). The fluid sample is then checked for leukemia cells and other abnormalities. MRIs (Magnetic Resonance Imaging), CT (Computerized Axial Tomography) scans, and X-rays are imaging techniques that can be used to support a diagnosis of leukemia.

In certain embodiments the cancer to be treated is a plasma cell neoplasm. Examples for plasma cell neoplasms include multiple myeloma; plasma cell myeloma; plasma cell leukemia and plasmacytoma.

Any cancer characterized by high levels of DNA damage and/or DNA editing enzyme expression can be treated with a compound as described herein, e.g. a compound having the structure of Formula I. For example, sarcomas, epithelial cell cancer (carcinomas), colon cancer, gastric cancer, intestinal cancer, liver cancer, hepatocellular cancer, breast cancer, thyroid cancer, esophageal cancer, lung cancer, brain cancer, head and neck cancer, melanoma, renal cancer, prostate cancer, hemangioma, rhabdomyosarcoma, chondrosarcoma, osteosarcoma, fibrosarcoma and cholangiocarcinoma may be characterized by high levels of a DNA editing enzyme expression, e.g. AID. In certain embodiments the cancer to be treated is colon cancer, liver cancer, gastric cancer, intestinal cancer, breast cancer, lung cancer, thyroid cancer and/or cholangiocarcinoma. Any of these cancers can be diagnosed by any method known in the art. Biopsies, colonoscopies, stool samples, imaging or other means known in the art can be used to detect the presence of tumors and/or polyps. Tissue obtained by these methods is subjected to histological examination to determine the presence, type, and arrangement of malignant cells. Markers and histological signs that differentiate each type of lymphoma are known to those skilled in the art (Diagnostic Histopathology of Tumors, Fletcher, C. D. M. (Ed.), 3rd Edition, Churchill Livingstone Elsevier, China (2007); Methods of Cancer Diagnosis, Therapy and Prognosis. Hayat, M. A. (Ed), (Vol 3), Springer (2009)). Additional tests to determine the scope of the cancer and where it is located in the body can include additional biopsies, nuclear medicine, X-rays, CT scans or MRI.

In certain embodiments, treating a patient having a cancer with high DNA editing enzyme level and/or activity, e.g. high expression of AID, with a compound having the structure of Formula I decreases an indicator, marker, symptom, severity, metastasis, recurrence and/or tumor size of the cancer by at least 10%, e.g., by at least 20%, at least 30%, at least 50%, at least 75%, at least 100%, at least 200% or more as compared to the indicator, marker, symptom, severity, metastasis, recurrence and/or tumor size prior to treatment with the compound or as compared to patients not receiving treatment with the compound.

In certain embodiments the compound having the structure of Formula I is contained in a composition comprising the compound having the structure of Formula I and a pharmaceutically acceptable carrier. In further embodiments the compound having the structure of Formula I can be contained in a composition comprising a pharmaceutically acceptable carrier and another pharmaceutically effective compound.

The pharmaceutical compositions of the technology described herein can be administered alone or in combination with other therapies, including without limitation immunotherapy or immunotherapeutic agents, or other therapies which can be beneficial to patients with cancer or combinations thereof. It is contemplated that the therapeutic agents of the technology described herein can be administered together with any other therapy effective against one of the cancers described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one DSB repair inhibitor and at least one additional pharmaceutical agent.

As used herein, the term "immunotherapy" refers to treatment of a subject with an antibody or antibody-based therapeutic. As used herein, immunotherapy can be passive or active. Passive immunotherapy, as defined herein, is the passive transfer of antibody to a subject (patient). Active immunization is the induction of antibody and/or T-cell responses in a subject (patient). Exemplary immunotherapy agents include bevacizumab (Avastin®), Alemtuzumab (Campath®), cetuximab (Erbitux), Ibritumomab tiuxetan (Zevalin), Panitumumab (Vectibix), rituximab (Rituxan®), and tositumomab with 131I (Bexxar®, Corixia Corp.). Rituximab works by selectively depleting CD20+ B cells. The therapeutic effectiveness of rituximab is described in Collins-Burow et al., Rituximab and its Role as Maintenance Therapy in non-Hodgkin Lymphoma, Expert Rev Anticancer Ther 7(3):257-73 (2007); Marcus et al., The Therapeutic Use of Rituximab in non-Hodgkin's Lymphoma, Eur J Haemotal Suppl (67):5-14 (2007); Plosker et al., Rituximab: A Review of its Use in non-Hodgkin's Lymphoma and Chronic Lymphocytic Leukaemia, Drugs (2003), which are hereby incorporated by reference in their entirety. Bevacizumab (Avastin®, Genentech/Roche) blocks angiogenesis, and is used to treat various cancers, Cetuximab (IMC-C225; Erbitux®) is a chimeric (mouse/human) monoclonal antibody, against epidermal growth factor receptor (EGFR) inhibitor, given by intravenous infusion for treatment of metastatic colorectal cancer and squamous cell carcinoma of the head and neck. Ibritumomab tiuxetan (Zevalin), is a monoclonal antibody radioimmunotherapy treatment for some forms of B cell non-Hodgkin's lymphoma and binds to the CD20 antigen. Panitumumab is a fully human monoclonal antibody specific to the epidermal growth factor receptor (also known as EGF receptor, EGFR, ErbB-1 and HER1) for the treatment of colorectal cancer.

A further form of therapy for some cancers described herein is stem cell transplantation.

In some embodiments, the pharmaceutical compositions of the technology described herein can be administered after or before other therapies, including without limitation, immunotherapy agents, chemotherapy agents, radiation treatments or other therapies which can be beneficial to patients with cancer or combinations thereof.

In some embodiments, a subject is administered a cycle of treatment comprising administration of a composition comprising a compound having the structure of Formula I as described herein. The subject is then administered a cycle of treatment comprising administration of another chemotherapy, immunotherapy, radiation or other therapy which can be beneficial to patients with cancers or combinations thereof. Each cycle of treatment can comprised 1 or more administrations of a composition or therapeutic, i.e. 1 administration, 2 administrations, 3 administrations, 5 administrations, 10 administrations, 20 administrations or more. Each cycle of treatment can last at least 1 day, i.e. at least 1 day, at least 2 days, at least 1 week, at least 2 weeks, at least 3 weeks, at least 4 weeks, at least 6 weeks or more. In some embodiments, there is a hiatus or break between the cycles of treatment which can last at least 1 day, i.e. at least 1 day, at least 2 days, at least 1 week, at least 2 weeks, at least 3 weeks, at least 4 weeks, at least 6 weeks or more. A course of treatment comprising a cycle of treatment with a compound having the structure of Formula I as described herein, optionally a break, and a cycle of treatment with another chemotherapy, immunotherapy, radiation or other therapy which can be beneficial to patients with cancers or combinations thereof, and optionally a second break can be repeated in part or in whole. In some embodiments, the cycle of treatment with a compound having the structure of Formula I is the second cycle and the other anti-cancer therapy is used in the first cycle. In some embodiments, the other chemotherapy, immunotherapy, radiation or other therapy which can be beneficial to patients with cancers or combinations thereof comprises a therapy which causes damage to the subject's DNA. In some embodiments, the other chemotherapy, immunotherapy, radiation or other therapy which can be beneficial to patients with cancers or combinations thereof comprises doxorubicin. In some embodiments, the other chemotherapy, immunotherapy, radiation or other therapy which can be beneficial to patients with cancers or combinations thereof comprises fludarabine.

Other therapies include, without limitation, chemotherapies may be done before, during or after the methods described herein. In one embodiment, the chemotherapy is administered before or after, but not during, treatment with a composition or method as described herein. Non-limiting examples of chemotherapies include radiation or treatment with chemotherapy agents such as actinomycin, amsacrine (Amsidine®), anthracyclines, bleomycin (Blenoxane®), busulfan, camptothecin, carboplatin (Paraplatin®), chlorambucil (Leukeran®), cisplatin, cyclophosphamide (Cytoxan®), cladribine, cytarabine (Cytosar-U®), cytoxan, dacarbazine (DTIC-Dome®), dactinomycin, daunorubicin, dexamethasone (Decadron®), docetaxel, doxorubicin (Adriamycin®), epirubicin, etoposide (Etopophos®), fludarabine (Fludara®), hexamethylmelamineoxaliplatin, ifosfamide (Ifex®), iphosphamide, melphalan, merchlorethamine, methotrexate, mitomycin, mitoxantrone, nitrosourea, paclitaxel, plicamycin, prednisone, procarbazine, teniposide, triethylenethiophosphoramide, etoposide (VPI6), vincristine (Oncovin®), vinblastine, bendamustine (Ribomustin and Treanda), CHOP therapy, monoclonal antibodies and inhibitors of the c-myc gene, DNA methyltransferase, proteasomes and cyclin-dependent kinases.

Chemotherapeutics can include agents which induce DNA damage. Non-limiting examples of such agents can include alkylating agents, nitrosourea, anti-metabolites, plant alkaloids, plant extracts, or radioisotopes.

Also included are courses of therapy which include, but are not limited to, 1) the CODOX-M/IVAC regimen (Magrath protocol)—two cycles of CODOX-M (cyclophosphamide, vincristine, doxorubicin and high-dose methotrexate) alternating with IVAC (ifosfamide, etoposide and high-dose cytarabine), 2) three cycles of CODOX-M. Also included are modified versions of such combination therapies such as the adapted Magrath protocols of the United Kingdom Lymphoma Group and the Dana-Farber Cancer Institute.

As described above herein, some embodiments of the invention relate to methods of treatment comprising administering a therapeutically effective amount of a compound described herein, e.g. a compound having the structure of Formula I to a subject in need of treatment for autoimmune disease. As used herein, the terms "autoimmune disease" or "autoimmune disorder" refer to a condition that is immune-mediated due to an attack on self-tissues, such as when a subject's own antibodies react with host tissue, but can also involve an immune response to a microorganism. In some embodiments, the subject can be determined to have an increased level of DNA damage and/or increased level and/or activity of a DNA editing enzyme (e.g., AID). In some embodiments, the method can further comprise selecting a subject having an increased level of DNA damage and/or increased level and/or activity of a DNA editing enzyme (e.g., AID).

As described above herein, some embodiments of the invention relate to methods of treatment comprising administering a therapeutically effective amount of a compound described herein, e.g. a compound having the structure of Formula I to a subject in need of treatment for an immune deficiency. As used herein, the term "immune deficiency" refers to a condition in which a portion or some portions of cell components constituting an immune system are defective or dysfunction, so that a normal immune mechanism is damaged. In other words, "immune deficiency" means a condition under which: congenital immunity and/or acquired immunity are suppressed and/or decreased. In some embodiments, the immune-deficiency subject is an immunocompromised subject. Non-limiting examples of immune deficiencies can include AIDS, hypogammaglobulinemia, agammaglobulinemia, granulocyte deficiency, chronic granulomatous disease, asplenia, SCID, complement deficiency, and/or sickle cell anemia.

In some embodiments, the subject can be determined to have an increased level of DNA damage and/or increased level and/or activity of a DNA editing enzyme (e.g., AID). In some embodiments, the method can further comprise selecting a subject having an increased level of DNA damage and/or increased level and/or activity of a DNA editing enzyme (e.g., AID).

In some embodiments, an increased level and/or activity of a DNA editing enzyme can be a level of enzyme that is higher than the level of enzyme in cells of the same type from a healthy individual. In some embodiments, the cells that express an elevated level of DNA editing enzyme can be autoimmune cells. As used herein, "autoimmune cell" or "autoreactive cell" refers to immune cells that have activity towards and/or recognize cells or biological components of the organism from which the cell is derived. Examples of cells which can be autoimmune cells include, but are not limited to, adult splenocytes, T cells, and B cells. As used herein, the term "immune cell" refers to a cell that is part of the innate and/or adaptive immune systems. Immune cells can be of hematopoietic origin and include, by way of non-limiting example, lymphocytes, B cells, T cells, NK cells, myeloid cells, monocytes, macrophages, eosinophils, mast cells, basophils, granulocytes, dendritic cells, phagocytes, and neutrophils.

In some embodiments, the methods of treatment comprise (a) selecting a subject having B cells that express an elevated level of activation-induced cytidine deaminase (AID); and (b) administering a therapeutically effective amount of a compound described herein (e.g. a compound having the structure of Formula I) to the subject; wherein an elevated level of AID is a level of AID that is higher than the level of AID in B cells from a healthy individual. In some embodiments, the B cells that express an elevated level of AID are B cells associated with autoimmune disease. As used herein, the term "B cell associated with autoimmune disease" refers to B cells with abnormal function, behavior, and/or proliferation in a particular autoimmune disease. In some embodiments, the B cells associated with autoimmune disease can be B cells which cause the disease due to their abnormal function, behavior, and/or proliferation. In some embodiments, the B cells associated with autoimmune disease can be B cells which cause one or more symptoms of an autoimmune disease due to their abnormal function, behavior, and/or proliferation. In some embodiments, a subject having B cells associated with an autoimmune disease can be a subject having or diagnosed as having an autoimmune disease characterized or caused by B cells with abnormal function, behavior, and/or proliferation. By way of non-limiting example, in systemic lupus erythematosus, a subject's B cells abnormally produce antibodies specific for auto-antigens and in rheumatoid arthritis, a subject's B cells interact abnormally with the subject's T cells.

In certain embodiments, the methods described herein selectively treat autoimmune diseases by exploiting lymphoid recombination systems to induce self-destruction of diseased B-cells while sparing normal cells. This approach takes advantage of the finding that the B-cell recombinase AID induces widespread genomic breaks and cell death in primary B-cells with diminished homologous recombination ability. As described herein, it has been determined that where a population of cells characterized by increased expression of a DNA editing enzyme, e.g. AID is treated with a compound as described herein (e.g., a compound having the structure of Formula I), cell death results.

Accordingly, provided herein are methods for treating patients with autoimmune diseases, e.g., autoimmune diseases characterized by aberrant B cell proliferation, class switching, or activation. In some embodiments, the autoimmune disease can be characterized by increased B cell proliferation, class switching, or activation. In some embodiments, the autoimmune disease can be characterized by having B cells with increased levels and/or activity of a DNA editing enzyme, e.g. AID. In some embodiments, the method relates to treating a subject with an autoimmune disease and cells with high DNA editing enzyme expression with a DSB repair inhibitor. Autoimmune diseases known to be characterized by aberrant B cell proliferation, class switching and/or activation include, but are not limited to lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis; discoid lupus; subacute cutaneous lupus erythematosus; cutaneous lupus erythematosus including chilblain lupus erythematosus; chronic arthritis; Sjogren's syndrome; autoimmune nephritis; autoimmune diabetes nephritis; autoimmune vasculitis; autoimmune hepatitis; autoimmune carditis; autoimmune encephalitis; and autoimmune mediated hematological disease. In certain embodiments, autoimmune diseases are characterized by aberrant expression of a DNA editing enzyme. In certain embodiments, the autoimmune disease to be treated is Crohn's disease, ulcerative colitis, vasculitis; ankylosing spondylitis; Behçet's disease; paraneoplastic autoimmunity or dermatomyositis. In some embodiments, the autoimmune disease to be treated according to the methods described herein is an autoimmune disease characterized by aberrant B cell proliferation. In some embodiments, the autoimmune disease can be, e.g., inflammatory chronic rhinosinusitis, celiac disease, inflammatory bowel disease, Barrett's esophagus, inflammatory gastritis autoimmune nephritis, or autoimmune diabetes.

Lupus or lupus erythematosus or systemic lupus erythematosus (SLE) is an autoimmune disorder that can cause chronic inflammation in various parts of the body, especially the skin, joints, blood, and kidneys. The body's immune system normally makes proteins called antibodies to protect the body against viruses, bacteria, and other foreign materials (i.e., antigens). In an autoimmune disorder such as lupus, or lupus erythematosus or SLE, the immune system loses the ability to discriminate between antigens and its own cells and tissues and can thus make antibodies directed against its own cells and tissues to form immune complexes. These immune complexes can build up in the tissues and cause inflammation, injury to tissues and/or pain. The three most common types of lupus include systemic lupus erythematosus (SLE), cutaneous lupus erythematosus (CLE) and drug-induced lupus. Additional types of autoimmune disorders include, but are not limited to subacute cutaneous lupus erythematosus, cutaneous lupus erythematosus including chilblain lupus erythematosus, rheumatoid arthritis, chronic arthritis, Sjogren's syndrome, autoimmune nephritis, autoimmune vasculitis, autoimmune hepatitis, autoimmune carditis, autoimmune encephalitis, and autoimmune mediated hematological disease. More detailed descriptions of lupus or lupus erythematosus can be found in Wallace, 2000, The Lupus Book: A Guide for Patients and Their Families, Oxford University Press, Revised and Expanded Edition; Kuhn et al., 2004, Cutaneous Lupus Erythematosus, Springer, First Edition; and Lahita, 1999, Systemic Lupus Erythematosus, Academic Press, Third Edition; which are incorporated by reference herein in their entireties.

Methods of diagnosing lupus erythematosus are well known in the art. Laboratory tests for the presence of lupus include the LE Cell Test, the Anti-Nuclear Antibody Test, and the test for anti-DNA antibodies. Lupus is, however, often recognized by particular clinical manifestations including: (i) arthritis (occurring in 90-95% of persons with systemic lupus), (ii) skin changes, such as a photosensitive induced "butterfly" rash across the bridge of the nose, across the cheeks and/or beneath the eyes, and/or red, raised and scaly patches, known as discoid lupus, anywhere on the body (occurring in 75-80% of persons with lupus), (iii) hematologic abnormalities, such as anemia, leukopenia, and thrombocytopenia (occurring in about 50% of persons with lupus), (iv) kidney impairment (occurring in about 50% of persons with lupus), (v) heart or lung disease, such as an irritation of the heart or lung lining causing pericarditis or pleurisy (occurring in about 30% of persons with lupus), and (vi) neuropsychiatric changes (occurring in about 10% to 20% of persons with lupus). By way of non-limiting example, a subject can be diagnosed with systemic erythematosus lupus by having elevated levels of at least one autoantibody relative to the level of the autoantibody in a subject not diagnosed with systemic erythematosus lupus. Exemplary autoantibodies for diagnosis of systemic erythematosus lupus include, but are not limited to, antinuclear antibody (ANA), anti-double strand DNA antibody (anti-dsDNA), anti Sm nuclear antigen antibody (anti-Sm), anti-phsopholipid antibody, and any combinations thereof. Such elevated levels can be at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, or at least 10-fold or higher compared to a subject not diagnosed with systemic erythematosus lupus. Alternatively, a subject can be diagnosed with systemic erythematosus lupus by having elevated levels of interferon-beta and or interferon-beta gene expression relative to levels in a subject not diagnosed with systemic erythematosus lupus. Such elevated levels can be at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, or at least 10-fold or higher compared to a subject not diagnosed with systemic erythematosus lupus.

In certain embodiments, treating a patient having an autoimmune disease or an autoimmune disorder treated with a compound as described herein, e.g. a compound having the structure of Formula I, has a decrease of an indicator, marker, symptom, and/or severity of the autoimmune disease by at least 10%, e.g., by at least 20%, at least 30%, at least 50%, at least 75%, at least 80%, at least 90%, at least 95% or more as compared to the indicator, marker, symptom, and/or severity prior to treatment or as compared to patients not receiving treatment with a compound as described herein.

The technology described herein can relate to the use of at least one compound having the structure of Formula I and compositions comprising at least one such compound for the treatment of an autoimmune disease or an autoimmune disorder having B cells having increased levels of a DNA editing enzyme, e.g., AID protein or mRNA. For example, a composition comprising a compound of Formula I is used to reduce the severity, duration, or number of symptoms associated with one of the following, which are offered by way of example only; lupus erythematosus; systemic lupus erythematosus (SLE); cutaneous lupus erythematosus (CLE); drug-induced lupus; subacute cutaneous lupus erythematosus; cutaneous lupus erythematosus including chilblain lupus erythematosus; rheumatoid arthritis; Sjogren's syndrome; autoimmune nephritis; autoimmune vasculitis; autoimmune hepatitis; autoimmune carditis; autoimmune encephalitis; and autoimmune mediated hematological disease. By "reduce" in this context is meant a statistically significant decrease in such level. The decrease can be, for example, at least 10%, at least 20%, at least 50%, at least 90% or more.

The pharmaceutical compositions of the technology described herein can be administered alone or in combination with other therapies, including without limitation anti-inflammatories, or other therapies which can be beneficial to patients with autoimmune diseases or combinations thereof. It is contemplated that the therapeutic agents of the technology described herein can be administered together with any other therapy effective against one of the autoimmune diseases described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one compound having a structure of Formula I and at least one additional pharmaceutical agent.

By way of non-limiting example, agents for treatment of lupus erythematosus include, but are not limited to, non-steroidal anti-inflammatory drugs (NSAIDs), corticosteroids, antimalarials (e.g. chloroquinine; hydroxychloroquine; and quinacrine), immunosuppressants (e.g. azathioprine, cyclosporine A, alkylating agents, nitrogen mustards, chlorambucil or cyclophosphamide), heparin, aspirin, danazol (Danocrine), dehydroepiandrosterone (DHEA), vincristine (Oncovin), warfarin, methylprednisolone pulse therapy, dapsone, thalidomide (Synovir); methylprednisolone sodium succinate (A-Methapred, Solu-Medrol), methotrexate (Rheumatrex), hydroxychloroquine (Plaquenil), triamcinolone (Aristospan), retinoids (e.g. istretinoin and etretinate). Non-limiting examples of anti-inflammatory drugs (NSAIDs) include such as aspirin, salisylates, ibuprofen, naproxen, clinoril, oxaprozin and tolmetin.

In some embodiments, the pharmaceutical compositions of the technology described herein can be administered after or before other therapies, including without limitation, anti-inflammatories or immunosuppressants or other therapies which can be beneficial to patients with autoimmune diseases or combinations thereof.

As described above herein, some embodiments of the invention relate to methods of treatment comprising administering a therapeutically effective amount of a compound described herein, e.g. a compound having the structure of Formula I to a subject in need of treatment for neurodegenerative disease. In some embodiments, the subject can be determined to have an increased level of DNA damage and/or increased level and/or activity of a DNA editing enzyme (e.g., AID). In some embodiments, the method can further comprise selecting a subject having an increased level of DNA damage and/or increased level and/or activity of a DNA editing enzyme (e.g., AID).

In some embodiments, an increased level and/or activity of a DNA editing enzyme can be a level of enzyme that is higher than the level of enzyme in cells of the same type from a healthy individual. In some embodiments, the cells that express an elevated level of DNA editing enzyme can be neurological cells and/or nervous system cells. As used herein, "nervous system cells" refers to cells of the central and/or peripheral nervous systems, including, but not limited to nerves, neurons, and glial cells. In some embodiments, the nervous system cell can be a neuron.

In some embodiments, the methods of treatment comprise (a) selecting a subject having nervous system cells that express an elevated level of a DNA editing enzyme (e.g., activation-induced cytidine deaminase (AID)); and (b) administering a therapeutically effective amount of a compound described herein (e.g. a compound having the structure of Formula I) to the subject; wherein an elevated level of enzyme is a level of enzyme that is higher than the level of enzyme in nervous system cells from a healthy individual. In some embodiments, the cells that express an elevated level of DNA editing enzyme are cells associated with neurodegenerative disease. As used herein, the term "nervous system cell associated with neurodegenerative disease" refers to cells with abnormal function, behavior, and/or proliferation in a particular neurodegenerative disease. In some embodiments, the cells associated with neurodegenerative disease can be cells which cause the disease due to their abnormal function, behavior, and/or proliferation. In some embodiments, the cells associated with neurodegenerative disease can be cells which cause one or more symptoms of a neurodegenerative disease due to their abnormal function, behavior, and/or proliferation. In some embodiments, a subject having cells associated with an neurodegenerative disease can be a subject having or diagnosed as having an neurodegenerative disease characterized or caused by nervous systems cells with abnormal function, behavior, and/or proliferation.

Non-limiting examples of neurodegenerative diseases which can be treated according to the methods described herein can include Alzheimer's disease, Dentatorubropallidoluysian atrophy (DRPLA), Huntington's Disease (HD), Spinocerebellar ataxia Type 1 (SCA1), Spinocerebellar ataxia Type 2 (SCA2), Spinocerebellar ataxia Type 3 (SCA3), Spinocerebellar ataxia 6 (SCA6), Spinocerebellar ataxia Type 7 (SCA7), Spinocerebellar ataxia Type 8 (SCA8), Spinocerebellar ataxia Type 12 (SCA12), Spinocerebellar ataxia Type 17 (SCA17), Spinobulbar Muscular Ataxia/Kennedy Disease (SBMA), Fargile X syndrome (FRAXA), Fragile XE mental retardation (FRAXE), and Myotonic dystrophy (DM).

In certain embodiments, treating a patient having a neurodegenerative disease or an neurodegenerative disorder having nervous system cells with high DNA editing enzyme levels or activity (e.g. AID levels or activity) with a compound as described herein, e.g. a compound having the structure of Formula I, decreases an indicator, marker, symptom, and/or severity of the autoimmune disease by at least 10%, e.g., by at least 20%, at least 30%, at least 50%, at least 75%, at least 80%, at least 90%, at least 95% or more as compared to the indicator, marker, symptom, and/or severity prior to treatment or as compared to patients not receiving treatment with a compound as described herein.

The technology described herein can relate to the use of at least one compound having the structure of Formula I and compositions comprising at least one such compound for the treatment of an neurodegenerative disease or an neurodegenerative disorder having nervous system cells having increased levels of a DNA editing enzyme, e.g., AID protein or mRNA. For example, a composition comprising a compound of Formula I is used to reduce the severity, duration, or number of symptoms associated with one of the following, which are offered by way of example only; Alzheimer's disease, Dentatorubropallidoluysian atrophy (DRPLA), Huntington's Disease (HD), Spinocerebellar ataxia Type 1 (SCA1), Spinocerebellar ataxia Type 2 (SCA2), Spinocerebellar ataxia Type 3 (SCA3), Spinocerebellar ataxia 6 (SCA6), Spinocerebellar ataxia Type 7 (SCA7), Spinocerebellar ataxia Type 8 (SCA8), Spinocerebellar ataxia Type 12 (SCA12), Spinocerebellar ataxia Type 17 (SCA17), Spinobulbar Muscular Ataxia/Kennedy Disease (SBMA), Fargile X syndrome (FRAXA), Fragile XE mental retardation (FRAXE), and Myotonic dystrophy (DM). By "reduce" in this context is meant a statistically significant decrease in such level. The decrease can be, for example, at least 10%, at least 20%, at least 50%, at least 90% or more.

The pharmaceutical compositions of the technology described herein can be administered alone or in combination with other therapies, including without limitation treatments or therapies which can be beneficial to patients with neurodegenerative diseases or combinations thereof. It is contemplated that the therapeutic agents of the technology described herein can be administered together with any other therapy effective against one of the neurodegenerative diseases described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one compound having a structure of Formula I and at least one additional pharmaceutical agent.

In some embodiments, the pharmaceutical compositions of the technology described herein can be administered after or before other therapies, including without limitation, treatments or therapies which can be beneficial to patients with neurodegenerative diseases or combinations thereof. By way of non-limiting example, a treatment or therapy for Huntington's Disease can be selected from the group consisting of: regular physical exercise; regular mental exercise; improvements to the diet; or administering creatine monohydrate, coenzyme Q10, sodium phenylbutyrate.

In some embodiments, there is provided herein a method of sensitizing cells to death and/or inducing or causing cell death. In some embodiments, there is provided herein a method of causing cell death comprising: administering to a cell an effective amount of a DNA editing enzyme; and thereafter contacting the cells with a compound having the structure of Formula I; thereby causing cell death. In some embodiments, there is provided herein a method of sensitizing a cell to cell death comprising: administering to a subject a therapeutically effective amount of a DNA editing enzyme; and thereafter administering to the subject a compound having the structure of Formula I; thereby sensitizing a cell in the subject to cell death. In some embodiments, the DNA editing enzyme can be a member of the APOBEC family, or AID, Rag1 or Rag2 or SPO11. In some embodiments, the DNA editing enzyme can be a member of the APOBEC family. Non-limiting examples of APOBEC family members include APOBEC1; APOBEC2, APOBEC3A; APOBEC3C; APOBEC3E; APOBEC3F; APOBEC3G; APOBEC3H; and APOBEC4.

In some embodiments, the DNA editing enzyme can be administered in the form of a polypeptide, a nucleic acid encoding a DNA editing enzyme, or a vector comprising a nucleic acid encoding a DNA editing enzyme. In some embodiments, the DNA editing enzyme can be AID. In some embodiments, the DNA editing enzyme administered to the cell is a polypeptide comprising the sequence of AID or a variant, functional fragment, or homolog thereof. In some embodiments, the DNA editing enzyme administered to the cell is a nucleic acid encoding an AID polypeptide, such that AID or a variant, functional fragment, or homolog thereof will be expressed in the cell administered the nucleic acid.

Gene therapy compositions and methods are also contemplated for use with the methods described herein. Such methods allow clinicians to introduce DNA encoding a polypeptide or RNA molecule of interest directly into a patient (in vivo gene therapy) or into cells isolated from a patient or a donor (ex vivo gene therapy). Therapeutic proteins produced by transduced cells after gene therapy can be maintained at a relatively constant level in, for example, in cancerous cells, e.g. a tumor of a subject, as compared to a protein that is administered directly. Such sustained production of a therapeutic agent, such as AID and/or a compound having the structure of Formula I, is particularly appropriate in the treatment of chronic diseases, such as cancers.

Further, regulatable genetic constructs using small molecule inducers have been developed that can be included in vectors to be used in some embodiments of the present invention described herein. (Rivera et al. (1996) Nat. Med. 2:1028-32; No et al. (1996) Proc. Natl. Acad. Sci. USA, 93:3346-51; Gossen and Bujard (1992) Proc. Natl. Acad. Sci. USA 89:5547-51; the GeneSwitch® system (Valentis, Inc., Burlingame, Calif.)). These systems are based on the use of engineered transcription factors the activity of which is controlled by a small molecule drug, and a transgene, the expression of which is driven by the regulated transcription factor (Rivera et al. (1996) Nat. Med. 2:1028-32; Pollock et al. (2000) Proc. Natl. Acad. Sci. USA 97:13221-26; U.S. Pat. Nos. 6,043,082 and 6,649,595; Rivera et al. (1999) Proc. Natl. Acad. Sci. USA 96:8657-62).

Vectors useful in the methods described herein can include, but are not limited to, plasmids, retroviral vectors, adenoviral vectors, adeno-associated viral vectors, herpes virus and pox virus vectors.

The term "transduction" as used herein refers to the use of viral particles or viruses to introduce exogenous nucleic acids into a cell. The term "transfection" as used herein in reference to methods, such as chemical methods, to introduce exogenous nucleic acids, such as the nucleic acid sequences encoding an agent which increases the activity and/or level of AID as described herein, into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to those that use cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

In some embodiments, the cell can be an in vitro cell, a cell in cell culture, or a cell in a sample obtained from a subject. In some embodiments, the DNA editing enzyme, and/or the compound having the structure of Formula I can, for example, be added to the cell culture media in which the cell is being maintained. In some embodiments, the DNA editing enzyme, and/or the compound having the structure of Formula I can, for example, be comprised by compositions which mediate or enhance their entry into the cell. Suitable compositions for delivering agents to cells, either in vivo or in vitro are described below herein, e.g. liposomes.

In some embodiments, the cell can be a cell in vivo, e.g. a cell in a subject.

In some embodiments, it is desirable to target specific cells or tissues of interest (targeted cells or tissues), e.g. to enhance effectiveness of vectors, minimize the effective dose, and/or minimize side effects or off-target effects. Methods of targeting agents to particular cell types are well known in the art. For reviews, see Peng et al., "Viral Vector Targeting", Curr. Opin. Biotechnol. 10:454-457, 1999; Gunzburg et al., "Retroviral Vector Targeting for Gene Therapy", Cytokines Mol. Ther. 2:177-184, 1996; Wickham, "Targeting Adenovirus", Gene Ther. 7:110-114, 2000; Dachs et al., "Targeting Gene Therapy to Cancer: A Review", Oncol. Res. 9:313-325, 1997; Curiel, "Strategies to Adapt Adenoviral Vectors for Targeted Delivery", Ann NY Acad. Sci. 886:158171, 1999; Findeis et al., "Targeted Delivery of DNA for Gene Therapy via Receptors", Trends Biotechnol. 11:202205, 1993; all of which are incorporated by reference herein in their entirety.

Some targeting strategies make use of cellular receptors and their natural ligands in whole or in part. See, for example, Cristiano et al., "Strategies to Accomplish Gene Delivery Via the Receptor-Mediated Endocytosis Pathway", Cancer Gene Ther., Vol. 3, No. 1, pp. 49-57, January-February 1996; S. C. Philips, "Receptor-Mediated DNA Delivery Approaches to Human Gene Therapy", Biologicals, Vol. 23, No. 1, pp. 13-6, March 1995; Michael et al., "Strategies to Achieve Targeted Gene Delivery Via the Receptor-Mediated Endocytosis Pathway", Gene Ther., Vol. 1, No. 4, pp. 223-32, July 1994; Lin et al., "Antiangiogenic Gene Therapy Targeting The Endothelium-Specific Receptor Tyrosine Kinase Tie2", Proc. Natl. Acad. Sci., USA, Vol. 95, pp. 8829-8834, 1998. Sudimack et al, "Targeted Drug Delivery Via the Folate Receptor", Adv. Drug Deliv., pp. 147-62, March 2000; Fan et al., "Therapeutic Application of Anti-Growth Factor Receptor Antibodies", Curr. Opin. Oncol., Vol. 10, No. 1, pp. 67-73, January 1998; Wadhwa et al., "Receptor Mediated Glycotargeting", J. Drug Target, Vol. 3, No. 2, pp. 111-27, 1995; Perales et al, "An Evaluation of Receptor-Mediated Gene Transfer Using Synthetic DNA-Ligand Complexes", Eur. J. Biochem, Vol. 1, No 2, pp. 226, 255-66, December 1994; Smith et al., "Hepatocyte Directed Gene Delivery by Receptor-Mediated Endocytosis", Semin Liver Dis., Vol. 19, No. 1, pp. 83-92, 1999; which are all incorporated by reference herein in their entireties.

Antibodies, particularly single-chain antibodies, to surface antigens specific for a particular cell type may also be used as targeting elements. See, for example, Kuroki et al., "Specific Targeting Strategies of Cancer Gene Therapy Using a Single-Chain Variable Fragment (scFv) with a High Affinity for CEA", Anticancer Res., pp. 4067-71, 2000; U.S. Pat. No. 6,146,885, to Dornburg, entitled "Cell-Type Specific Gene Transfer Using Retroviral Vectors Containing Antibody-Envelope Fusion Proteins"; Jiang et al., "In Vivo Cell Type-Specific Gene Delivery With Retroviral Vectors That Display Single Chain Antibodies", Gene Ther. 1999, 6:1982-7; Engelstadter et al., "Targeting Human T Cells By Retroviral Vectors Displaying Antibody Domains Selected From A Phage Display Library", Hum. Gene Ther. 2000, 11:293-303; Jiang et al., "Cell-Type-Specific Gene Transfer Into Human Cells With Retroviral Vectors That Display Single-Chain Antibodies", J. Virol 1998, 72:10148-56; Chu et al., "Toward Highly Efficient Cell-Type-Specific Gene Transfer With Retroviral Vectors Displaying Single-Chain Antibodies", J. Virol 1997, 71:720-5; Chu et al., Retroviral Vector Particles Displaying The Antigen-Binding Site Of An Antibody Enable Cell-Type-Specific Gene Transfer, J. Virol 1995, 69:2659-63; and Chu et al, "Cell Targeting With Retroviral Vector Particles Containing Antibody-Envelope Fusion Proteins", Gene Ther. 1994, 1:292-9; which are all incorporated by reference herein in their entireties.

The compositions and methods described herein can be administered to a subject having or diagnosed as having, e.g. cancer, an autoimmune disease and/or a neurodegenerative disease. In some embodiments, the methods described herein comprise administering an effective amount of compositions described herein, e.g. a compound having the structure of Formula I to a subject in order to alleviate a symptom of a disease or condition. As used herein, "alleviating a symptom" is ameliorating any condition or symptom associated with the disease or condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a compound needed to alleviate at least one or more symptom of the disease or disorder, and relates to a sufficient amount of pharmacological composition to provide the desired effect. The term "therapeutically effective amount" therefore refers to an amount of a compound that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, e.g., a compound having the structure of Formula I, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor growth, among others. The dosage can be determined by a physician and adjusted, as necessary, to suit observed effects of the treatment.

In some embodiments, the technology described herein relates to a pharmaceutical composition comprising a compound having the structure of Formula I as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent.

In certain embodiments the compound having the structure of Formula I is contained in a composition comprising the compound having the structure of Formula I and a pharmaceutically acceptable carrier. In further embodiments the compound having the structure of Formula I can be contained in a composition comprising a pharmaceutically acceptable carrier and another pharmaceutically effective compound.

For administration to a subject, the compounds can be provided in pharmaceutically acceptable compositions. These pharmaceutically acceptable compositions comprise a therapeutically effective amount of at least one compound having the structure of Formula I as described above, formulated together with one or more pharmaceutically acceptable carriers (additives) and/or diluents. As described in detail below, the pharmaceutical compositions of the technology described herein can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally. Additionally, compounds can be implanted into a patient or injected using a drug delivery system. Coated delivery devices can also be useful. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; 6,747,014; and U.S. Pat. No. 35 3,270,960.

Many organized surfactant structures have been studied and used for the formulation of drugs. These include monolayers, micelles, bilayers and vesicles. Vesicles, such as liposomes, have attracted great interest because of their specificity and the duration of action they offer from the standpoint of drug delivery. Liposomes are unilamellar or multilamellar vesicles which have a membrane formed from a lipophilic material and an aqueous interior. The aqueous portion contains the composition to be delivered. Liposomes can be cationic (Wang et al., Biochem. Biophys. Res. Commun., 1987, 147, 980-985), anionic (Zhou et al., Journal of Controlled Release, 1992, 19, 269-274), or nonionic (Hu et al. S.T.P. Pharma. Sci., 1994, 4, 6, 466). Liposomes can comprise a number of different phospholipids, lipids, glycolipids, and/or polymers which can impart specific properties useful in certain applications and which have been described in the art (Allen et al., FEBS Letters, 1987, 223, 42; Wu et al., Cancer Research, 1993, 53, 3765; Papahadjopoulos et al., Ann. N.Y. Acad. Sci., 1987, 507, 64; Gabizon et al., PNAS, 1988, 85, 6949; Klibanov et al. FEBS Lett., 1990, 268, 235; Sunamoto et al., Bull. Chem. Soc. Jpn., 1980, 53, 2778; Illum et al., FEBS Lett., 1984, 167, 79; Blume et al., Biochimica et Biophysica Acta, 1990, 1029, 91; Hughes et al., Methods Mol Biol. 2010; 605:445-59; U.S. Pat. Nos. 4,837,028; 5,543,152; 4,426,330; 4,534,899; 5,013,556; 5,356,633; 5,213,804; 5,225,212; 5,540,935; 5,556,948; 5,264,221; 5,665,710; European Patents EP 0 445 131 B1; EP 0 496 813 B1; and European Patent Publications WO 88/04924; WO 97/13499; WO 90/04384; WO 91/05545; WO 94/20073; WO 96/10391; WO 96/40062; WO 97/0478).

The compositions of the technology described herein can be prepared and formulated as emulsions or microemulsions. Emulsions are typically heterogeneous systems of one liquid dispersed in another in the form of droplets usually exceeding 0.1 μm in diameter and have been described in the art. Microemulsion can be defined as a system of water, oil and amphiphile which is a single optically isotropic and thermodynamically stable liquid solution and can comprise surfactants and cosurfactants. Both of these drug delivery means have been described in the art (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 199, 245, & 335; Higuchi et al., in Remington's Pharmaceutical Sciences, Mack Publishing Co., Easton, Pa., 1985, p. 301; Leung and Shah, in: Controlled Release of Drugs: Polymers and Aggregate Systems, Rosoff, M., Ed., 1989, VCH Publishers, New York, pages 185-215; Schott, in Remington's Pharmaceutical Sciences, Mack Publishing Co., Easton, Pa., 1985, p. 271; Constantinides et al., Pharmaceutical Research, 1994, 11, 1385-1390; Ritschel, Meth. Find. Exp. Clin. Pharmacol., 1993, 13, 205; Ho et al., J. Pharm. Sci., 1996, 85, 138-143; Lee et al., Critical Reviews in Therapeutic Drug Carrier Systems, 1991, p. 92; U.S. Pat. Nos. 6,191,105; 7,063,860; 7,070,802; 7,157,099).

In one embodiment, the liposome or emulsion formulation comprises a surfactant. Surfactants find wide application in formulations such as emulsions (including microemulsions) and liposomes. The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285). Suitable surfactants include fatty acids and/or esters or salts thereof, bile acids and/or salts thereof. In some embodiments, the surfactant can be anionic, cationic, or nonionic. The use of surfactants in drug products, formulations and in emulsions has been reviewed (Rieger, in Pharmaceutical Dosage Forms, Marcel Dekker, Inc., New York, N.Y., 1988, p. 285).

In one embodiment, the technology described herein employs various penetration enhancers to affect the efficient delivery of compounds having the structure of Formula I across cell membranes. Penetration enhancers can be classified as belonging to one of five broad categories, i.e., surfactants, fatty acids, bile salts, chelating agents, and non-chelating non-surfactants all of which have been described elsewhere (see e.g., Malmsten, M. Surfactants and polymers in drug delivery, Informa Health Care, New York, N.Y., 2002; Lee et al., Critical Reviews in Therapeutic Drug Carrier Systems, 1991, p. 92; Takahashi et al., J. Pharm. Pharmacol., 1988, 40, 252; Touitou, E., et al. Enhancement in Drug Delivery, CRC Press, Danvers, Mass., 2006; Muranishi, Critical Reviews in Therapeutic Drug Carrier Systems, 1990, 7, 1-33; El Hariri et al., J. Pharm. Pharmacol., 1992, 44, 651-654; Brunton, Chapter 38 in: Goodman & Gilman's The Pharmacological Basis of Therapeutics, 9th Ed., Hardman et al., Eds., McGraw-Hill, New York, 1996, pp. 934-935; Swinyard, Chapter 39 In: Remington's Pharmaceutical Sciences, 18th Ed., Gennaro, ed., Mack Publishing Co., Easton, Pa., 1990, pages 782-783; Yamamoto et al., J. Pharm. Exp. Ther., 1992, 263, 25; Yamashita et al., J. Pharm. Sci., 1990, 79, 579-583; Jarrett, J. Chromatogr., 1993, 618, 315-339; Katdare, A. et al., Excipient development for pharmaceutical, biotechnology, and drug delivery, CRC Press, Danvers, Mass., 2006; Buur et al., J. Control Rel., 1990, 14, 43-51)

Oral formulations and their preparation are described in detail in U.S. Pat. No. 6,887,906, US Publn. No. 20030027780, and U.S. Pat. No. 6,747,014, each of which is incorporated herein by reference. Compositions and formulations for parenteral, intraparenchymal, intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients. Aqueous suspensions can further contain substances which increase the viscosity of the suspension including, for example, sodium carboxymethylcellulose, sorbitol and/or dextran. The suspension can also contain stabilizers.

In some embodiments, the pharmaceutical composition comprising a compound having the structure of Formula I as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a compound having the structure of Formula I as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a compound having the structure of Formula I as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the compound having the structure of Formula I can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The compositions of the technology described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the technology described herein, such as dyes, flavoring agents, preservatives, antioxidants, opacifiers, thickening agents and stabilizers. However, such materials, when added, should not unduly interfere with the biological activities of the components of the compositions of the technology described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with compound(s) having the structure of Formula I of the formulation.

Suitable emulsifiers include synthetic non-ionic emulsifiers, such as, for example, ethoxylated ethers, ethoxylated esters, polyoxypropylene-polyoxyethylene block co-polymers and phospholipids. Naturally-occurring phospholipids, such as egg or soya phospholipids, and modified or artificially manipulated phospholipids or mixtures thereof can also be used. In some embodiments, emulsifiers are egg phospholipids and soya phospholipids. Egg yolk phospholipids include phosphatidylcholine, lecithin and phosphatidylethanolamine.

The compositions of the technology described herein may also include stabilizing agents. Anionic stabilizers include, for example, phosphatidylethanolamines, conjugated with polyethylene glycol, (PEG-PE) and phosphatidylglycerols, a specific example of which is dimyristolphosphatidylgylcerol (DMPG). Additional stabilizers include, but are not limited to, oleic acid and its sodium salt, cholic acid and deoxycholic acid and respective salts thereof, cationic lipids such as stearylamine and oleylamine, and 3|3-[N—(N',N'-dimethylaminoethane)carbamoyl]cholesterol (DC-Chol).

The compositions of the technology described herein can be made isotonic with blood by the incorporation of a suitable tonicity modifier. Glycerol is most frequently used as a tonicity modifier. Alternative tonicity modifying agents include xylitol, mannitol and sorbitol. The pharmaceutical compositions are typically formulated to be at physiologically neutral pH, typically in the range 6.0-8.5. The pH can be adjusted by the addition of base, for example, NaOH or NaHCO3, or in some cases acid, such as HCl.

The compositions of the technology can be formulated with pharmaceutically safe oil-water emulsions comprising a vegetable oil, a phosphatide emulsifier, typically egg lecithin or soybean lecithin, and a tonicity modifier such as, for example, Liposyn® II and Liposyn® III (Abbott Laboratories, North Chicago, Ill.) and Intralipid® (Fresenius Kabi AB, Uppsala, Sweden) or other similar oil-water emulsions.

Compounds of the present invention may exist in prodrug form. As used herein, "prodrug" is intended to include any carriers which release the active parent drug or compounds that are metabolized in vivo to an active drug or other compounds employed in the methods of the invention in vivo when such prodrug is administered to a subject. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkyl aryl esters such as methyl, ethyl, propyl, iso-propyl, butyl, isobutyl, sec-butyl, tertbutyl, cyclopropyl, phenyl, benzyl, and phenethyl esters, and the like.

As used herein, the term "pharmaceutically-acceptable salts" refers to the inorganic and organic salts, conventional nontoxic salts or quaternary ammonium salts of a therapeutic agent or compound or prodrug, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, adipic, aspartic, carbonic, gluconic, glucuronic, malonic, oleic, pamoic and the like. See, for example, Berge et al., "Pharmaceutical Salts", J. Pharm. Sci. 66:1-19 (1977) or P. H. Stahl and C. G. Wermuth, editors, Handbook of Pharmaceutical Salts: Properties, Selection and Use, Weinheim/Zürich:Wiley-VCH/VHCA, 2002, content of which is herein incorporated by reference in its entirety. The terms "salt" or "salts" is used interchangeably with "pharmaceutically acceptable salts".

In some embodiments of the aspects described herein, representative salts include hydrobromide, hydrochloride, sulfate, bisulfate, phosphate, nitrate, acetate, succinate, valerate, oleate, palmitate, stearate, laurate, benzoate, lactate, tosylate, citrate, maleate, fumarate, succinate, tartrate, napthylate, mesylate, monohydrogenphosphate, glucoheptonate, lactobionate, laurylsulphonate, pyrophosphate, pyrosulfate, and sodium salts and the like.

It is contemplated that the therapeutic agents of the technology described herein can be administered together with any other therapy effective against one of the cancers, neurodegenerative disorders, or autoimmune disorders described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one compound having the structure of Formula I and at least one additional pharmaceutical agent.

In some embodiments the pharmaceutical compositions of the technology described herein can comprise at least one compound having the structure of Formula I and at least one Bruton's Tyrosine Kinase (BTK) inhibitor agent. BTK has been shown to be an inhibitor of the Fas/APO-1 (CD-95) death inducing signaling complex (DISC) in B-lineage lymphoid cells (Vassilev et al., J. Biol. Chem. 1998, 274, 1646-1656). BTK inhibitors result in reduction of lymph node tumor burden, but elevate circulating tumor burden. Genetic chemotherapy is effective in treating circulating tumor cells, and thus may be effective in combination with BTK inhibitors in controlling both lymph node and circulating disease It has also been discovered that BTK inhibitors are useful as chemosensitizing agents, and, thus, are useful in combination with genetic chemotherapy. Exemplary BTK inhibitor agents include ibrutinib (PCI-32765; 1-[(3R)-3-[4-amino-3-(4-phenoxyphenyl)pyrazolo[3,4-d]pyrimidin-1-yl]piperidin-1-yl]prop-2-en-1-one); AVL-291; AVL-292; PCI-45292; 6-phenyl-imidazo(1,2-a)pyridine; 6-phenyl-imidazo(1,2-b)pyridazine derivatives as described in U.S. Pat. No. 8,324,211; pyridinone and pyridazinone derivatives as described in U.S. Pat. No. 8,318,719; 3-amino-5-phenyl-1H-pyridin-2-one derivatives as described in U.S. Pat. No. 8,299,077; 1H-pyrazolo(3,4-d) pyrimidin-4-ylamine substitutes as described in U.S. Pat. No. 8,232,280; 3-phenyl-1H-pyrazolo-pyrimidin-4-ylamine substitutes as described in U.S. Pat. No. 8,236,812; compounds as described in U.S. Pat. Nos. 7,393,848; 7,405,295; 7,514,444; 7,625,880; 7,683,064; 7,732,454; 7,741,330; 7,825,118; 7,902,194; 7,906,509; 7,943,618; 7,960,396; 8,008,309; 8,067,395; 8,088,781; 8,124,604; US20130018032; US20130018060, and US20130035334, the disclosures of which are incorporated herein by reference thereto.

In some embodiments the pharmaceutical compositions of the technology described herein can comprise at least one compound having the structure of Formula I and at least one Bcl-2 inhibitor agent. Bcl-2 inhibitors are pro-apoptotic and, when administered in combination with a DSB repair inhibitor, may further enhance the cancer apoptotic effect. Exemplary Bcl-2 inhibitor agents include ABT-199 (GDC-0199), navitoclax (ABT-263; (R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3-((trifluoromethyl)sulfonyl)phenyl)sulfonyl)benzamide), ABT-737 (Benzamide, 4-[4-[(4'-chloro[1,1'-biphenyl]-2-yl) methyl]-1-piperazinyl]-N-[[4-[[(1R)-3-(dimethylamino)-1-[(phenylthio)methyl]propyl]amino]-3-nitrophenyl]sulfonyl]-), obatoclax (GX15-070; 2-(2-((3,5-Dimethyl-1H- pyrrol-2-yl)methylene)-3-methoxy-2H-pyrrol-5-yl)-1H-indole), and TW-37 (5-(2-isopropylbenzyl)-N-(4-(2-tert-butylphenylsulfonyl)phenyl)-2,3,4-trihydroxybenzamide).

In some embodiments the pharmaceutical compositions of the technology described herein can comprise at least one compound having the structure of Formula I and at least one Chk1 inhibitor agent. Chk1 is an ATP-dependent serine-threonine kinase and a key component in the DNA replication-monitoring checkpoint system activated by double-stranded breaks (DSBs). Chk1 contributes to all currently defined cell cycle checkpoints, including G1/S, intra-S-phase, G2/M, and the mitotic spindle checkpoint. As used herein, Chk1 inhibitors are compounds that are capable of at least partially abrogating at least one cell cycle checkpoint activity of the Chk1 protein. Combination treatment with a DNA repair inhibitor and Chk1 inhibitor could result in synergistic cell arrest or killing. Exemplary Chk1 inhibitor agents include AZD7762 (1-(2-((S)-piperidin-3-ylcarbamoyl)-5-(3-fluorophenyl)thiophen-3-yl)urea), LY2603618 (IC-83; (S)-1-(5-bromo-4-methyl-2-(morpholin-2-yl-methoxy)phenyl)-3-(5-methylpyrazin-2-yl)urea), CHIR-124 ((S)-3-(1H-benzo[d]imidazol-2-yl)-6-chloro-4-(quinuclidin-3-ylamino)quinolin-2(1H)-one), SCH900776 (6-bromo-3-(1-methyl-1H-pyrazol-4-yl)-5-((R)-piperidin-3-yl)pyrazolo[1,5-a]pyrimidin-7-amine), and PF 477736 (Cyclohexaneacetamide, α-amino-N-[5,6-dihydro-2-(1-methyl-1H-pyrazol-4-yl)-6-oxo-1H-pyrrolo[4,3,2-ef][2,3]benzodiazepin-8-yl]-, (αR)—), UCN-01 (KW-24101; 7-Hydroxystaurosporine; from Kyowa Hakko Kogyo Co., Ltd., Tokyo, Japan and Keryx Biopharmaceuticals, Inc., New York, N.Y.), Lilly/ICOS IC83/LY2603618 (from Eli Lilly, Indianapolis, Ind.), XL-844 (EXEL-9844 from Exelixis), PF-394691 (from Pfizer), PF-473336 (from Pfizer) and compounds as described in U.S. Pat. Nos. 8,093,244; 7,560,462; 7,550,477; 7,501,435, 7,485,649, US 2007/0083044, US 2007/0082900, US 2007/0105864 and US 2007/0117804, the disclosures of which are incorporated herein by reference thereto.

In some embodiments the pharmaceutical compositions of the technology described herein can comprise at least one compound having the structure of Formula I and at least one MDM2 inhibitor agent. The term "a MDM2 inhibitor", as used herein, relates to a compound which targets, decreases or inhibits the interaction of MDM2 and the p53 tumor suppressor. An example of a MDM2 inhibitor includes, but is not limited to, trans-4-iodo, 4'-boranyl-chalcone; Nutlin-3 (4-(4,5-bis(4-chlorophenyl)-2-(2-isopropoxy-4-methoxyphenyl)-4,5-dihydro-1H-imidazole-1-carbonyl)piperazin-2-one); NSC-207895 (XI-006; 2,1,3-Benzoxadiazole, 4-(4-methyl-1-piperazinyl)-7-nitro-, 3-oxide); RG7112 (nutlin-3a); cis-imidazoline analogs known as nutlins (nutlin-1, nutlin-2, nutlin-3) and compounds as described in U.S. Pat. Nos. 7,737,174; 8,288,377; 8,222,288; 7,834,016; US20110319378; and WO2012121662, the disclosures of which are incorporated herein by reference thereto.

In some embodiments the pharmaceutical compositions of the technology described herein can comprise at least one compound having the structure of Formula I and at least one WEE1 inhibitor agent. A Wee 1 kinase is a tyrosine kinase that participates in the G2 checkpoint of a cell cycle. Wee1 phosphorylates Cdc2(Cdk1) tyrosine 15 that takes part in the progress to the M stage from the G2 stage in a cell cycle, thereby inactivating Cdc2 and temporarily stopping the cell cycle at the G2 stage (McGowan and Russell 1993 The EMBO Journal, 12, 75-85). It has been reported that the Wee 1 expression reduction by RNA interference or the Wee 1 inhibition by compounds may increase the sensitivity of cancer cells to adriamycin, X ray and gamma ray (Wang et al. 2004, Cancer Biology & Therapy, 3, 305-313; Wang et al. 2001, Cancer Research, 61, 8211-8217). The treatment with a DNA repair inhibitor combined with a Chk1 inhibitor could result in enhanced sensitivity of cancer cell to the treatment. It is considered that a Wee 1 inhibitor may inhibit the G2 checkpoint function of p53-depleted cancer cells, thereby enhancing the sensitivity of the cells to a DSB repair inhibitor. Exemplary WEE1 inhibitor agents include MK-1775 (2-allyl-1-(6-(2-hydroxypropan-2-yl)pyridin-2-yl)-6-(4-(4-methylpiperazin-1-yl)phenylamino)-1,2-dihydropyrazolo[3,4-d]pyrimidin-3-one); PD0166285 (6-(2,6-Dichlorophenyl)-2-[[4-[2-(diethylamino)ethoxy]phenyl]amino]-8-methylpyrido[2,3-d]pyrimidin-7(8H)-one dihydrochloride), and compounds as described in US Application 2005/0250836, WO2003/091255, each of which is herein incorporated by reference in its entirety.

In some embodiments the pharmaceutical compositions of the technology described herein can comprise at least one compound having the structure of Formula I and at least one poly ADP ribose polymerase (PARP) inhibitor agent. Poly (ADP-ribose)polymerase (PARP) or poly(ADP-ribose)synthase (PARS) has an essential role in facilitating DNA repair, controlling RNA transcription, mediating cell death, and regulating immune response. PARP inhibitors effectively target cells with reduced capacity for homologous recombination repair, such as BRCA1 or BRCA2-defective breast or ovarian cancer. Treatment with a DSB repair inhibitor may render cells with intact homologous recombination susceptible to PARP inhibitors, may enhance the efficacy of PARP inhibitors in homologous recombination deficient cancers, and may circumvent cases of acquired resistance to PARP inhibitors. An example of a PARP inhibitor includes, but is not limited to Iniparib (BSI 201; 4-iodo-3-nitrobenzamide), Olaparib (AZD-2281; KU-59436; 4-[(3-[(4-cyclopropylcarbonyl)piperazin-4-yl]carbonyl)-4-fluorophenyl]methyl(2H)phthalazin-1-one), Rucaparib (AGO 14699, PF-01367338; 2-{4-[(methylamino)methyl]phenyl}-1,3,4,5-tetrahydro-6H-azepino[5,4,3-cd]indol-6-one), Veliparib (ABT-888; 2-((R)-2-Methylpyrrolidin-2-yl)-1H-benzimidazole-4-carboxamide); CEP-8983; CEP-9722; MK-4827 (Niraparib; 2-{4-[(3S)-Piperidin-3-yl]phenyl}-2H-indazole-7-carboxamide); BMN-673 (LT-673; (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one); LT-674; LT-628; 3-aminobenzamide (INO-1001; 3-AB); PD128763 (3,4-dihydro-5-methyl-1(2H)-isoquinolinone); NU1025(8-Hydroxy-2-methyl-4(3H)-quinazolinone); DR 2313 (1,5,7,8-Tetrahydro-2-methyl-4H-thiopyrano[4,3-d]pyrimidin-4-one); UPF 1069 (5-(2-Oxo-2-phenylethoxy)-3,4-dihydroisoquinolin-1(2H)-one); EB 47 (5'-Deoxy-5'-[4-[2-[(2,3-Dihydro-1-oxo-1H-isoindol-4-yl)amino]-2-oxoethyl]-1-piperazinyl]-5'-oxoadenosine dihydrochloride); E7016 (Benzopyrano[4,3,2-de]phthalazin-3(2H)-one, 10-[(4-hydroxy-1-piperidinyl)methyl]-); 4-HQN (4-(1H)-Quinazolinone); ABT-767 and compounds as described in Griffin et al 1998, J. Med. Chem. 41, 5247; Skalitzky et al. 2003, J. Med. Chem. 46:210-213; Zaremba et al. 2007, Anti-Cancer Agents in Medicinal Chemistry 7, 515; Lewis et al. 2007, Curr Opin. Investigational Drugs 8, 1061; Guha 2011, Nature Biotechnology 29, 373-374; Rouleau et al. 2010, Nature Reviews Cancer 10, 293-301; Miknyoczki et al., 2007 Mol Cancer Ther, 6 (8), 2290-2302; Pellicciari et al. 2008, Chem. Med. Chem 3, 91; Jones et al., 2009, J Med Chem, 52(22), 7170-7185; Mason et al. 2008, Invest New Drugs, 26(1),1-5; Ferraris et al., 2010, J. Med. Chem. 53 4561; US patent applications: US2006/0229289;

US20070259937; US20120309717; US20130011365; US patents: U.S. Pat. Nos. 8,372,987; 8,362,030; 8,236,802; 8,217,070; 8,183,250; 8,088,760; international patent applications: WO 01/85686; WO 00/42040; WO 00/39070; WO 00/39104; WO 99/11623; WO 99/11628; WO 99/11622; WO 99/59975; WO 99/11644; WO 99/11945; WO 99/11649; and WO 99/59973, each of which is herein incorporated by reference in its entirety.

It is contemplated that the therapeutic agents of the technology described herein can be administered together with any other therapy effective against one of the autoimmune disorder described herein. It is contemplated that the therapeutic agents of the technology described herein can be administered together with any other therapy effective against one of the autoimmune disorders described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one compound having the structure of Formula I and at least one additional pharmaceutical agent.

In some embodiments the pharmaceutical compositions of the technology described herein can comprise at least one compound having the structure of Formula I and at least one interleukin-1 receptor-associated kinase 4 (IRAK-4) inhibitor agent. An example of an IRAK-4 inhibitor includes, but is not limited to ND-346, ND-2110 and ND-2158 (Nimbus Discovery), and compounds as described in Kim et al., J. Exp. Med. 2007 204(5), 1025-1036; Lebakken et al., J. Biomol. Screen. 2007, 12(6), 828-841; Maschera et al., Biochem. J. 1999, 339, 227-231; Song et al., Mol. Immunol. 2009, 46, 1458-1466; US Application US20120283238; U.S. Pat. No. 8,293,923, each of which is herein incorporated by reference in its entirety.

The dosage can be determined by a physician and adjusted, as necessary, to suit observed effects of the treatment. Generally, the compositions are administered so that the compound having the structure of Formula I is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. It is to be further understood that the ranges intermediate to the given above are also within the scope of this technology described herein, for example, in the range 1 mg/kg to 10 mg/kg, dose ranges such as 2 mg/kg to 8 mg/kg, 3 mg/kg to 7 mg/kg, 4 mg/kg to 6 mg/kg etc.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compound having the structure of Formula I. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more. The desired dose can be administered using continuous infusion or delivery through a controlled release formulation. In that case, the compound having the structure of Formula I contained in each sub-dose must be correspondingly smaller in order to achieve the total daily dosage. The dosage unit can also be compounded for delivery over several days, e.g., using a conventional sustained release formulation which provides sustained release of the compound having the structure of Formula I over a several day period. Sustained release formulations are well known in the art and are particularly useful for delivery of agents at a particular site, such as could be used with the agents of the technology described herein. In this embodiment, the dosage unit contains a corresponding multiple of the daily dose.

Before administration of a full dose a compound having the structure of Formula I, patients can be administered a smaller dose, such as a 5% infusion, and monitored for adverse effects, such as an allergic reaction. Owing to the effects on a cancer, neurodegeneration, or autoimmunity, a compound having the structure of Formula I or a pharmaceutical composition prepared there from can enhance the quality of life.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the compound. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

In some embodiments, pharmaceutical compositions can include (a) one or more compounds having the structure of Formula I and (b) one or more pharmaceutically effective compounds as described herein.

The dosage ranges for the administration of a compound having the structure of Formula I, according to the methods described herein depend upon, for example, the form of the compound having the structure of Formula I, its potency, and the extent to which symptoms, markers, or indicators of a condition described herein are desired to be reduced, for example the percentage reduction desired for symptoms. The dosage should not be so large as to cause adverse side effects, such as off-target cell death. Generally, the dosage will vary with the age, condition, and sex of the patient and can be determined by one of skill in the art. The dosage can also be adjusted by the individual physician in the event of any complication.

The efficacy of a compound having the structure of Formula I in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. survival. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed.

In vitro and animal model assays are provided herein which allow the assessment of a given dose of a compound. The efficacy of a given dosage combination can be assessed in an animal model, e.g. a xenotransplanted murine model of cancer. The mouse can be implanted and/or injected with tumor cells and subsequently administered a dose of the compound having the structure of Formula I. Efficacy can be assessed by, e.g., tumor growth, tumor size, and/or survival.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred. Murine genetics have generated a number of mouse models for the study of compounds such as those described herein. Such models can be used for in vivo testing of the presently described compounds, as well as for determining a therapeutically effective dose. A suitable mouse model is, for example, the AICDA−/− mouse described herein or model developed using patient derived tissue xenografting (PDX). In certain embodiments of this technique that would be useful in the study DSB repair inhibitors, an immunocompromised mouse strain, such as Nod-scid, NSG (NOD-scid Il2ry-null; NOD.Cg-Prkdc-scid<Il2rg>/Wjl/SzJ) or NRG (NOD-RagIl2ry-null; NOD-Rag1<null>IL2rg<null>/Wjl/SzJ) is engrafted with primary human cancer cells, such as leukemias.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels of a compound in plasma can be measured, for example, by high performance liquid chromatography. The effects of any particular dosage can be monitored by a suitable bioassay.

The amount of a compound which can be combined with a carrier material to produce a single dosage form will generally be that amount of the compound which produces a therapeutic effect. Generally out of one hundred percent, this amount will range from about 0.1% to 99% of compound, preferably from about 5% to about 70%, most preferably from 10% to about 30%.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the compounds described herein can be made using conventional methodologies or on the basis of in vivo testing using an appropriate animal model, as described elsewhere herein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g. cancer, autoimmune disease, and/or neurodegenerative disease. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "expression" refers to the cellular processes involved in producing RNA and proteins and as appropriate, secreting proteins, including where applicable, but not limited to, for example, transcription, translation, folding, modification and processing. The terms "expression product" or "expression products" include RNA transcribed from a gene, and polypeptides obtained by translation of mRNA transcribed from a gene. In some embodiments, an expression product is transcribed from a sequence that does not encode a polypeptide, such as a microRNA or RNAi.

As used herein, the term "B cell" refers to lymphocytes that play a role in the humoral immune response and is a component of the adaptive immune system. In this application the expressions "B cell", "B-cell" and "B lymphocyte" refer to the same cell.

Immature B cells are produced in the bone marrow of most mammals. After reaching the IgM+ immature stage in the bone marrow, these immature B cells migrate to lymphoid organs, where they are referred to as transitional B cells, some of which subsequently differentiating into mature B lymphocytes. B-cell development occurs through several stages, each stage characterized by a change in the genome content at the antibody loci.

Each B cell has a unique receptor protein (referred to as the B-cell receptor (BCR)) on its surface that is able to bind to a unique antigen. The BCR is a membrane-bound immunoglobulin, and it is this molecule that allows to distinguish B cells from other types of lymphocytes, as well as playing a central role in B-cell activation in vivo. Once a B cell encounters its cognate antigen and receives an additional signal from a T helper cell, it can further differentiate into one of two types of B cells (plasma B cells and memory B cells). The B cell may either become one of these cell types directly or it may undergo an intermediate differentiation step, the germinal center reaction, during which the B cell hypermutates the variable region of its immunoglobulin gene ("somatic hypermutation") and possibly undergoes class switching.

Plasma B cells (also known as plasma cells) are large B cells that have been exposed to an antigen and are producing and secreting large amounts of antibodies. These are short-lived cells and usually undergo apoptosis when the agent that induced the immune response is eliminated. Memory B cells are formed from activated B cells that are specific to an antigen encountered during a primary immune response. These cells are able to live for a long time, and can respond quickly following a second exposure to the same antigen.

The term "blood cell" as used herein refers to a cell found in the blood, e.g. red blood cells, white blood cells, platelets, neutrophils, eosinophils, basophils, lymphocytes, and/or monocytes.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, the term "alkyl" means a straight or branched, saturated aliphatic radical having a chain of carbon atoms. The term "alkyl" includes cycloalkyl or cyclic alkyl. $C_x$ alkyl and $C_x$–$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., $(C_6$-$C_{10})$aryl$(C_0$-$C_3)$alkyl includes phenyl, benzyl, phenethyl, 1-phenylethyl 3-phenylpropyl, and the like. Backbone of the alkyl can be optionally inserted with one or more heteroatoms, such as N, O, or S. Examples of alkyl radicals include, but are not limited to, methyl, ethyl, propyl, isopropyl, n-butyl, tert-butyl, neopentyl, n-hexyl, and n-octyl radicals.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$—$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$—$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine. A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$—$C_y$cylcyl are typically used where X and Y indicate the number of carbon atoms in the ring system. The cycloalkyl group additionally can be optionally substituted, e.g., with 1, 2, 3, or 4 substituents. Examples of cyclyl groups include, without limitation, cyclopropyl, cyclobutyl, cyclopentyl, cyclopentenyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$—$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies. As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

The term "aryl" refers to monocyclic, bicyclic, or tricyclic fused aromatic ring system. $C_x$ aryl and $C_x$—$C_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$—$C_y$heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3cj]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

As used herein, the term "substituted" refers to independent replacement of one or more of the hydrogen atoms on the substituted moiety with substituents independently selected from, but not limited to, alkyl, alkenyl, heterocycloalkyl, alkoxy, aryloxy, hydroxy, amino, amido, alkylamino, arylamino, cyano, halo, mercapto, nitro, carbonyl, acyl, aryl and heteroaryl groups.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O— alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like. The term "alkoxycarbonyl" means —C(O)O-(alkyl), such as —C(=O)OCH$_3$, —C(=O)OCH$_2$CH$_3$, and the like. The term "alkoxyalkyl" means -(alkyl)-O-(alkyl), such as —CH$_2$OCH$_3$, —CH$_2$OCH$_2$CH$_3$, and the like. The term "aryloxy" means —O-(aryl), such as —O-phenyl, —O-pyridinyl, and the like. The term "arylalkyl" means -(alkyl)-(aryl), such as benzyl (i.e., —CH$_2$phenyl), —CH$_2$-pyrindinyl, and the like. The term "arylalkyloxy" means —O-(alkyl)-(aryl), such as —O-benzyl, —O—CH$_2$-pyridinyl, and the like. The term "cycloalkyloxy" means —O-(cycloalkyl), such as —O-cyclohexyl, and the like. The term "cycloalkylalkyloxy" means —O-(alkyl)-(cycloalkyl, such as —OCH$_2$cyclohexyl, and the like. The term "aminoalkoxy" means —O-(alkyl)-NH$_2$, such as —OCH$_2$NH$_2$, —OCH$_2$CH$_2$NH$_2$, and the like. The term "mono- or di-alkylamino" means —NH(alkyl) or —N(alkyl)(alkyl), respectively, such as —NHCH$_3$, —N(CH$_3$)$_2$, and the like. The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like. The term "arylamino" means —NH(aryl), such as —NH-phenyl, —NH-pyridinyl, and the like. The term "arylalkylamino" means —NH-(alkyl)-(aryl), such as —NH-benzyl, —NHCH$_2$-pyridinyl, and the like. The term "alkylamino" means —NH(alkyl), such as —NHCH$_3$, —NHCH$_2$CH$_3$, and the like. The term "cycloalkylamino" means —NH-(cycloalkyl), such as —NH-cyclohexyl, and the like. The term "cycloalkylalkylamino"-NH-(alkyl)-(cycloalkyl), such as —NHCH$_2$-cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH3) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The term "racemic mixture", "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); or (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F$_{(+)}$ and F$_{(−)}$ (where the sum of F$_{(+)}$ and F$_{(−)}$=1). The enantiomeric excess is defined as *F$_{(+)}$−F$_{(−)}$* and the percent enantiomeric excess by 100x*F$_{(+)}$−F$_{(−)}$*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer", "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer", "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity", also called the enantiomeric ratio indicated by the symbol "E", refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A compound of Formula I:

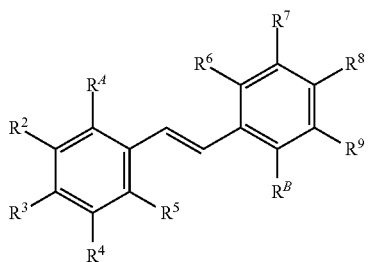

Formula I wherein:
- $R^A$ and $R^B$ are $SO_2N(R^{22})_2$, or $R^A$ and $R^B$ is $SO_3R^{23}$ and the other is hydrogen or $SO_3R^{23}$, or one of $R^A$ and $R^B$ is $SO_3^-Y^+$ and the other is hydrogen, or one of $R^A$ is $R^B$ is $CO_2^-Y^+$ and the other is hydrogen or $CO_2^-Y^+$, or one of $R^A$ and $R^B$ is $PO_3^-(Y^+)_2$ and the other is hydrogen or $PO_3^-(Y^+)_2$;
- $R^2$, $R^3$, $R^4$, $R^5$, $R^6$, $R^7$, $R^8$ and $R^9$ are independently hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{12})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl, provided that $R^3$ and $R^8$ are not the same;
- $R^{21}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl;
- $R^{22}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, or $C(O)(CH_2)_nCH_3$ wherein n=0, 1, 2, 3, 4, 5, 6.
- $R^{23}$ is independently for each occurrence optionally substituted linear or branched $C_1$-$C_{10}$ alkyl;
- $Y^+$ is for each occurrence a cation; and
pharmaceutically acceptable salts thereof.

2. The compound paragraph 1, wherein $R^3$ and $R^8$ are selected independently from the group consisting of hydrogen, hetercyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$, wherein $R^{21}$ is H or $C_1$-$C_4$alkyl and $R^{22}$ can be H or $C_1$-$C_{10}$ alkyl.

3. The compound of paragraph 1 or 2, wherein $R^3$ and $R^8$ are selected independently from the group consisting of hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, NHC(S)$NHCH_3$, $NHC(S)NHCH(CH_3)_2$, NHC(S)NH-cyclopropane, $NHC(O)NHCH_3$, $NHC(O)NHCH(CH_3)_2$, benzoxazolyl, and NHC(O)NH-cyclopropane.

4. The compound of any of paragraphs 1-3, wherein one of $R^3$ and $R^8$ is $NHC(O)CH_3$ and the other is $NHC(O)CH_3$ or $NHC(S)NHCH(CH_3)_2$.

5. The compound of any of paragraphs 1-4, wherein $R^3$ and $R^8$ are different.

6. The compound of any of paragraphs 1-5, wherein at least one of $R_2$, $R_4$, $R_5$, $R_6$, $R_7$, and $R_9$ is hydrogen.

7. The compound of any of paragraphs 1-6, wherein $R_2$, $R_4$, $R_5$, $R_6$, $R_7$, and $R_9$ all are hydrogen.

8. The compound of any of paragraphs 1-7, wherein $R^{22}$ is selected independently for each occurrence from the group consisting of hydrogen, methyl, ethyl, propyl, isopropyl, butyl, isobutyl, pentyl, t-butyl, and cyclopropyl; or the two $R^{22}$ together with the nitrogen they are attached to form an optionally substituted 3-8 membered heterocyclyl.

9. The compound of any of paragraphs 1-8, wherein $R^{23}$ is independently for each occurrence methyl, ethyl, propyl, isopropyl, butyl, isobutyl, pentyl, t-butyl, or cyclopropyl.

10. The compound of any of paragraphs 1-9, wherein $Y^+$ is selected independently for each occurrence from the group consisting of sodium, potassium, aluminum, calcium, lithium, magnesium, barium, zinc, ammonium, aminium, and any combinations thereof 11. The compound of any of paragraphs 1-10, wherein $R^A$ is $SO_3R^{23}$; $R^B$ is hydrogen or $SO_3R^{23}$; and each $R^{23}$ is independently isopropyl or t-butyl.

12. The compound of any of paragraphs 1-11, wherein $R^A$ is $SO_3R^{23}$; $R^B$ is hydrogen or $SO_3R^{23}$; and $R_2$, $R_4$, $R_5$, $R_6$, $R_7$, and $R_9$ are hydrogen.

13. The compound of any of paragraphs 1-12 wherein $R^A$ is $SO_3R^{23}$; $R^B$ is hydrogen or $SO_3R^{23}$; each $R^{23}$ is independently isopropyl or t-butyl; and $R_2$, $R_4$, $R_5$, $R_6$, $R_7$, and $R_9$ are hydrogen.

14. The compound of any of paragraphs 1-13, wherein one of $R^A$ and $R^B$ is $SO_3^-Y^+$ and the other is hydrogen; and one of $R^3$ and $R^8$ is $NHC(O)CH_3$ and the other is $NHC(S)NHCH(CH_3)_2$.

15. The compound of any of paragraphs 1-14, wherein one of $R^A$ and $R^B$ is $SO_3Y^+$ and the other is hydrogen; and $R_2$, $R_4$, $R_5$, $R_6$, $R_7$, and $R_9$ are hydrogen.

16. The compound of any of paragraphs 1-15, wherein one of $R^A$ and $R^B$ is $SO_3^-Y^+$ and the other is hydrogen; one of $R^3$ and $R^8$ is $NHC(O)CH_3$ and the other is $NHC(S)NHCH(CH_3)_2$; and $R_2$, $R_4$, $R_5$, $R_6$, $R_7$, and $R_9$ are hydrogen.

17. The compound of any of paragraphs 1-16, wherein one of $R^A$ and $R^B$ is $CO_2^-Y^+$ and the other is hydrogen or $CO_2^-Y^+$; and one of $R^3$ and $R^8$ is $NHC(O)CH_3$ and the other is $NHC(S)NHCH(CH_3)_2$.

18. The compound of any of paragraphs 1-17, wherein one of $R^A$ and $R^B$ is $CO_2^-Y^+$ and the other is hydrogen or $CO_2^-Y^+$; and $R_2$, $R_4$, $R_5$, $R_6$, $R_7$, and $R_9$ are hydrogen.

19. The compound of any of paragraphs 1-18, wherein one of $R^A$ and $R^B$ is $CO_2^-Y^+$ and the other is hydrogen or $CO_2^-Y^+$; one of $R^3$ and $R^8$ is $NHC(O)CH_3$ and the other is $NHC(S)NHCH(CH_3)_2$; and $R_2$, $R_4$, $R_5$, $R_6$, $R_7$, and $R_9$ are hydrogen.

20. The compound of any of paragraphs 1-19, wherein one of $R^A$ and $R^B$ is $PO_3^-Y^+$ and the other is hydrogen or PO$_3^-$Y$^+$; and one of R$^3$ and R$^8$ is NHC(O)CH$_3$ and the other is NHC(S)NHCH(CH$_3$)$_2$.

21. The compound of any of paragraphs 1-20, wherein one of R$^A$ and R$^B$ is PO$_3^-$Y$^+$ and the other is hydrogen or PO$_3^-$Y$^+$; and R$_2$, R$_4$, R$_5$, R$_6$, R$_7$, and R$_9$ are hydrogen.

22. The compound of any of paragraphs 1-21, wherein one of R$^A$ and R$^B$ is PO$_3^-$Y$^+$ and the other is hydrogen or PO$_3^-$Y$^+$; one of R$^3$ and R$^8$ is NHC(O)CH$_3$ and the other is NHC(S)NHCH(CH$_3$)$_2$; and R$_2$, R$_4$, R$_5$, R$_6$, R$_7$, and R$_9$ are hydrogen.

23. The compound of any of paragraphs 1-22, wherein the compound is selected from the group consisting of

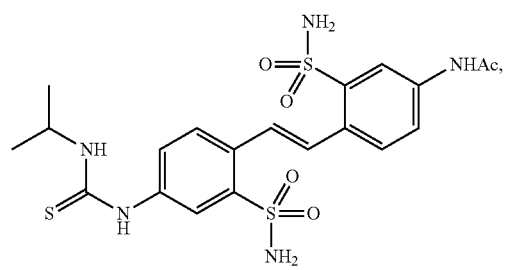

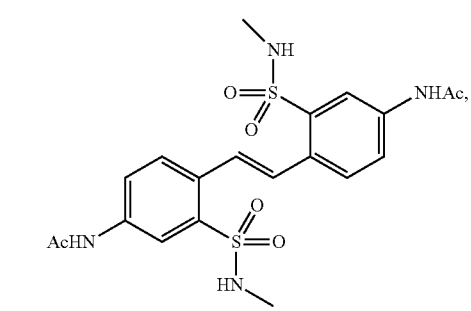

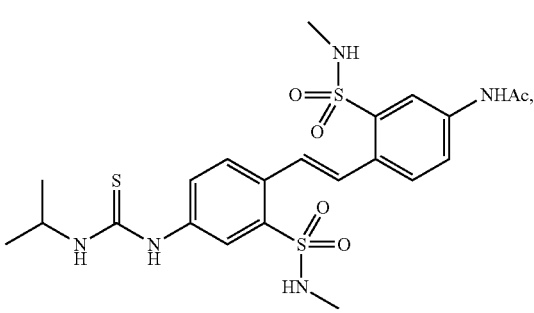

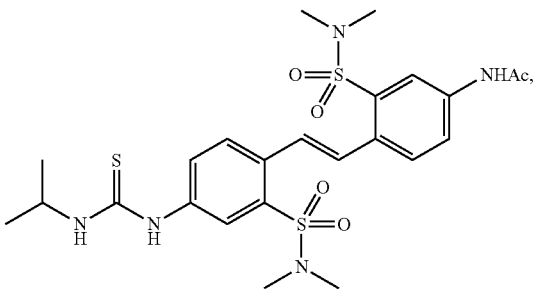

-continued

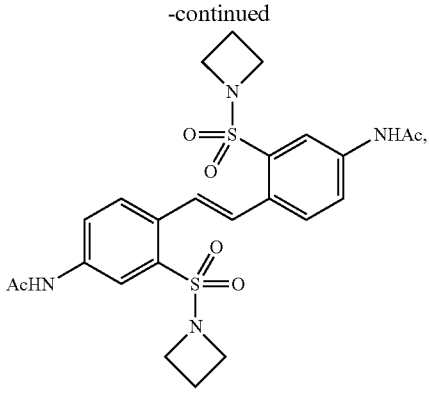

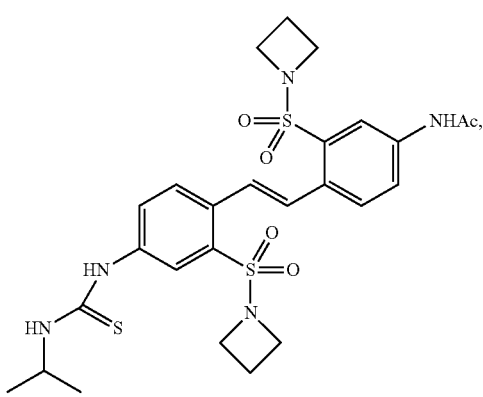

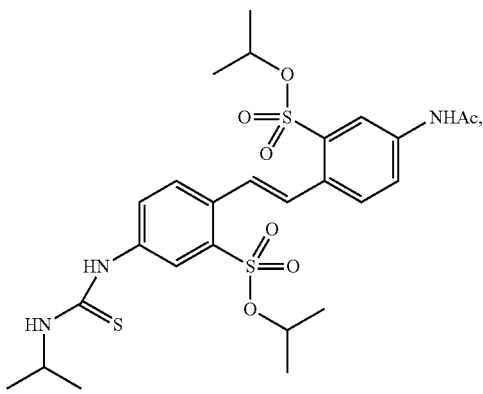

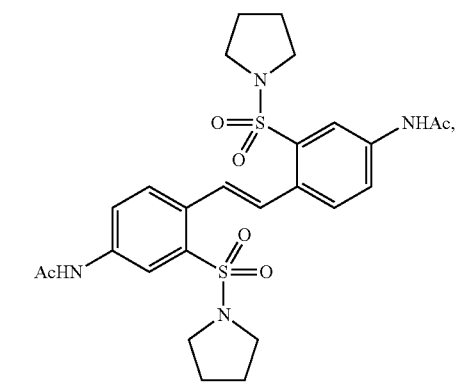

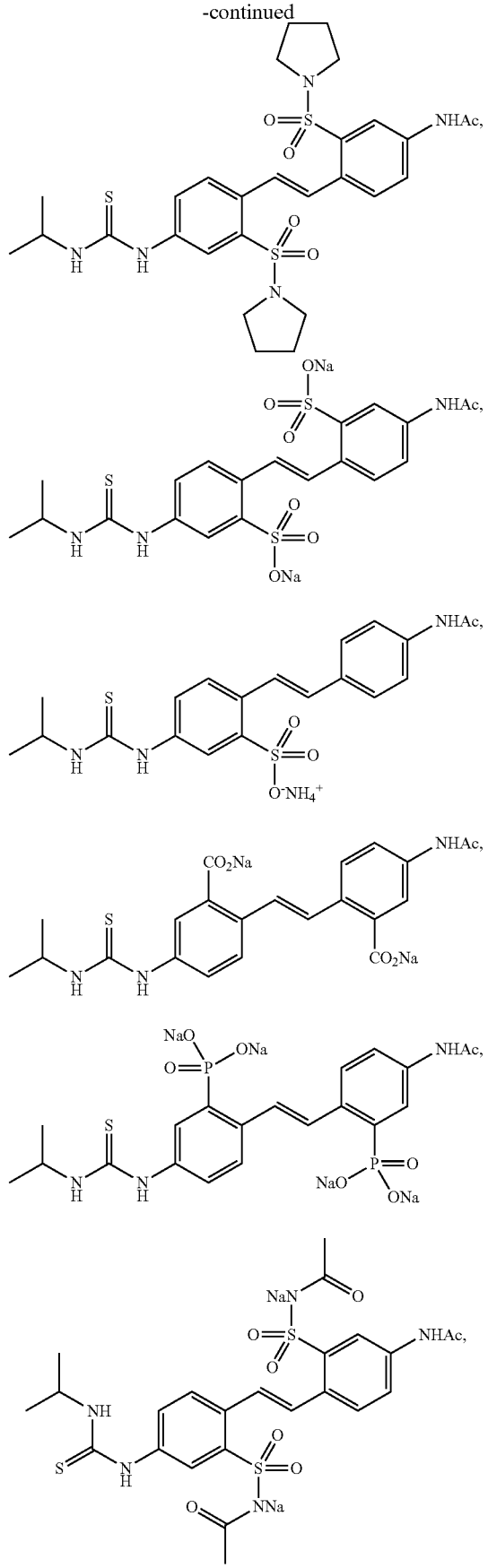
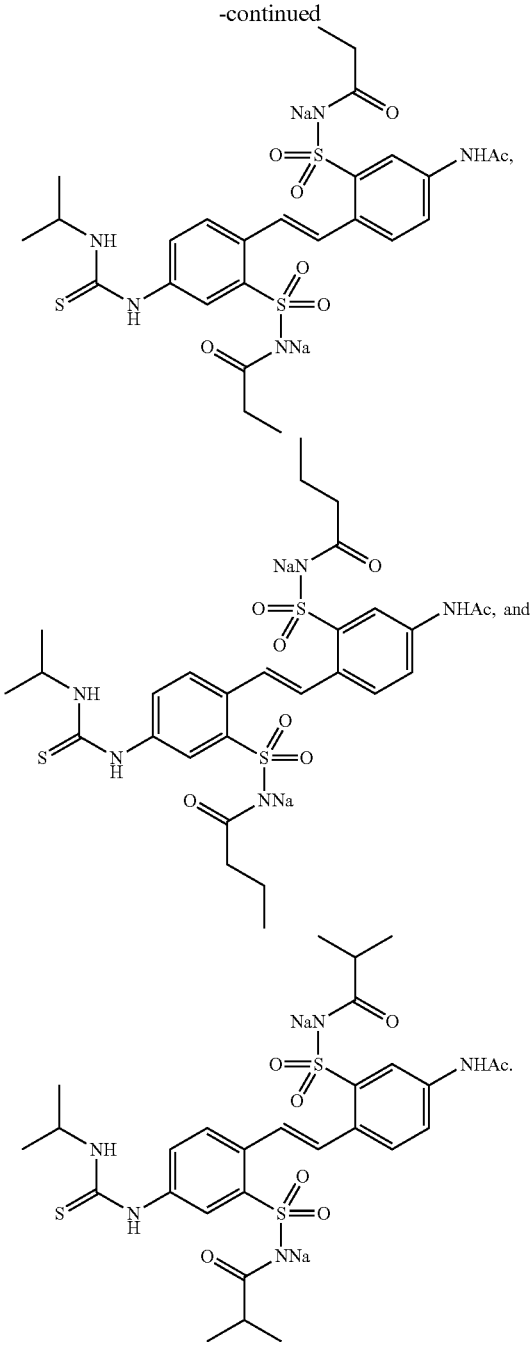

24. A method of treating cancer, autoimmune disease, immune deficiency, or neurodegenerative disease, the method comprising administering a therapeutically effective dose of a composition of any of paragraphs 1-23 to a subject in need of treatment for cancer, autoimmune disease, immune deficiency, or neurodegenerative disease.

25. The method of paragraph 24, wherein the subject is determined to have an increased level of DNA damage occurring in one or more cell types relative to a reference level.

26. The method of any of paragraphs 24-25, wherein the subject is determined to have an increased level of DNA damage occurring in a cell selected from the group consisting of:

a cancer cell; an immune cell; an autoimmune cell; or a nervous system cell.

27. The method of any of paragraphs 24-26, wherein the DNA damage is selected from the group consisting of: single-stranded DNA breaks, double-strand DNA breaks, and DNA mutations.

28. The method of any of paragraphs 24-27, wherein a subject is determined to have an increased level of DNA damage if the subject is determined to have an increased level and/or activity of a DNA damage process or DNA editing enzyme.

29. The method of paragraph 28, wherein the DNA editing enzyme is selected from the group consisting of: activation induced cytidine deaminase (AID or AICDA), APOBEC2, APOBEC3A, APOBEC3C, APOBEC3D, APOBEC3F, APOBEC3G, APOBEC3H, APOBEC4, a Type 1 Topoisomerase, a Type 2 Topoisomerase, Recombination Activating Gene 1 (RAG1), and Recombination Activating Gene 2 (RAG2).

30. The method of any of paragraphs 24-29, wherein a subject is determined to have an increased level of DNA damage if the subject has been exposed to a DNA damaging agent selected from the group consisting of: a viral infection with a DNA integrating virus; exposure to a DNA damaging chemical; exposure to a chemotherapeutic agent; and exposure to ionizing or ultraviolet radiation.

31. The method of any of paragraphs 24-30, wherein the DNA damage is a double strand break.

32. The method of any of paragraphs 24-31, wherein the DNA damage enzyme is activation-induced cytidine deaminase (AID).

33. The method of paragraph 24-32, wherein an increased level of AID is a detectable level of AID.

34. The method of any of paragraphs 24-33, wherein an increased level of AID is a level of AID which is statistically significantly higher than the level of AID expressed in unactivated B cells or a normal non-immune cell from a healthy subject 35. The method of any of paragraphs 24-34, wherein the level of AID is the level in a blood cell or B cell.

36. The method of any of paragraphs 24-35, wherein the cancer is selected from the group consisting of: lymphoma, leukemia, and a plasma cell neoplasm.

37. The method of paragraph 36, wherein the lymphoma is selected from the group consisting of: Non-Hodgkin's lymphoma; Burkitt's lymphoma, small lymphocytic lymphoma; lymphoplasmacytic lymphoma; MALT lymphoma; follicular lymphoma; diffuse large B-cell lymphoma; and T-cell lymphoma.

38. The method of paragraph 36, wherein the leukemia is selected from the group consisting of: acute lymphoblastic leukemia (ALL), Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).

39. The method of paragraph 36, wherein the plasma cell neoplasm is selected from the group consisting of: multiple myeloma; plasma cell myeloma; plasma cell leukemia; and plasmacytoma.

40. The method of any of paragraphs 24-35, wherein the subject has a cancer selected from the group consisting of:
epithelial cell cancer; colon cancer, liver cancer, gastric cancer; intestinal cancer; esophageal cancer; breast cancer; ovarian cancer; head and neck cancer; lung cancer; and thyroid cancer.

41. The method of any of paragraphs 24-35, wherein the autoimmune disease is selected from the group consisting of:
lupus erythematosus: Wiskott-Aldrich syndrome; autoimmune lymphoproliferative syndrome; myasthenia gravis; rheumatoid arthritis (RA); lupus nephritis; multiple sclerosis; systemic lupus erythematosis, discoid lupus, subacute cutaneous lupus erythematosus, cutaneous lupus erythematosus including chilblain lupus erythematosus, chronic arthritis, Sjogren's syndrome, inflammatory chronic rhinosinusitis, colitis, celiac disease, inflammatory bowel disease, Barrett's esophagus, inflammatory gastritis autoimmune nephritis, autoimmune vasculitis, autoimmune hepatitis, autoimmune carditis, autoimmune encephalitis, autoimmune diabetes, autoimmune diabetes nephritis, and autoimmune mediated hematological disease.

42. A composition of any of paragraphs 1-23 for use in the treatment of cancer, autoimmune disease, immune deficiency, or neurodegenerative disease in a subject.

43. The composition of paragraph 42, wherein the subject is determined to have an increased level of DNA damage occurring in one or more cell types relative to a reference level.

44. The composition of any of paragraphs 42-43, wherein the subject is determined to have an increased level of DNA damage occurring in a cell selected from the group consisting of:
a cancer cell; an immune cell; an autoimmune cell; or a nervous system cell.

45. The composition of any of paragraphs 42-44, wherein the DNA damage is selected from the group consisting of:
single-stranded DNA breaks, double-strand DNA breaks, and DNA mutations.

46. The composition of any of paragraphs 42-45, wherein a subject is determined to have an increased level of DNA damage if the subject is determined to have an increased level and/or activity of a DNA damage process or DNA editing enzyme.

47. The composition of paragraph 46, wherein the DNA editing enzyme is selected from the group consisting of:
activation induced cytidine deaminase (AID or AICDA), APOBEC2, APOBEC3A, APOBEC3C, APOBEC3D, APOBEC3F, APOBEC3G, APOBEC3H, APOBEC4, a Type 1 Topoisomerase, a Type 2 Topoisomerase, Recombination Activating Gene 1 (RAG1), and Recombination Activating Gene 2 (RAG2).

48. The composition of any of paragraphs 42-47, wherein a subject is determined to have an increased level of DNA damage if the subject has been exposed to a DNA damaging agent selected from the group consisting of:
a viral infection with a DNA integrating virus; exposure to a DNA damaging chemical; exposure to a chemotherapeutic agent; and exposure to ionizing or ultraviolet radiation.

49. The composition of any of paragraphs 42-48, wherein the DNA damage is a double strand break.

93

50. The composition of any of paragraphs 42-49, wherein the DNA damage enzyme is activation-induced cytidine deaminase (AID).
51. The composition of any of paragraphs 42-50, wherein an increased level of AID is a detectable level of AID.
52. The composition of any of paragraphs 42-41, wherein an increased level of AID is a level of AID which is statistically significantly higher than the level of AID expressed in unactivated B cells or a normal non-immune cell from a healthy subject
53. The composition of any of paragraphs 42-52, wherein the level of AID is the level in a blood cell or B cell.
54. The composition of any of paragraphs 42-53, wherein the cancer is selected from the group consisting of: lymphoma, leukemia, and a plasma cell neoplasm.
55. The composition of any of paragraphs 42-54, wherein the lymphoma is selected from the group consisting of: Non-Hodgkin's lymphoma; Burkitt's lymphoma, small lymphocytic lymphoma; lymphoplasmacytic lymphoma; MALT lymphoma; follicular lymphoma; diffuse large B-cell lymphoma; and T-cell lymphoma.
56. The composition of any of paragraphs 42-54, wherein the leukemia is selected from the group consisting of: acute lymphoblastic leukemia (ALL), Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).
57. The composition of any of paragraphs 42-54, wherein the plasma cell neoplasm is selected from the group consisting of:
multiple myeloma; plasma cell myeloma; plasma cell leukemia; and plasmacytoma.
58. The composition of any of paragraphs 42-54, wherein the subject has a cancer selected from the group consisting of:
epithelial cell cancer; colon cancer, liver cancer, gastric cancer; intestinal cancer; esophageal cancer; breast cancer; ovarian cancer; head and neck cancer; lung cancer; and thyroid cancer.
59. The composition of any of paragraphs 42-53, wherein the autoimmune disease is selected from the group consisting of:
lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, discoid lupus, subacute cutaneous lupus erythematosus, cutaneous lupus erythematosus including chilblain lupus erythematosus, chronic arthritis, Sjogren's syndrome, inflammatory chronic rhinosinusitis, colitis, celiac disease, inflammatory bowel disease, Barrett's esophagus, inflammatory gastritis autoimmune nephritis, autoimmune vasculitis, autoimmune hepatitis, autoimmune carditis, autoimmune encephalitis, autoimmune diabetes, autoimmune diabetes nephritis, and autoimmune mediated hematological disease.

EXAMPLES

Example 1

Figure 2:
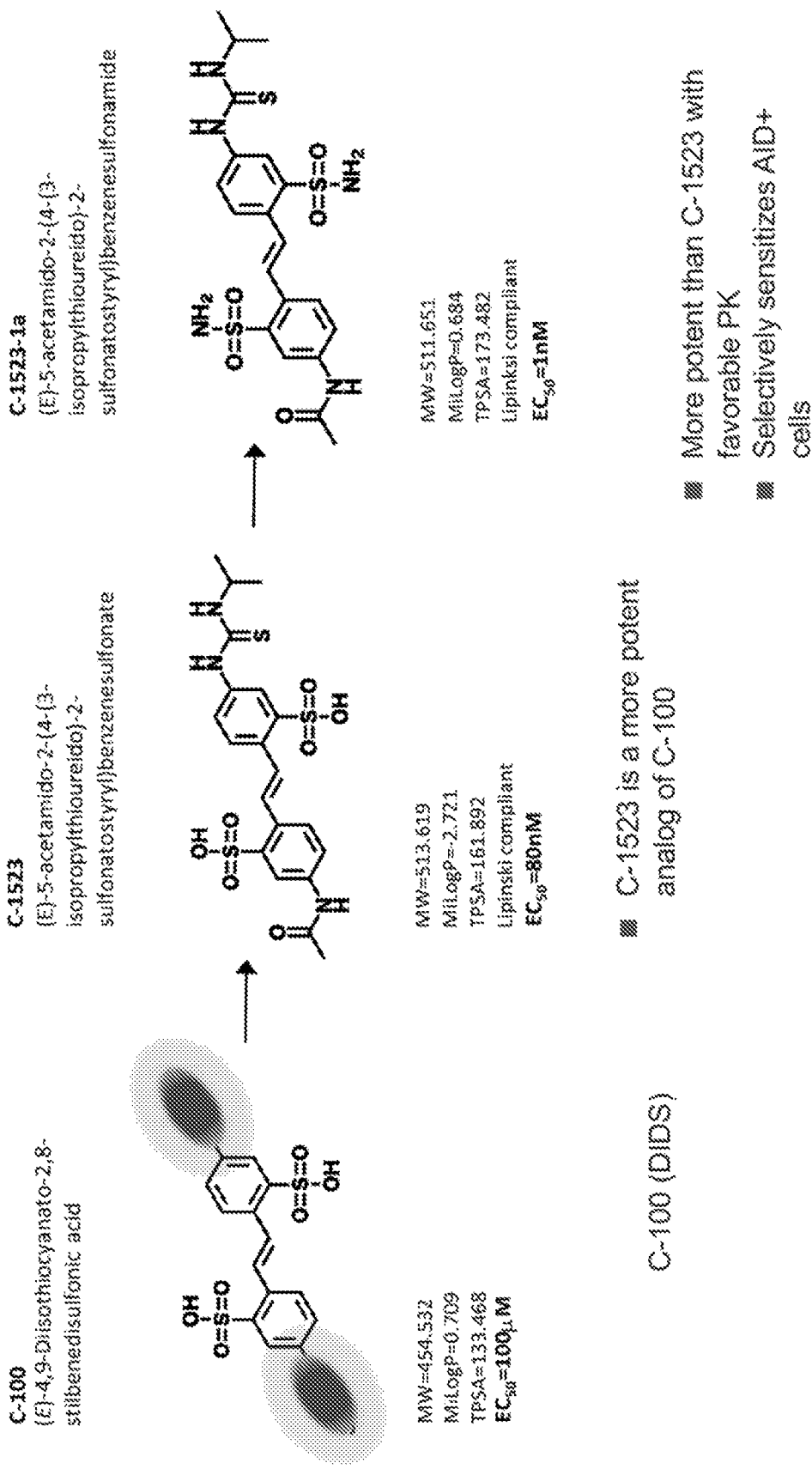
FIG. 2 depicts the structures and characterisitics of certain compounds described herein.

Derivatives of C-1523 (C-1523-1(a, b, b-1, c, c-1, d, e, f, f-1_, C-1523-2, C-1523-3, C-1523-4, C-1523-5)(FIG. 1) were synthesized. Isothiocyanate groups of DIDS ((E)-4,9-diisothiocyanato-2,8-stilbenes disulfonic acid) were modified to generate C-1523 ((E)-5-acetamido-2-(4-(3-isopropylthioureido)-2-sulfonatostyryl)benzenesulfonate. The Sulfonate groups of C-1523 ((E)-5-acetamido-2-(4-(3-isopropylthioureido)-2-sulfonatostyryl)benzenesulfonate were derivatize to produce C-1523-1A ((E)-5-acetamido-2-(4-(3-isopropylthioureido)-2-sulfonatostyryl)benzenesulfonamide (FIG. 2).

Figure 3:
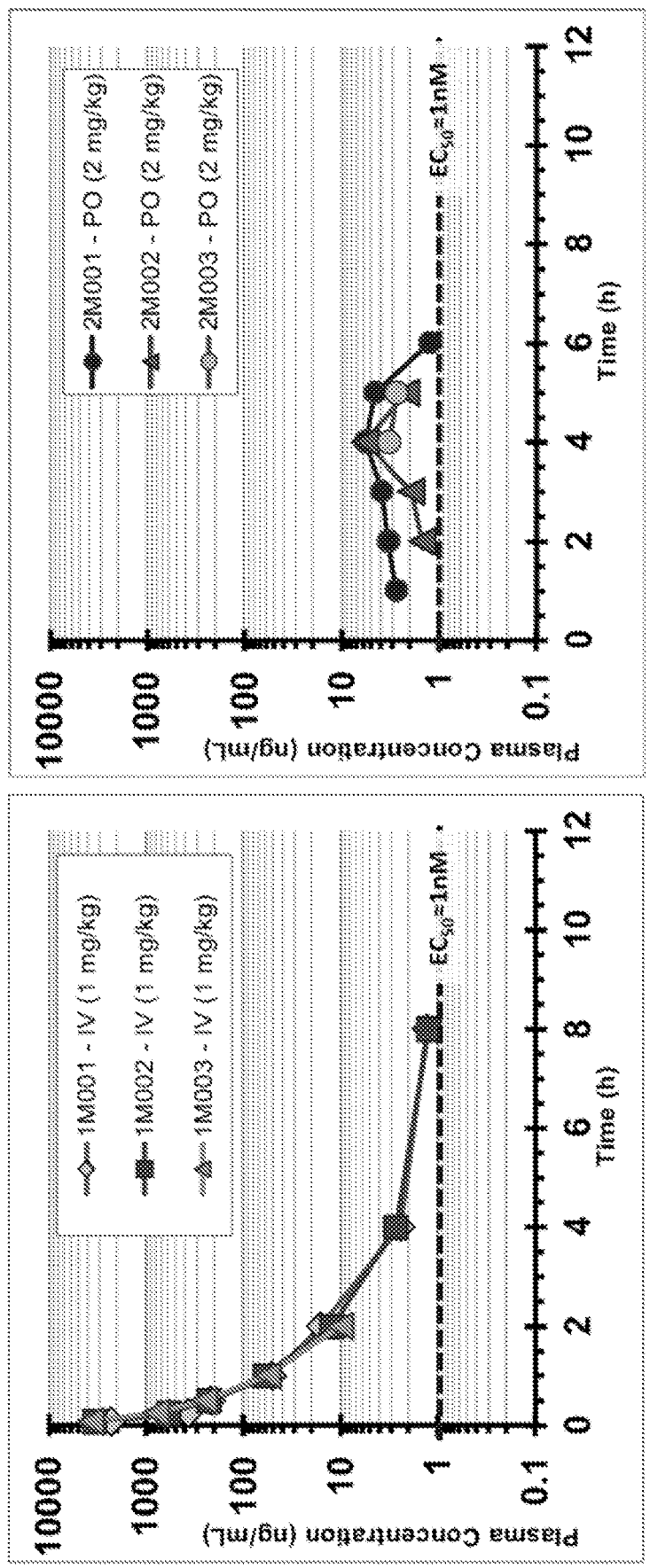
FIG. 3 depicts the bioavailability of C-1523-1A when delivered intravenously and orally.

C-1523-1A was formulated in PBS with 5% DMSO and given via single intravenous injection (1 milligram per kilogram) or by oral gavage to Sprague Dawley rats (2 milligrams per kilogram). Plasma concentrations were measure by mass spectrometry at t=15 min, t=30 min, t=1 hr, t=2 hr, t=4 hr, and t=8 hr for the intravenous cohort and at t=1 hr, t=2 hr, t=3 hr, t=4 hr, t=5 hr, t=6 hr. Plasma half life after iv injection is 1.5 hr; AUC=971 hr*ng/ml; Vss=0.29 L/kg, and Ct=17.7 ml/min/kg. Oral availability is 2-3% (FIG. 3).

Figure 7:
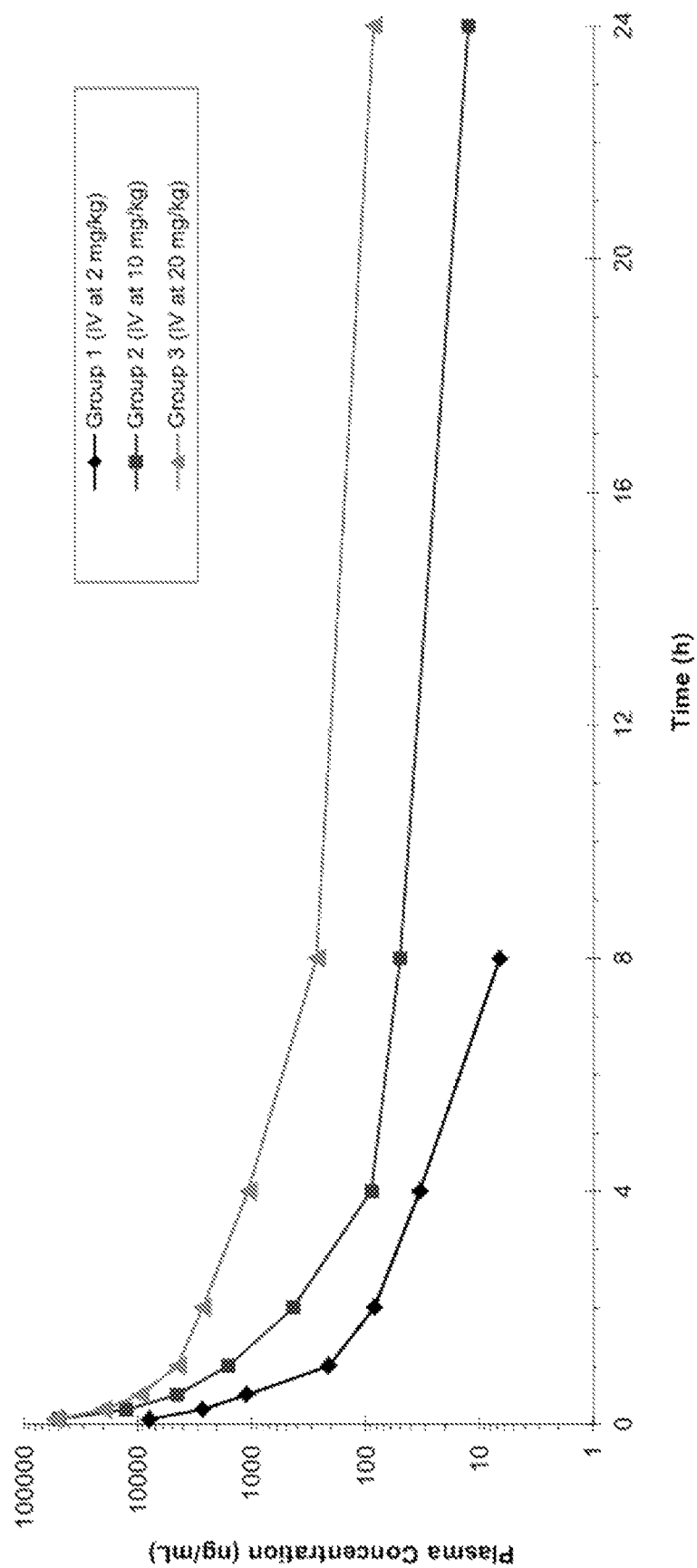
FIG. 7 depicts a graph of bioavailability (plasma concentration) of c-1523-1a when administered intravenously at various doses.

Pharmacokinetic measurements of DIDS, C-1523, and C-1523-1a following oral and intravenous administration to Sprague Dawly rats were made (FIGS. 4-6) and the plasma concentration of C-1523-1a at t=15 min, t=30 min, t=1 hr, t=2 hr, t=8 hr, and t=24 hr following administration of 2, 10, or 20 milligrams per kilogram to Sprague Dawley rats was determined (FIG. 7).

Primary AID-expressing B-cells were exposed to C-1523-1a at concentrations of 100 femtomolar, 1 picomolar, 10 picomolar, 100 picomolar, 1 nanomolar, 10 nanomolar, 100 nanomolar, 1 micromolar, and 10 micromolar ($10^{-4}$, $10^{-3}$, $10^{-2}$, $10^{-1}$, $10^{0}$, $10^{1}$, $10^{2}$, $10^{3}$, $10^{4}$ nanomola, respectively) for 4 days and viability of cells was determined (FIG. 8). Cell viability was also determined for human CLL cell lines MEC1 (pre-treatment) and MEC2 (Relapse) after exposure to Vehicle (PBS/5% DMSO), 100 picomolar, or 10 nanomolar C-1523-1a for 20 days in culture (FIG. 8, right panel).

Figure 9:
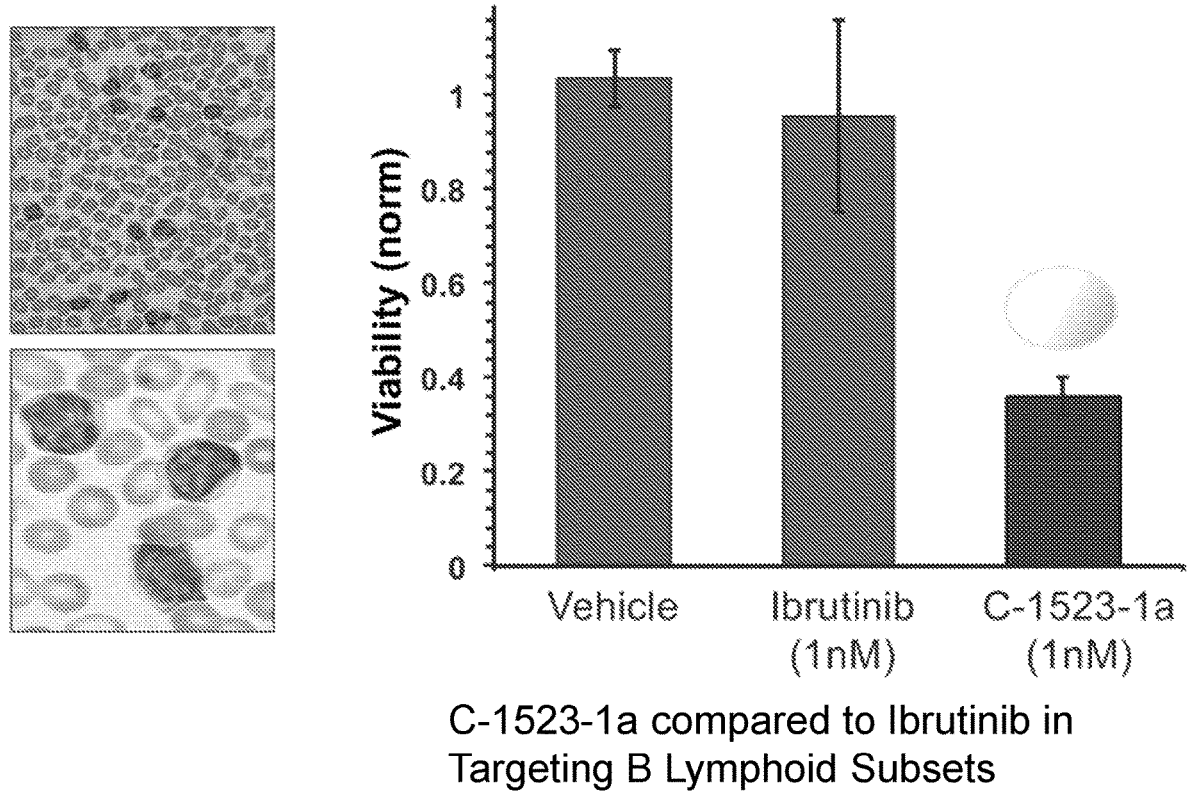

Primary splenic B-cells from AID-expressing mice were exposed to C-1523-1a and the BTK inhibitor ibrutinib and cell viability was compared to primary splenic B-cells in AID-negative mice (FIG. 9). C-1523-1a is surprisingly potent and selective for AID+ cells in this cell type.

Figures 10, 11:
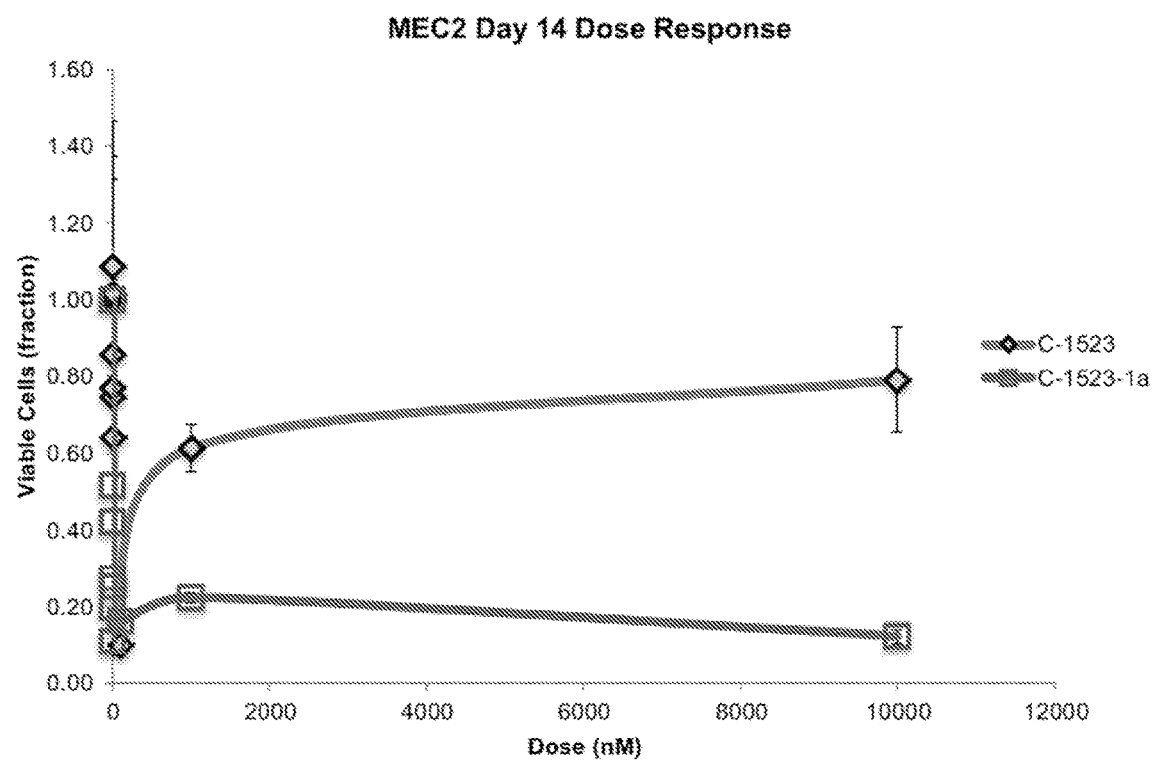

Dose responses for C-1523 (blue) and C-1523-1a (red) in primary B-cells (AID+) was determined (FIG. 10). C-1523 shows inverted dose response above 100 nM while C-1523-1a shows consistent response below 10 nM.

The urine excretion of C-1523-1a was also determined, after single intravenous administration of 1 milligram per kilogram to Sprague Dwley rats (FIG. 11).

Example 2: RAD51 Prevents DNA Damage Overload and Mitotic Catastrophe in Cells Expressing AID Targeted and selective therapeutics have significantly improved cancer treatment in the last two decades. Tumor-cell selective therapies exploit biological features unique to malignant cells and absent from non-malignant cells. In this context, activation-induced cytidine deaminase (AID), a DNA mutase normally restricted to stimulated B-lymphocytes, is aberrantly expressed in many tumor types, including a range of B-lymphoid cancers. AID misexpression promotes widespread DNA damage, genomic instability, tumor progression, and therapy resistance. Inhibition of the homologous recombination factor RAD51 with 4,4'-diisothiocyanatostilbene-2,2'-disulfonic acid (DIDS), reduces repair of AID-induced genomic damage and can induce B-cell death. It is demonstrated herein that C-1523, a potent DIDS analog, disrupts the normal nucleocytoplasmic distribution of RAD51 and suppresses sister chromatid exchange. Attenuation of recombinational repair by C-1523 inhibits repair of AID-initiated DNA breaks, leading to cell-lethal DNA damage overload in malignant B-lymphocytes. Unexpectedly, the combined action of C-1523 and AID causes cell death by p53-dependent mitotic catastrophe, without canonical apoptosis. Accordingly, described herein is a synthetic lethal therapy, wherein the combined effect of RAD51 attenuation and AID expression can induce tumor cell selective self-destruction. This approach is a tumor-cell selective therapeutic paradigm for AID-expressing cancers.

Introduction

Treatment-induced side effects represent a significant challenge in clinical oncology. Conventional chemotherapies are often associated with a range of off-target toxicities that can limit dosing and treatment duration, undermine patient compliance, and cause adverse long-term effects including secondary tumorigenesis (Cheson et al., 1999; Molica, 2005; Robak and Robak, 2007). Molecularly targeted or tumor selective therapeutics promise effective treatment while mitigating side effects and off-target toxicities. Advances in molecular genetics and genome sequencing technologies have led to an exponential increase in the development of molecularly targeted small molecule drugs (e.g. imatinib) as well as target-specific biologics (e.g. rituximab) in the last two decades. Described herein is the development of a new approach to targeting tumor cells, leveraging DNA damaging genetic programs inherent in malignant cells to induce tumor cell self-destruction.

Activation induced cytidine deaminase (AICDA or AID) is a DNA mutase/recombinase normally expressed exclusively in antigen stimulated germinal center B-lymphocytes (Chaudhuri et al., 2003; McBride et al., 2006; Muramatsu et al., 2000). AID deaminates deoxycytidines at target sites in immunoglobulin loci, creating U::G base pair mismatches (Chaudhuri et al., 2003). These mismatched bases may be corrected to restore the original C::G base pairs; may be misrepaired causing C>T transitions; or may ultimately be cleaved to produce DNA single strand or double strand breaks (SSB and DSB, respectively) (Zan and Casali, 2008). AID-initiated point mutations drive normal B-cell somatic hypermutation, while AID-initiated DSBs induce immunglobulin class switch recombination (Chaudhuri et al., 2003; McBride et al., 2006; Muramatsu et al., 2000). Although the immunogloublin genes are its known physiologic targets, AID can also generate point mutations and DSBs at numerous non-Ig locations throughout the genome (Hasham et al., 2010; McBride et al., 2006; Robbiani et al., 2009; Staszewski et al., 2011). Normally, these "off target" point mutations and DSBs are efficiently repaired by mismatch repair (MMR) and homologous recombination (HR) repair, respectively (Chahwan et al., 2012; Hasham et al., 2012; Hasham et al., 2010).

While AID expression is normally restricted to germinal center B-cells, numerous studies have shown AID to be overexpressed in a variety of tumors, of both lymphoid and non-lymphoid origin (Heintel et al., 2004; Klemm et al., 2009; Kou et al., 2007; Palacios et al., 2010; Pasqualucci et al., 2008; Shinmura et al., 2011). AID is constitutively expressed in greater than 40% of human primary chronic lymphocytic leukemia (CLL) cases (Lamont et al., 2013). In lymphoid blast crisis CML, AID expression leads to genomic instability, hypermutation of DNA repair genes, and acquisition of Imatinib resistance due to BCR-ABL point mutations (Klemm et al., 2009; Liu et al., 2011). In primary CLL, AID overexpression is associated with earlier age at diagnosis and an increased likelihood of requiring treatment (Palacios et al., 2010). Although the precise functional consequences of AID overexpression in malignant cells is not understood in most cases, AID mutational activity appears to be co-opted by transformed cells, leading to increased mutation rates and genomic instability (Klemm et al., 2009; Kou et al., 2007; Okazaki et al., 2003; Palacios et al., 2010; Shimizu et al., 2012).

The homologous recombination (HR) pathway of DSB repair is critical for the survival of AID expressing B-lymphocytes (Caddle et al., 2008; Hasham et al., 2012; Hasham et al., 2010). HR is generally considered a high fidelity DSB repair mechanism, promoting the repair of DNA breaks from an undamaged sister chromatid template and mediating DNA replication fork restart following fork collapse, stalling, or regression. The RAD51 protein is a core HR factor, required to initiate the HR reaction through nucleoprotein filament formation, homology searching, and DNA strand exchange (Daboussi et al., 2002; Shinohara et al., 1992; Sung and Robberson, 1995). RAD51 participates in multiple protein subcomplexes together with subsets of RAD51 proteins, and a variety of other co-factors. There are five (5) known RAD51 paralogues: RAD51B, RAD51C, RAD51D, XRCC2, and XRCC3 (Kawabata et al., 2005; Suwaki et al., 2011; Thacker, 2005). Partial attenuation of HR by shRNA knockdown of XRCC2 was sufficient to sensitize both primary and transformed B-lymphocytes to AID-mediated DNA damage overload (Hasham et al., 2010). Similar results are obtained with the small molecule RAD51 inhibitor 4,4'-diisothiosyanatostilbene-2,2'-disulfonic acid (DIDS) (Lamont et al., 2013).

Described herein is the development of a potent and highly selective analog of DIDS, (E)-5-acetamido-2-(4-(3-isopropylthioureido)-2 sulfonatostyryl)benzenesulfonate (C-1523). C-1523 inhibits HR by altering the nucleocytoplasmic distribution of RAD51 following DNA damage induction. C-1523 exposure reduces the repair of AID-induced DNA double strand breaks, leading to AID-dependent cytotoxicity in both normal and malignant B-lymphocytes. Unexpectedly, it is demonstrated herein that cell death induced by the combination of C-1523 and AID activity is p53-dependent mitotic catastrophe, and not canonical apoptosis. These results indicate that synergistic cytotoxicity, induced by DNA repair inhibition in cells with high levels of genetically programmed DNA damage—such as the collateral genomic damage caused by AID activity—is a new approach to tumor-cell selective therapy.

Results

C-1523, a potent new inhibitor of RAD51-mediated HR. Exposure to the RAD51 inhibitor, DIDS, induces cell death in primary B-lymphocytes by reducing HR repair of AID-initiated DSBs, leading to DSB accumulation and DNA damage overload (Ishida et al., 2009; Lamont et al., 2013). This indicates that RAD51 is a viable therapeutic target, at least in AID-overexpressing tumors. To more directly test whether pharmacologic inhibition of RAD51 could represent a possible therapeutic approach, C-1523, a more potent analog of DIDS, was developed. A library of 105 DIDS derivatives was generated, focusing on (1) functional group substitutions of the 2- and 2'-sulfonates and 4- and 4'-isothiocyanate groups; (2) reduction of the central double bond linking the benzene rings; and (3) altering the symmetry of the molecule, while preserving the core double benzene ring structure (FIG. 12A).

Figures 12A, 12B, 12C, 12D:
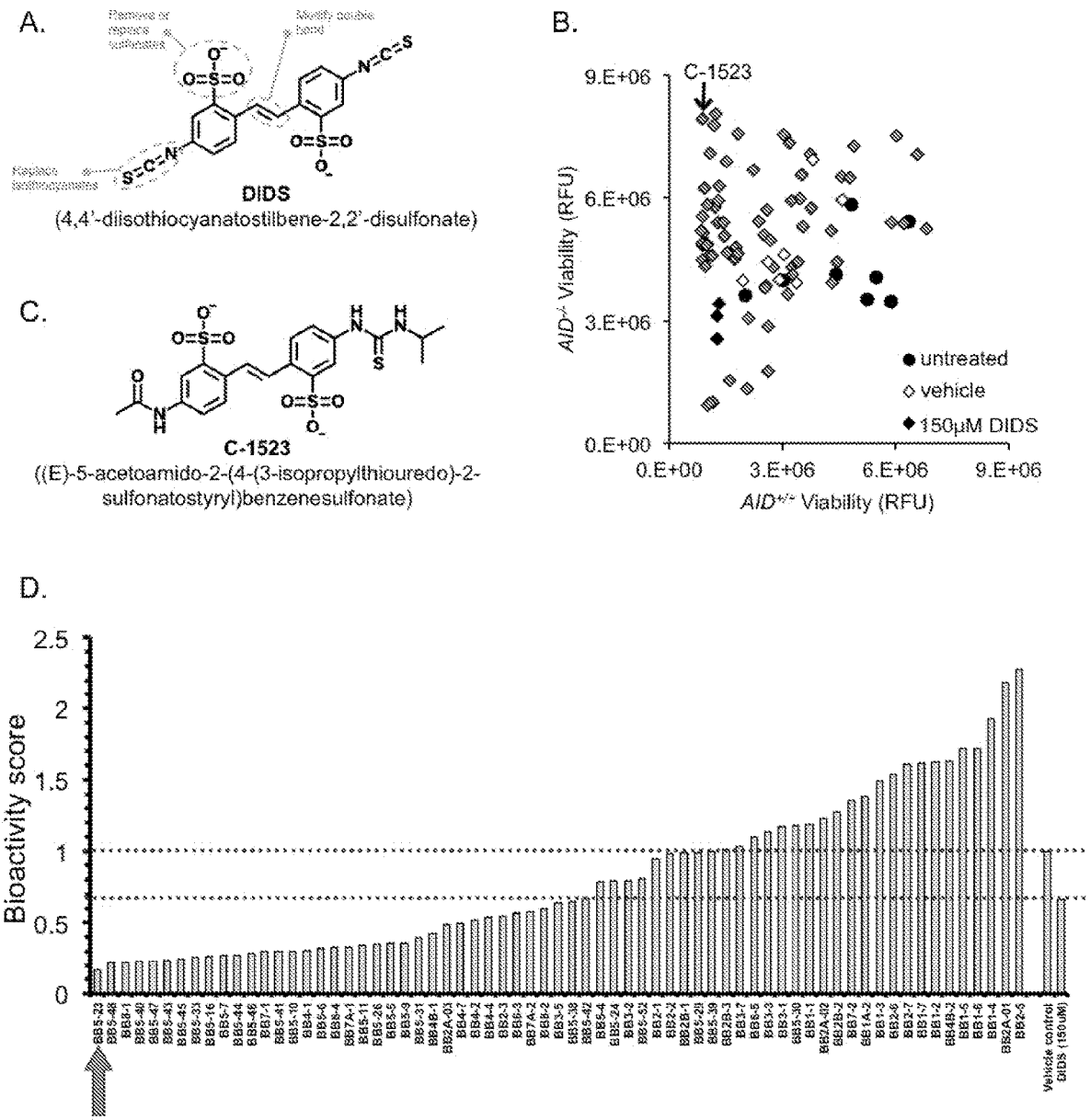
FIGS. 12A-12D demonstrate DIDS library screening for potent inhibitors homologous recombination identifies C-1523 as a second-generation candidate.

Using a 96-well colorimetric viability assay (MultiTox-Fluor Multiplex Cytoxicity assay) 67/105 DIDS analogs were tested for effects on proliferation and viability in AID-expressing versus AID-knockout mouse B-lymphocytes (FIG. 12B). All compounds were tested at 10 μM, and those that were selectively cytotoxic to AID-expressing, but not AID-deficient, B-cells were scored as hits (FIGS. 12B, 12D). Compounds that retained the linking double bond and the sulfonates, but contained asymmetric substituents at the 4- and 4' positions were strongly cytotoxic to AID-expressing B-cells, while showing minimal effects in AID-/- B-cells under identical conditions (FIG. 12B, 12D). By contrast, compounds in which the sulfonates were replaced with a proton and/or were symmetrically substituted the groups at the 4 and 4' positions, produced the opposite effect, either inducing death preferentially in AID-/- cells, or promoting the proliferation of AID+/+ cells.

A bioactivity assay, measuring the ratio of viability following compound treatment in AID-positive cells versus AID-negative cells, was established. All screened compounds were then ranked according to their AID+:AID- activity score. By this analysis the compound (E)-5-acetoamido-2-(4-(3-isopropylthiouredo)-2-sulfonatostyryl) benzenesulfonate (C-1523, FIG. 12C) showed a roughly 6-fold greater effect in AID+ cells than in corresponding AID-cells, indicating strong selectivity for AID-expressing cells (FIGS. 12B, 12D). Dose response data showed C-1523 to be at least 1500 times more potent than DIDS, eliciting AID-specific cytotoxicity at 100 nM (versus 150 μM for DIDS) (FIG. 12B). C-1523 was the most potent DIDS analog tested, and based upon these results, was pursued for further evaluation and mechanistic testing.

Figures 13A, 13B, 13C, 13D, 13E, 13F:
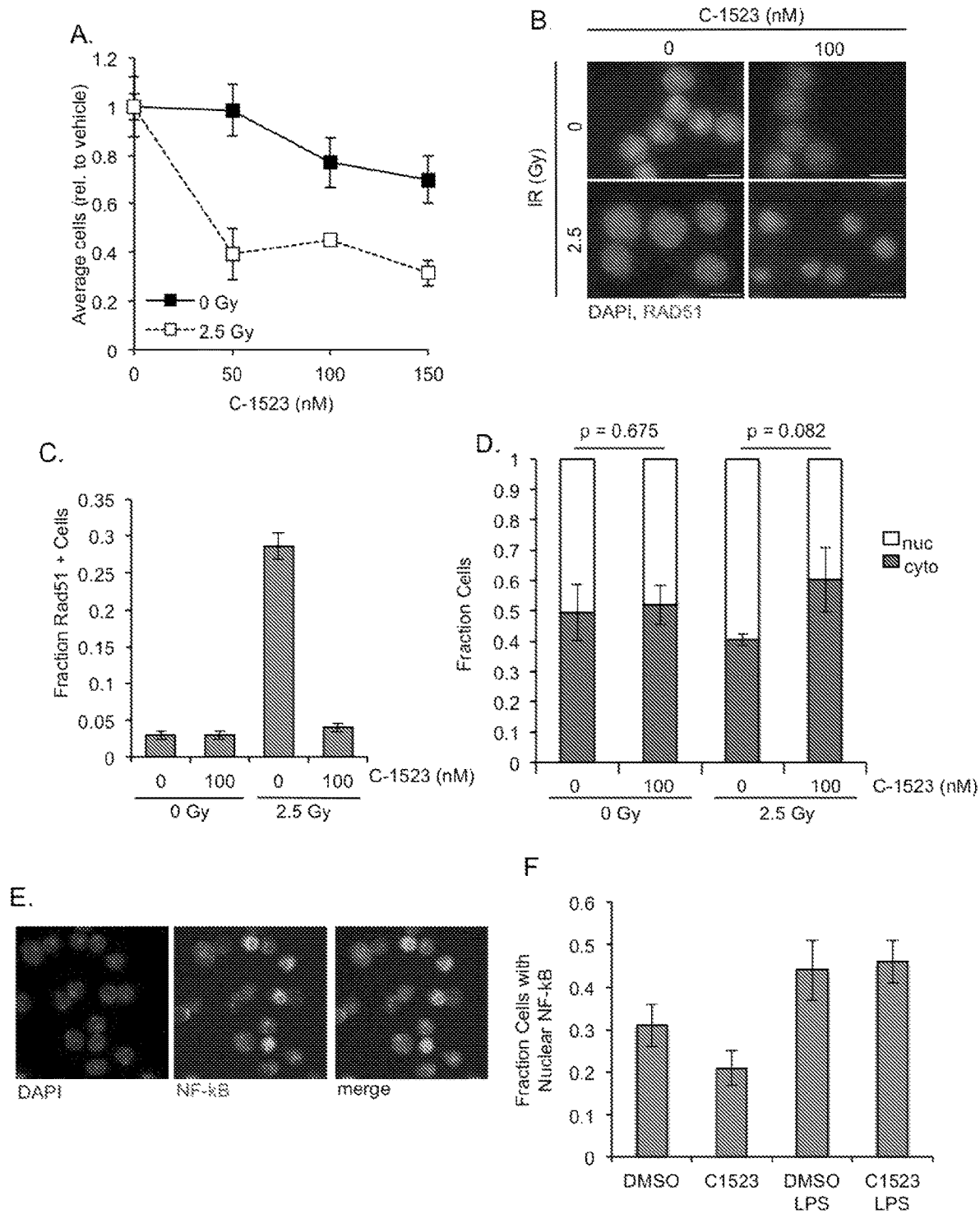
FIGS. 13A-13B demonstrate that C-1523 sensitizes cells to IR and inhibits RAD51 foci formation.
FIG. 13C depicts the quantification of cells with nuclear RAD51 (RAD51+) from FIG. 13B. Error bars represent the SEM for three independent experiments.
FIG. 13D depicts the quantitation of RAD51 expression in nuclear and cytoplasmic fractions as determined by Western Blot. Values represent the average of three independent experiments and error bars are the SEM.
FIG. 13E depicts the immunofluorescent detection of NF-κB localization in primary murine B cells. NF-κB staining is in green, nuclear DNA is in blue (top panels).
FIG. 13F depicts the quantitation of nuclear NF-κB staining from FIG. 13E. Error bars represent the SEM of three independent experiments.

C-1523 disrupts RAD51 nucleocytoplasmic distribution and damage induced relocalization. To assess the DNA repair inhibitory activity of C-1523, radiosensitivity was measured in the mouse leukemia cell line, CH12-F3, with or without C-1523. Cells were cultured in the presence of vehicle, 50 nM, 100 nM, or 150 nM C-1523, and given either 0 or 2.5Gy of ionizing irradiation. Cells were allowed to recover in culture in the presence of C-1523 (or vehicle control) and viable cells were quantified. C-1523 treatment resulted in sensitivity to ionizing irradiation at every concentration tested, supporting a DNA repair inhibitory activity for C-1523 (FIG. 13A).

It was next tested whether C-1523 would affect RAD51 localization or DNA damage-induced focus formation. Primary mouse B-cells were treated with 100 nM C-1523 (or vehicle control) and given either 0 or 2.5Gy ionizing irradiation. Following recovery in cell culture, cells were fixed and stained for immunofluorescence imaging to measure subcellular localization of RAD51. This analysis showed that C-1523 treatment completely blocked IR-induced RAD51 relocalization and focus formation (FIGS. 13B, 13C). Treated cells exhibited >6-fold reduction in IR-induced RAD51 focus formation, showing levels indistinguishable from background in untreated, unirradiated cells (FIG. 13C). To confirm the effect of C-1523 on RAD51 subcellular localization, nucleocytoplasmic distribution was independently measured following C-1523 treatment by cell fractionation and Western blotting (FIG. 13D; Supplemental FIG. 2). C-1523 treatment resulted in a small, but measurable reduction in the fraction of RAD51 localized to the nucleus, following irradiation. This effect on subcellular localization was specific to RAD51, as localization of NF-kB, which undergoes nuclear translocation and homing to genomic target sites after cell stimulation, was unaffected by C-1523 exposure (FIGS. 13E-13F).

Figures 14A, 14B, 14C, 14D, 14E:
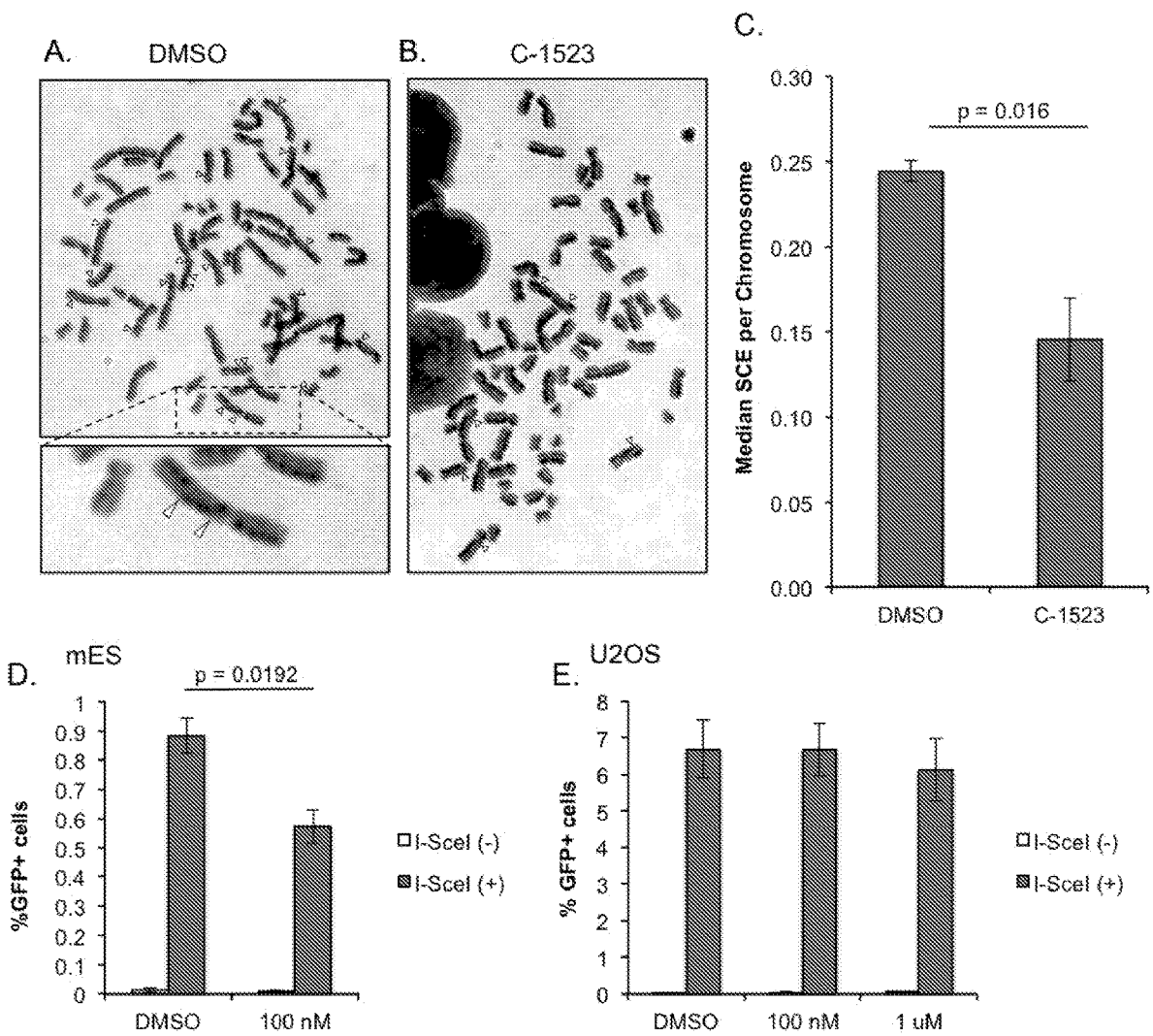
FIGS. 14A-14E demonstrate that C-1523 inhibits sister chromatid exchange.

C-1523 inhibits Sister Chromatid Exchange. The data indicated that C-1523 inhibits HR mediated DSB repair by reducing RAD51 relocalization. To directly measure the effect of C-1523 on RAD51-mediated homologous recombination, we measured sister chromatid exchange and HR repair of an endonuclease generated DSB. Sister chromatid exchange (SCE) is a RAD51-mediated homologous recombination event between replicated sister chromatids in replicative or post-replicative cells, and reflects repair of replication-associated DNA damage. SCE can be measured following differential chromatid labeling by BrdU incorporation (Latt and Schreck, 1980). SCE is known to occur at a high rate in HEK293T cells, with approximately 0.25 spontaneously occurring exchange events per chromosome (FIGS. 14A, 14C) (Londono-Vallejo et al., 2004). Following treatment with 100 nM C-1523, the median number of SCE events per chromosome was significantly reduced relative to cells treated with DMSO vehicle alone (FIGS. 14B, 14C).

To assess the ability of C-1523 to inhibit RAD51-mediated repair of non-replication DNA breaks, HR repair of an endonuclease generated DSB was measured, in both mouse and human cells, using DR-GFP reporter assays (Moynahan et al., 2001; Nakanishi et al., 2005). The percentage of GFP-positive cells was reduced by about 40% in mES cells treated with 100 nM C-1523 compared to DMSO-treated cells (FIG. 14D). However, no significant change in GFP-positive cells was observed in human U2OS cells treated with C-1523, at either 100 nM or 1 μM C-1523 (FIG. 14E). These results indicate that C-1523 partially attenuates, but does not completely abrogate, HR-mediated repair of direct DSBs induced by endonucleases.

Figures 15A, 15B, 15C, 15D, 15E, 15F:
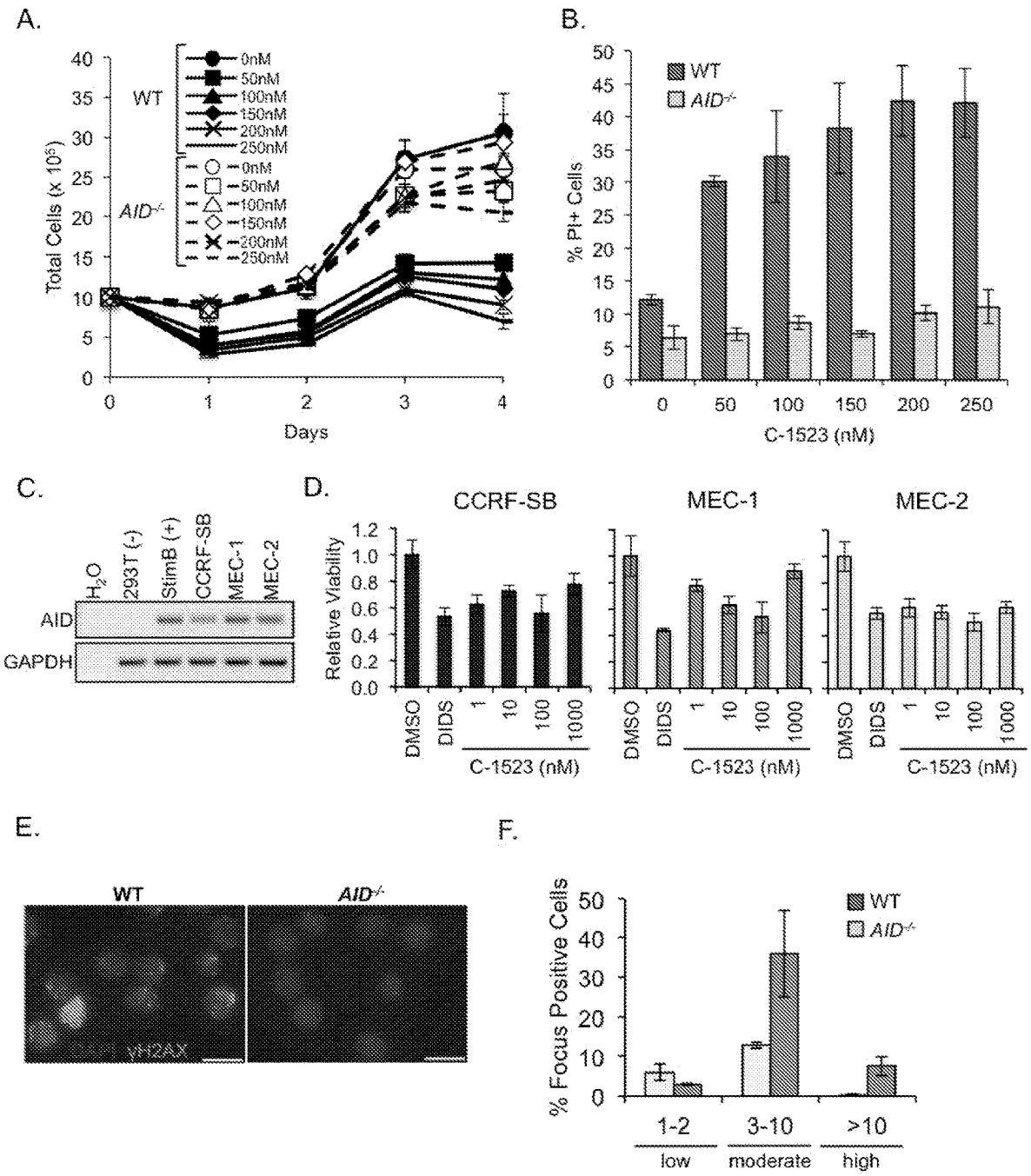
FIGS. 15A-15F demonstrate that the viability of primary mouse cells and human leukemic cell lines is reduced following treatment with C-1523.

C-1523 induces AID-dependent cytotoxicity. Based on results with DIDS, it was predicted that HR inhibition by C-1523 would lead to AID-mediated cytotoxicity (Lamont et al., 2013). To test this, primary splenic B-cells were obtained from WT or AID-/- mice, and cultured for four days, with or without αCD40+IL-4 activation, in the presence of vehicle or C-1523 at concentrations ranging from 50-250 nM. At all concentrations tested, C-1523 selectively suppressed cellular expansion in AID-expressing WT cultures (FIG. 15A). By contrast, αCD40+IL-4 activated AID-/- B-cells, with or without C-1523 exposure, expanded identically to vehicle-treated controls. To determine whether the cell culture growth suppression elicited by the combination of AID and C-1523 was associated with cytostasis or cytotoxicity, cell viability was measured by flow-cytometric analysis of cultures stained with propidium iodide (PI). C-1523 led to a significant increase in PI+ cells, indicative of cell death, in the AID-expressing WT cell cultures, but not in the corresponding AID-/- cultures (FIG. 15B). These findings were independently confirmed by manual cell counting after staining with vital dye (data not shown). Collectively, these data demonstrate that inhibition of RAD51-mediated HR significantly sensitizes B-cell to AID-induced cytotoxicity.

The effect of C-1523 on the viability of AID-expressing human B cell tumor cell lines was further tested (FIG. 15C). CCRF-SB is an acute lymphoblastic leukemia cell line derived from a buffy coat preparation (Foley et al., 1968). MEC-1 and MEC-2 are cell lines derived from a patient with chronic lymphocytic leukemia at two different timepoints (before and after fludarabine and rituximab therapy) (Stacchini et al., 1999). C-1523 was tested in these cell lines over a dose range from 1 to 1000 nM, in log increments, and compared to 150 μM DIDS. CCRF-SB and MEC-1 cells demonstrated a dose-dependent viability response to C-1523 over the range tested, while MEC-2 cells were sensitive at all doses tested (FIG. 15D). CCRF-SB and MEC-1 cells had the greatest viability reduction at 100 nM C-1523, which was similar to the viability reduction observed in cells treated with DIDS. Interestingly, at the highest dose of C-1523 tested, 1000 nM, the viability reduction in CCRF-SB and MEC-1 cells was less than that observed after treatment with 100 nM (FIG. 15D). This biphasic response was also observed in primary mouse B cells over this same dose range (Supplemental FIG. 3). Biphasic or hormetic responses for small molecules can reflect a number of biochemical/biological mechanisms (Calabrese, 2013).

To determine whether the cytotoxic effect of C-1523 in AID-expressing cells was associated with DNA damage overload, the accumulation of unrepaired AID-initiated DSBs was measured by H2AX immunoostaining, in activated mouse B-lymphocytes (FIGS. 15E, 15F). Primary WT or AID-/- mouse splenic B cells were isolated, cultured with vehicle or 100 nM C-1523, and activated with αCD40 and IL-4. C-1523 treatment lead to accumulation of H2AX foci in AID-expressing WT cells, but not in corresponding AID-/- cells (FIGS. 15E, 15F). Under normal, untreated conditions, AID activity leads to a low number of H2AX foci (1-2) per cell, but supernumerary H2AX foci (>2) are rare (Hasham et al., 2010; Lamont et al., 2013). Following treatment with 100 nM C-1523 a significant increase in the fraction of cells with supernumerary foci (3-10 per cell) was observed only in activated, AID-expressing B-cells (FIG. 15F). Collectively, these data demonstrate that C-1523 is a potent suppressor of RAD51 mediated DSB repair, inhibiting the resolution of both IR-induced and physiologically relevant AID-initiated DSBs.

Figures 16A, 16B, 16C:
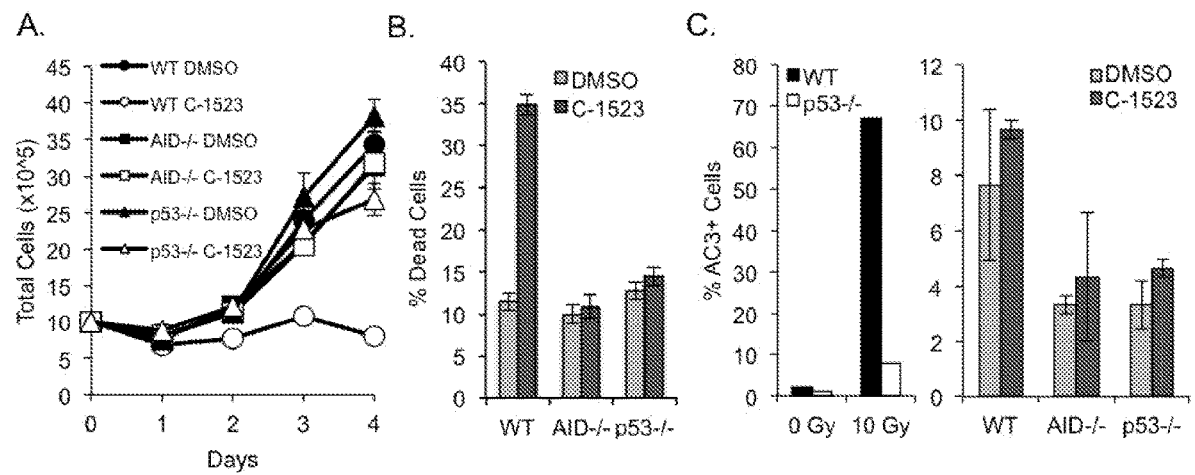
FIGS. 16A-16C demonstrate that cell viability reduction induced by C-1523 in AID-expressing B cells is p53-dependent.
Figure 17A:
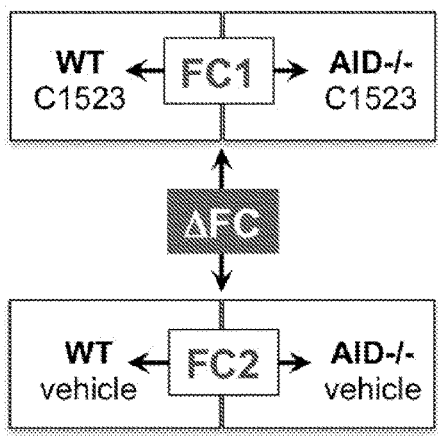
FIGS. 17A-17D demonstrate that gene expression analysis in C-1523-treated cells did not implicate programmed cell death pathways in decreased viability.
Figure 17B:
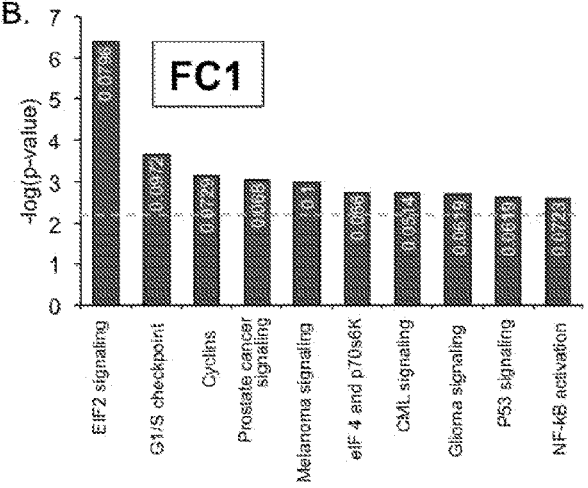
Figure 17C:
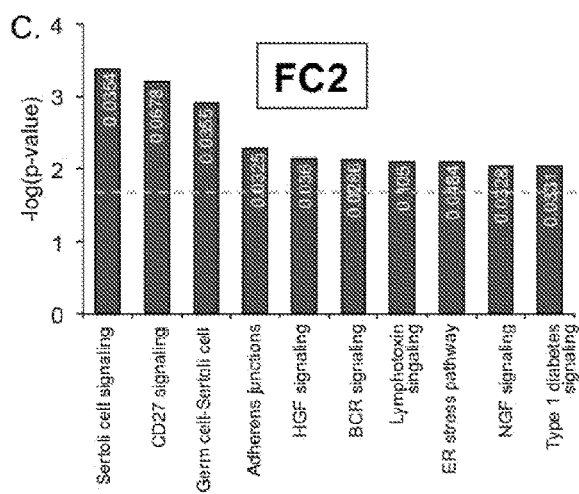
Figure 17D:
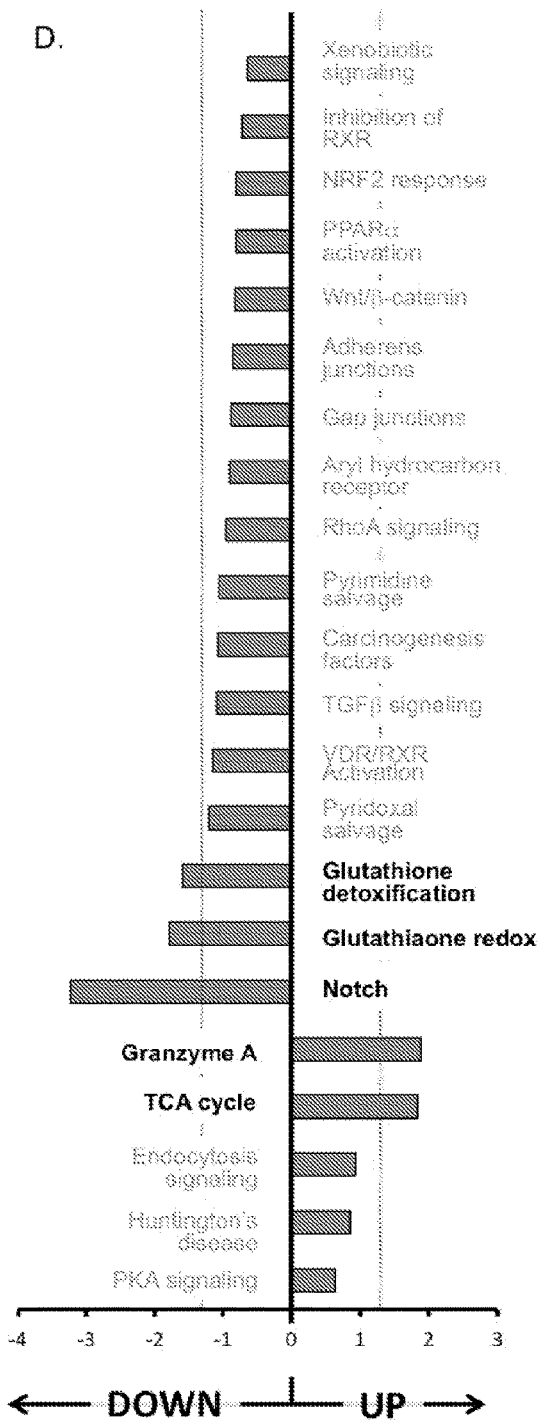

Cell death mediated by C-1523 is p53-dependent. It was hypothesized that AID-dependent cytotoxicity induced by C-1523 would be associated with p53-mediated apoptosis. To test the importance of p53, a central regulator of cellular responses to DNA damage, viability was measured in mouse primary B-cells from Trp53+/+ versus Trp53-/- mice following exposure to C-1523. As predicted, cell death induced by C-1523 was both AID and Trp53 dependent. B-cell cultures from Trp53-/- mice did not show reduced viability or increased cell following treatment with 100 nM C-1523 over the course of the 4-day activation (FIGS. 16A, 16B). Caspase 3 activation, a marker of apoptotic cell death, was measured in C-1523 treated B-cells. B-cells were stained with an antibody that recognizes cleaved, activated caspase-3 (AC3) and the number of AC3-positive cells was measured via immunofluorescence microscopy. Following 10 Gy of ionizing irradiation Trp53+/+(WT), but not Trp53-/- cultures show a >30-fold increase in the percentage of AC3+ cells, confirming Trp53 dependent apoptosis in these cells after DNA damage. By contrast, C-1523 treatment did not significantly induce caspase 3 activation in WT, AID-/-, or Trp53-/- B-cells (FIG. 16C). In order to more completely rule out apoptosis as the mode of cell death following C-1523 treatment in B cells, the expression of other common markers of apoptotic induction was examined via Western Blot. At 2 days following activation with αCD40 and IL-4 and treatment with vehicle or C-1523, no cleavage of PARP-1 or caspase-9 was observed (data not shown). By 3 days, low levels of cleaved PARP-1 and caspase-9 were apparent, however they were present in all genotypes and all treatments, demonstrating that this is due to a background level of apoptotic induction and not due to C-1523 treatment specifically (data not shown). These data, combined with the caspase-3 data in FIG. 17C demonstrate that cell death in response to C-1523 treatment in AID-expressing cells does not occur through apoptotic mechanisms. These unexpected results indicated that AID-induced cytotoxicity in C-1523-treated B-cells was not strongly associated with canonical p53-dependent apoptosis.

C-1523 induces non-apoptotic cell death via non-apoptotic mitotic catastrophe. The surprising lack of apoptotic cell death induced by C-1523 prompted us to evaluate gene expression signatures to identify other potential cell death pathways. To measure gene expression profiles, an RNASeq analysis of primary, activated WT versus AID-/- cells that were cytokine-treated with 100 nM C-1523 or vehicle was conducted (FIGS. 17A-17D). Ingenuity Pathways Analysis (IPA), of most significantly altered pathways did not identify any previously annotated cell death pathways. Four of the five most differentially expressed pathways C-1523-treated versus vehicle-treated cells involved cellular metabolism (glutathione redox, TCA cycle) and Notch signaling (FIGS. 17B-17E), pathways that have collectively been linked to cell death by mitotic catastrophe (Curry et al., 2007; Hung et al., 2013).

Figures 18A, 18B, 18C:
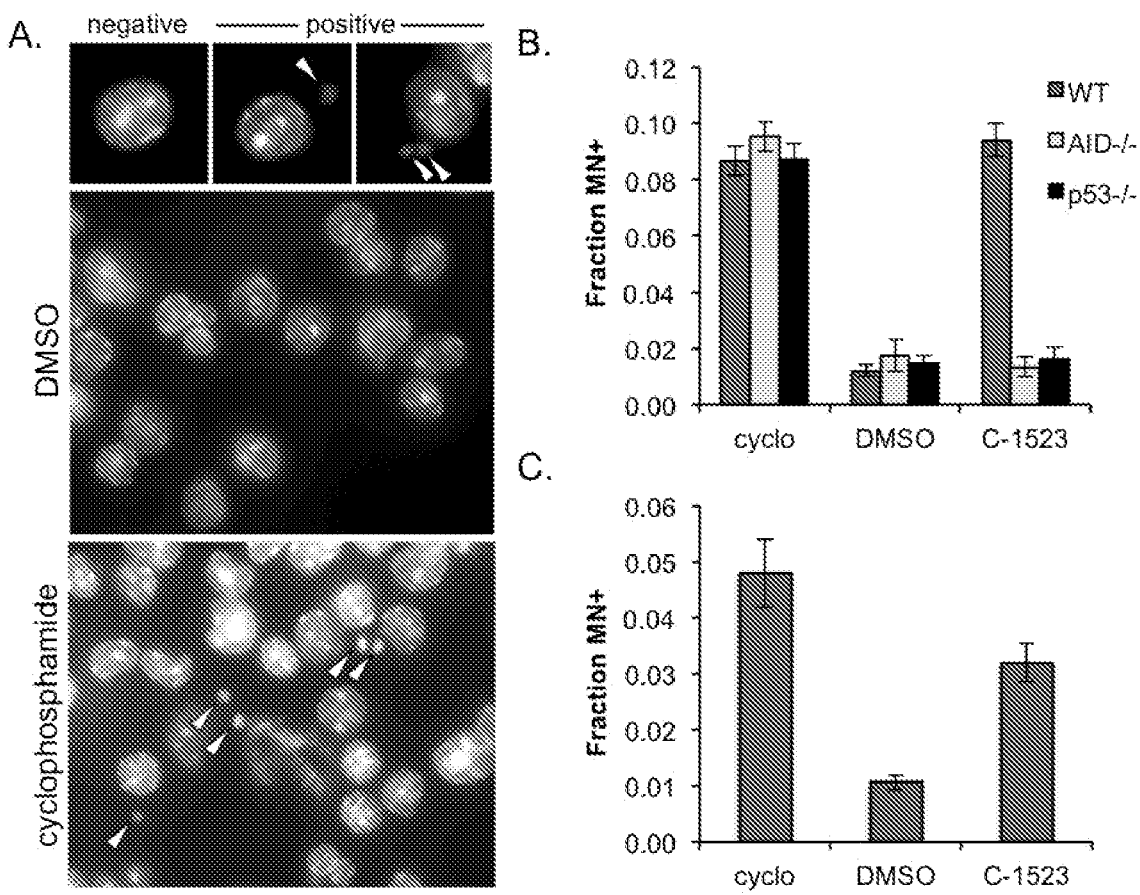
FIGS. 18A-18C demonstrate that AID induces mitotic catastrophe in C-1523 treated cells.

This observation, together with the absence of apoptotic pathways in led to the investigation of mitotic catastrophe, a cell death mechanism that has been increasingly recognized as apoptosis-independent alternate cell death pathway associated with DNA damage overload (Roninson et al., 2001a; Roninson et al., 2001b). Aberrant, ineffective, or failed mitoses often give rise to micronuclei, small remnants nuclear material that become separated from the bulk of the nucleus due to failed chromosome retraction by the centromeres or by failed cytokinesis (Roninson et al., 2001a). (Curry et al., 2007; Hung et al., 2013). Primary mouse B cells of all genotypes tested (WT, AID-/-, and p53-/-) that were treated with cyclophosphamide (a nitrogen mustard DNA alkylating agent) exhibited approximately 9% micronuclei after 3 d (FIGS. 18A, 18B). In WT cells that were treated with 100 nM C-1523, a 9-fold increase in micronuclei was observed compared to DMSO, while no increase in the fraction of micronuclei was observed in AID-/- or p53-/- cells (FIG. 7B). Induction of micronuclei was also observed in MEC-1 cells following treatment with 100 nM C-1523 for 3 days (FIG. 7C), with approximately 3.5-fold more micronuclei in treated cells than those that received vehicle. This lower level of micronuclei in MEC-1 cells compared to the primary mouse cells might reflect a difference between species, or between a primary cell and an immortalized cell line, as even after cyclophosphamide treatment, MEC-1 cells had approximately half as much micronuclei as primary cells.

Discussion

It is demonstrated herein that inhibition of homologous recombination (HR) is an effective means of sensitizing AID-expressing cells to DNA damage overload. Further, it is demonstrated that AID-induced DNA damage leads to p53-dependent cell death in AID-activated B-lymphocytes. Surprisingly, AID-induced B-cell cytotoxicity is non-apoptotic, and occurs via mitotic catastrophe, likely due to replication stress associated with attenuated recombinational repair of DNA damage.

RAD51-dependent homologous recombination is an essential pathway, required for proliferation, DNA double strand break repair and cellular viability most mammalian cells. In proliferative tissues, RAD51 recombinational activity is required to restart stalled or collapsed DNA replication forks. In addition to its replication-associated roles, RAD51-dependent recombination is important for homology mediated, high-fidelity repair of DNA double strand breaks (DSBs) in replicative or post-replicative cells. Cells with physiologically normal levels of genotoxic damage harbor RAD51 protein distributed between the nucleus and cytoplasm, while cells with high levels of DNA damage or replication stress relocalize cytoplasmic RAD51 to the nucleus where it concentrates at sites of action. In this context, targeting RAD51 relocalization—suppressing its auxiliary but not its baseline activity—is an attractive approach to tumor cell selective therapy in cancers associated with excessive genotoxic stress. It is demonstrated herein that C-1523 disrupts the normal RAD51 nucleocytoplasmic distribution, inhibits DNA damage induced relocalization, and significantly sensitizes cells to AID activity. Attenuating RAD51-mediated HR by C-1523 leads to DNA damage overload specifically and selectively in AID-expressing cells, including activated B-lymphocytes and malignant B-cells that overexpress AID. Accordingly, described herein is a therapeutic approach that can selectively sensitize AID-expressing tumor cells while sparing most normal tissues. Interestingly, C-1523 induced cytotoxicity in AID-expressing cells is due to mitotic catastrophe, rather than apoptosis, indicating that this therapeutic approach can be applicable in some cancers with reduced apoptotic functions.

DNA damage overload, induced by DNA damaging therapeutic agents has been a central, and generalizable, tenet in cancer therapy for decades (Harper and Elledge, 2007). Conventional antineoplastic therapies—nucleoside analogs, anti-replicative agents, and cytotoxic drugs—can be highly effective at tumor cell destruction but are poorly selective for malignant cells. Consequently, antineoplastics are associated with a range of dose limiting toxicities and can lead to significant long-term side effects, including induced secondary tumors, which negatively impact quality of life even for patients in long-term remission. An important goal, therefore, in oncology drug development has been the identification of treatment strategies that are selective for tumors, reducing deleterious side effects. Synthetic lethality therapies based upon inhibition of poly ADP-ribose polymerase (PARP) in BRCA1 or BRCA2 2 mutated cancers exemplify a selective therapeutic approach that exploit genetic vulnerabilities inherent in transformed cells (Boss et al., 2010). Mutations in BRCA1 or BRCA2 decrease the efficiency of DNA DSB repair, leading to an acute reliance on SSB break repair for cellular survival. Treatment with a PARP inhibitor, such as olaparib, inhibits repair of single-strand breaks (SSB), resulting in reduced proliferative capacity and cytotoxicity specifically in cells with diminished DSB repair function. Non-transformed tissues lacking BRCA1 or BRCA2 mutations are significantly more resistant PARP inhibition owing to intact DSB repair. Synthetic lethality can be considered a "two pronged" mechanism based on the abrogation of separate arms of DNA damage repair pathways, leading to DNA damage overload and culminating in tumor selective cell death.

The results described herein relate to an analogous approach, which is termed synergistic toxicity, by which inhibition of a single DNA damage repair pathway—in this case HR—is coupled with a genetically programmed excess of DNA damage. This approach leads to an intolerable imbalance in DNA damage and repair, producing DNA damage overload and likewise initiating tumor selective cell death. Whereas synthetic lethality based on PARP inhibition simultaneously reduces two arms of DNA damage repair causing susceptibility to spontaneously occurring DNA damage, synthetic lethality relies on single pathway inhibition and exploits the elevated DNA damaging activity present in some tumor types. Like synthetic lethality, synergistic toxicity has the potential to minimize off-target side-effects due to the restriction of genetically programmed DNA damage to malignant cells.

Tumor evolution represents a significant challenge in modern clinical oncology, leading to tumor progression and the acquisition of therapy resistance. Tumor evolution is defined as the adaptive outgrowth of new tumor cell clones, with unique genetic changes, following exposure to various selective pressures, including radio- or chemotherapy. Genomic instability accelerates tumor evolution, by increasing the rate of mutations and thus the appearance of new tumor cell variants with key selective advantages. Interventions that eradicate cells with genomic instability could potentially mitigate tumor evolution. Targeting the mechanisms that underlie tumor evolution can be done either as a monotherapy or in combination with other treatments, which can enhance the efficacy or durability of conventional treatments. HR inhibition coupled with AID-induced genomic damage can be considered as a treatment that targets tumor evolution, as AID has been shown to generate permissive genomic modifications that allow for mutation and drive tumor progression (Nagaoka et al., 2010; Okazaki et al., 2003).

In summary, it is demonstrated herein that HR inhibition is an effective means of sensitizing AID-expressing cells to DNA damage overload. The cell death induced is dependent upon p53, but progresses through a non-apoptotic, mitotic catastrophe mechanism. Targeted therapies with durable, long-term anti-neoplastic effects without deleterious side effects are the current mandate for the oncology community, and the synergistic toxicity strategy described herein exemplifies that goal.

Materials and Methods

Viability screening of chemical library of DIDS modifications. MultiTox-Fluor Multiplex Cytotoxicity assay was performed according to manufacturer specifications (Promega, Madison, Wis.).

Mice. Aicda–/– (AID–/–) and C57BL6/J (WT; AID+/+) mice were maintained in pressurized, individually ventilated caging and fed standard laboratory diet; colony maintenance was performed as described elsewhere (Muramatsu et al., 2000). The AID–/– strain was derived as reported by Muramatsu et al. (Muramatsu et al., 2000) and backcrossed to C57BL6/J for >20 generations.

Cell lines and cell culture. CH12-F3 were procured and cultured as described elsewhere (Lamont et al., 2013). CCRF SB (ATCC® CCL-120TM) and HEK293T cells were purchased from the American Type Culture Collection. MEC-1 and MEC-2 cells were purchased from the Leibniz Institute DSMZ-German Collection of Microorganisms and Cell Cultures (DSMZ, Germany). All cell lines were cultured according to manufacturer recommendations. Isolation, culturing, and induction of class-switching in primary mouse splenic B-cells was carried out as previously described (Hasham et al., 2010; Lamont et al., 2013). Cell viability was determined through 0.2% Trypan blue (Lonza) staining and counting of dye-excluding (live) and dye-absorbing (dead) cells via hemocytometer (Neubauer). Immunofluorescence. Cells were allowed to attach to poly-L-lysine-coated coverslips and then fixed with 3% NBF, 2% sucrose PBS solution, and permeabilized in 0.1% Triton X-100. Primary antibodies: $^3$H H2AX (1:400, Bethyl Laboratories, Inc.), active caspase-3 (1:100, Abcam), Rad51 (1:100, Abcam), and NF-$\kappa$ (1:400, Cell Signaling, #D14E12). Secondary antibodies were goat anti-rabbit IgG-TRITC (1:1000, Jackson ImmunoResearch Laboratories, Inc.) or goat anti-rabbit IgG-AlexaFluor 488 (1:500, Life Technologies). Coverslips were mounted on slides using VectaShield plus DAPI (Vector Laboratories, Inc.), and imaged as previously described (Caddle et al., 2008).

Propidium Iodide and flow cytometry. PI staining was performed as described elsewhere (Caddle et al., 2008; Hasham et al., 2012). All flow cytometry data was collected on a FACSCalibur™ using CellQuest Pro™ acquisition software (BD Biosciences) and analyzed via FlowJo™ (v.9.5.2, Treestar, Inc.) Metaphase Preparations and sister chromatid exchange assay. HEK293T cells were cultured with DMSO or 100 nM C-1523 for three days. At 44 h prior to harvest, cells were given 10 µM BrdU (BD Biosciences) in culture so that incorporation could take place over two cell cycles to differentially label only one chromatid. Karyo-Max™, a colcemid solution (Invitrogen), was added to cultures at a dilution of 1:200 for 30 min to 1 hr prior to fixation to promote metaphase arrest of dividing cells. Cells were then rapidly transferred to warm (37° C.) hypotonic KCl solution (75 mM) and incubated for 20 minutes at 37° C. to swell cells. Rapid fixation was accomplished by two changes of cold 3:1 methanol:acetic acid. Metaphases were dropped onto slides, exposed to UV, and stained with Giemsa following protocol (Stults et al., 2014). Metaphases were visualized by bright-field microscopy, and 20 metaphases were scored per sample.

DR-GFP assay. Performed as described previously (Lamont et al., 2013). Micronuclei assay. Primary murine splenic B cells were isolated and set up in culture as for a viability assay, activated with αCD40 and IL-4 and treated with 100 nM C-1523 or DMSO vehicle for 3 days. As a positive control for micronucleus formation, some cells were treated with 5 µg/mL cyclophosphamide (Sigma) for 3 days (Krishna et al., 1995). MEC-1 cells were cultured with 100 nM C-1523 or DMSO for 4 days. Following treatment, cells were transferred to poly-L-lysine-coated coverslips, allowed time to attach, and then fixed, permeabilized, and mounted onto slides as for immunofluorescence. Random fields of cells were imaged for each sample and 500 cells were counted.

RT-PCR analysis. Total protein preparation, primers, cycling parameters were all performed as described previously (Lamont et al., 2013)

RNASeq Analysis. The raw sequencing data was filtered using NGSQCToolkit™ (v2.3, IlluQC_PRLL.pl and TrimmingReads.pl). The filtered and trimmed reads were then aligned to mm10 using tophat (v2.0.7). The aligned bam file was then passed through Cufflinks (v2.0.2) and reads per gene are counted using htseq-count. edgeR. Four RNA Seq differential gene expression comparisons, namely FC1, FC2, FC3 and FC4, were performed using the R/edgeR package (Robinson et al., 2010). FC1 tests for differences among WT-Vehicle and WT-C-1523, FC2 tests for differences among AID−/−-Vehicle and AID−/−-C1523, FC3 tests for differences among WT-C-1523 and AID−/−-C1523, and FC4 tests for differences among WT-Vehicle and AID−/−-Vehicle. Normalization was performed by trimmed mean of M values (TMM) per comparison. A multiple testing adjusted FDR of <0.05, was used to determine genes that were significantly differentially expressed.

Ingenuity Pathway Analysis. Ingenuity pathway analysis software (IPA; Ingenuity Systems, www.ingenuity.com, March 2014 release) was used for network generation across the different differentially expressed genes. These data sets were derived from differential gene expression analyses of treatment groups as outlined in FIG. 17A. Specifically, four sets were generated with genes significantly differentially expressing and unique to FC1, genes significantly differentially expression and unique to FC2, genes with greater fold-change in FC1 compared to FC2 but with FDR >0.05 and <0.10, and genes with greater fold-change in FC2 compared to FC1 but with FDR >0.05 and <0.10. Each of these data sets were uploaded to IPA and mapped to mouse Entrez gene symbols using the IPA knowledge base. These objects were overlaid onto a canonical pathways developed from information contained in the IPA Knowledge Base (March 2014 release).

REFERENCES

Boss, D. S., J. H. Beijnen, and J. H. M. Schellens. 2010. Inducing Synthetic Lethality using PARP Inhibitors. Curr Clin Pharmacol. 5:192-195.

Caddle, L. B., M. G. Hasham, W. H. Schott, B.-J. Shirley, and K. D. Mills. 2008. Homologous Recombination Is Necessary for Normal Lymphocyte Development. Mol. Cell. Biol. 28:2295-2303.

Calabrese, E. J. 2013. Hormetic mechanisms. Critical Reviews in Toxicology. 43:580-606.

Chahwan, R., W. Edelmann, M. D. Scharff, and S. Roa. 2012. AIDing antibody diversity by error-prone mismatch repair. Seminars in Immunology. 24:293-300.

Chaudhuri, J., M. Tian, C. Khuong, K. Chua, E. Pinaud, and F. W. Alt. 2003. Transcription-targeted DNA deamination by the AID antibody diversification enzyme. Nature. 422:726-730.

Cheson, B. D., D. A. Vena, J. Barrett, and B. Freidlin. 1999. Second Malignancies as a Consequence of Nucleoside Analog Therapy for Chronic Lymphoid Leukemias. Journal of Clinical Oncology. 17:2454.

Curry, C. L., L. L. Reed, E. Broude, T. E. Golde, L. Miele, and K. E. Foreman. 2007. Notch inhibition in Kaposi's sarcoma tumor cells leads to mitotic catastrophe through nuclear factor-RĨ~ signaling Molecular Cancer Therapeutics. 6:1983-1992.

Daboussi, F., A. Dumay, F. Delacoe, and B. S. Lopez. 2002. DNA double-strand break repair signalling: The casse of RAD51 post-translational regulation. Cellular Signalling. 14:969-975.

Foley, G. E., H. Lazarus, S. Farber, B. G. Uzman, and R. A. Adams. 1968. Studies on Human Leukemic Cels in Vitro. In The Proliferation and Spread of Neoplastic Cels. The Wiliams & Wilkins Co, Baltimore. 65-97.

Harper, J. W., and S. J. Elledge. 2007. The DNA Damage Response: Ten Years After. Molecular Cell. 28:739-745.

Hasham, M., K. Snow, N. Donghia, J. Branca, M. Lessard, J. Stavnezer, L. Shopland, and K. Mills. 2012. Activation-Induced cytidine deaminase-initiated off-target DNA breaks are detected and resolved during S phase. J Immunol. 189:2374-2382.

Hasham, M. G., N. M. Donghia, E. Coffey, J. Maynard, K. J. Snow, J. Ames, R. Y. Wilpan, Y. He, B. L. King, and K. D. Mills. 2010. Widespread genomic breaks generated by activation-induced cytidine deaminase are prevented by homologous recombination. Nat Immunol. 11:820-826.

Heintel, D., E. Kroemer, D. Kienle, I. Schwarzinger, A. Gleib, J. Schwarzmeier, R. Marculescu, T. Le, C. Mannhalter, A. Gaiger, S. Stilgenbauer, H. Dohner, C. Fonatsch, and U. Jager. 2004. High expression of activation-induced cytidine deaminase (AID) mRNA is associated with unmutated IGVH gene status and unfavourable cytogenetic aberrations in patients with chronic lymphocytic leukaemia. Leukemia. 18:756-762.

Hung, J.-Y., C.-W. Wen, Y.-L. Hsu, E.-S. Lin, M.-S. Huang, C.-Y. Chen, and P.-L. Kuo. 2013. Subamolide A Induces Mitotic Catastrophe Accompanied by Apoptosis in Human Lung Cancer Cells. Evidence-Based Complementary and Alternative Medicine. 2013:15.

Ishida, T., Y. Takizawa, T. Kainuma, J. Inoue, T. Mikawa, T. Shibata, H. Suzuki, S. Tashiro, and H. Kurumizaka. 2009. DIDS, a chemical compound that inhibits RAD51-mediated homologous pairing and strand exchange. Nucleic Acids Research. 37:3367-3376.

Kawabata, M., T. Kawabata, and M. Nishibori. 2005. Role of recA/RAD51 Family Proteins in Mammals. Acta Med Okayama. 59:1-9.

Klemm, L., C. Duy, I. Iacobucci, S. Kuchen, G. von Levetzow, N. Feldhahn, N. Henke, Z. Li, T. K.

Hoffmann, Y.-m. Kim, W.-K. Hofmann, H. Jumaa, J. Groffen, N. Heisterkamp, G. Martinelli, M. R.

Lieber, R. Casellas, and M. Muschen. 2009. The B Cell Mutator AID Promotes B Lymphoid Blast Crisis and Drug Resistance in Chronic Myeloid Leukemia. Cancer Cell. 16:232-245.

Kou, T., H. Marusawa, K. Kinoshita, Y. Endo, I.-m. Okazaki, Y. Ueda, Y. Kodama, H. Haga, I. Ikai, and T. Chiba. 2007. Expression of activation-induced cytidine deaminase in human hepatocytes during hepatocarcinogenesis. International Journal of Cancer. 120:469-476.

Krishna, G., J. Petrere, J. Anderson, and J. Theiss. 1995. Use of cyclophosphamide as a positive control in dominant lethal and micronucleus assays. Mutation Research/Environmental Mutagenesis and Related Subjects. 335:331-337.

Lamont, K. R., M. G. Hasham, N. M. Donghia, J. Branca, M. Chavaree, B. Ch ase, A. Breggia, J. Hedlund, I. Emery, F. Cavallo, M. Jasin, J. R ase, A. Breggia, J. Hedlund, I. Emery, F. Cavallo, M. Jasin, J. R$\sqrt{°}$ter, and K. D. Mills. 2013. Attenuating homologous recombination stimulates an AID-induced antileukemic effect. The Journal of Experimental Medicine. 210:1021-1033.

Latt, S., and R. Schreck. 1980. Sister Chromatid Exchange Analysis. Am J Hum Genet. 32:297-313.

Liu, Z., X. Wu, Y. Duan, Y. wang, B. Shan, J. Kong, X. Ma, and Y. Bao. 2011. AID expression is correlated with Bcr-Abl expression in CML-LBC and can be downregulated by As2O3 and/or imatinib. Leukemia Research. 35:1355-1359.

Londono-Vallejo, J. A., H. Der-Sarkissian, L. Cazes, S. Bacchetti, and R. R. Reddel. 2004. Alternative Lengthening of Telomeres Is Characterized by High Rates of Telomeric Exchange. Cancer Research. 64:2324-2327.

McBride, K. M., A. Gazumyan, E. M. Woo, V. M. Barreto, D. F. Robbiani, B. T. Chait, and M. C.

Nussenzweig. 2006. Regulation of hypermutation by activation-induced cytidine deaminase phosphorylation. Proceedings of the National Academy of Sciences. 103:8798-8803.

Molica, S. 2005. Second neoplasms in chronic lymphocytic leukemia: incidence and pathogenesis with emphasis on the role of different therapies. Leukemia & Lymphoma. 46:49-54.

Moynahan, M., A. Pierce, and M. Jasin. 2001. BRCA2 is required for homology-directed repair of chromosomal breaks. Molecular Cell. 7:263-272.

Muramatsu, M., K. Kinoshita, S. Fagarasan, S. Yamada, Y. Shinkai, and T. Honjo. 2000. Class Switch Recombination and Hypermutation Require Activation-Induced Cytidine Deaminase (AID), a Potential RNA Editing Enzyme. Cell. 102:553-563.

Nagaoka, H., T. H. Tran, M. Kobayashi, M. Aida, and T. Honjo. 2010. Preventing AID, a physiological mutator, from deleterious activation: regulation of the genomic instability that is associated with antibody diversity. International Immunology. 22:227-235.

Nakanishi, K., Y. Yang, A. Pierce, T. Taniguchi, M. Digweed, A. D'Andrea, Z. Wang, and M. Jasin. 2005. Human Fanconi anemia monoubiquitination pathway promotes homologous DNA repair. Proceedings of the National Academy of Sciences. 102:1110-1115.

Okazaki, I.-m., H. Hiai, N. Kakazu, S. Yamada, M. Muramatsu, K. Kinoshita, and T. Honjo. 2003. Constitutive Expression of AID Leads to Tumorigenesis. The Journal of Experimental Medicine. 197:1173-1181.

Palacios, F., P. Moreno, P. Morande, C. Abreu, A. n. Correa, V. Porro, A. I.

Landoni, R. Gabus, M. Giordano, G. Dighiero, O. Pritsch, and P. Oppezzo. 2010. High expression of AID and active class switch recombination might account for a more aggressive disease in unmutated CLL patients: link with an activated microenvironment in CLL disease. Blood. 115:4488¬4496.

Pasqualucci, L., G. Bhagat, M. Jankovic, M. Compagno, P. Smith, M. Muramatsu, T. Honjo, H. C. Morse, M. C. Nussenzweig, and R. Dalla-Favera. 2008. AID is required for germinal center-derived lymphomagenesis. Nat Genet. 40:108-112.

Robak, E., and T. Robak. 2007. Skin lesions in chronic lymphocytic leukemia. Leukemia & Lymphoma. 48:855-865.

Robbiani, D. F., S. Bunting, N. Feldhahn, A. Bothmer, J. Camps, S. Deroubaix, K. M. McBride, I. A. Klein, G. Stone, T. R. Eisenreich, T. Ried, A. Nussenzweig, and M. C. Nussenzweig. 2009. AID Produces DNA Double-Strand Breaks in Non-Ig Genes and Mature B Cell Lymphomas with Reciprocal Chromosome Translocations. Molecular Cell. 36:631-641.

Robinson, M. D., D. J. McCarthy, and G. K. Smyth. 2010. edgeR: a Bioconductor package for differential expression analysis of digital gene expression data. Bioinformatics. 26:139-140.

Roninson, I. B., E. V. Broude, and B.-D. Chang. 2001a. If not apoptosis, then what? Treatment-induced senescence and mitotic catastrophe in tumor cells. Drug Resistance Updates. 4:303-313.

Roninson, I. B., B.-D. Chang, and E. V. Broude. 200 lb. Non-Apoptotic Responses to Anticancer Agents: Mitotic Catastrophe, Senescence, and the Role of p53 and p21. In Cell Cycle Ceckpoints and Cancer. M.v. Blagosklonny, editor. Landes Bioscience, Georgetown, Tex.

Shimizu, T., H. Marusawa, Y. Endo, and T. Chiba. 2012. Inflammation-mediated genomic instability: roles of activation-induced cytidine deaminase in carcinogenesis. Cancer Science. 103:1201-1206.

Shinmura, K., H. Igarashi, M. Goto, H. Tao, H. Yamada, S. Matsuura, M. Tajima, T. Matsuda, A. Yamane, and K.e.a. Funai. 2011. Aberrant expression and mutation-inducing activity of AID in human lung cancer. Annals of Surgical Oncology. 18:2084-2092.

Shinohara, A., H. Ogawa, and T. Ogawa. 1992. Rad51 protein involved in repair and recombination in S. cerevisiae is a RecA-like protein. Cell. 69:457¬470.

Stacchini, A., M. Aragno, A. Vallario, A. Alfarano, P. Circosta, D. Gottardi, A. Faldella, G. Rege-Cambrin, U. Thunberg, K. Nilsson, and F. Caligaris-Cappio. 1999. MEC1 and MEC2: two new cell lines derived from B-chronic lymphocytic leukaemia in prolymphocytoid transformation. Leukemia Research. 23:127-136.

Staszewski, O., R. E. Baker, A. J. Ucher, R. Martier, J. Stavnezer, and J. E. J. Guikema. 2011. Activation-Induced Cytidine Deaminase Induces Reproducible DNA Breaks at Many Non-Ig Loci in Activated B Cells. Molecular Cell. 41:232-242.

Stults, D., M. Killen, and A. Pierce. 2014. The Sister Chromatid Exchange (SCE) Assay. In Molecular Toxicology Protocols. Vol. 1105. P. Keohavong and S. G. Grant, editors. Humana Press. 439-455.

Sung, P., and D. L. Robberson. 1995. DNA strand exchange mediated by a RAD51-ssDNA nucleoprotein filament with polarity opposite to that of RecA. Cell. 82:453-461.

Suwaki, N., K. Klare, and M. Tarsounas. 2011. RAD51 paralogs: Roles in DNA damage signalling, recombinational repair and tumorigenesis. Seminars in Cell & Developmental Biology. 22:898-905.

Thacker, J. 2005. The RAD51 gene family, genetic instability and cancer. Cancer Letters. 219:125-135.

Zan, H., and P. Casali. 2008. AID- and Ung-dependent generation of staggered double-strand DNA breaks in immunoglobulin class switch DNA recombination: A post-cleavage role for AID. Molecular Immunology. 46:45-61.

Example 3

Genetic chemotherapy uses the immune system's natural genetic programming as an "Achilles heel" in cancer, inducing an overwhelming imbalance between DNA damage versus repair. This imbalance kills cancer cells, but preserves healthy cells, resulting in a remarkable absence of the kinds of side effects caused by traditional chemotherapy.

Described herein is a genetic chemotherapy compound—C-1523—that is 1000-times more effective than DIDS, with no increased acute side effects and C-1523-1a, which is more potent and effective and has improved pharmacokinetic properties. Additionally, it is demonstrated herein that genetic chemotherapy can be applicable to an even broader range of cancers, beyond leukemia and lymphoma, including breast, ovarian and lung.

The effects of C-1523 have been tested in vitro in cultured cancer cells and in vivo with human cell samples. Preclinical pharmacokinetic analyses were conducted to determine the fate of the compound as it is administered. These studies showed that C-1523-1a is remarkably potent and extraordinarily effective in targeting AID-expressing cells, the cells responsible for genetic chemotherapy. Furthermore, C-1523-1a shows significantly improved pharmacokinetic properties (e.g. plasma half-life of ~6 hours at 20 mg/kg dosing) and successfully reduced tumors in a non-Hodgkin's lymphoma model.

Both C-1523 and C-1523-1a cause almost no acute toxicity, demonstrating that these drugs are highly effective against some types of cancers, and also have a safety profile that is superior to most existing chemotherapies. Both single and multiple dose toxicity studies in mice and rats (the preferred preclinical rodent species) demonstrated excellent tolerance to prolonged drug exposure with some B-cell reduction being the only (and predicted) side effect. This indicates that genetic chemotherapy as described herein has little to no side effects but is enormously effective at causing a patient's cancer to self-destruct in a variety of cancer types.

C-1523-1a is demonstrated herein to be readily administered as an injectable treatment.

Example 4

Figure 19A:
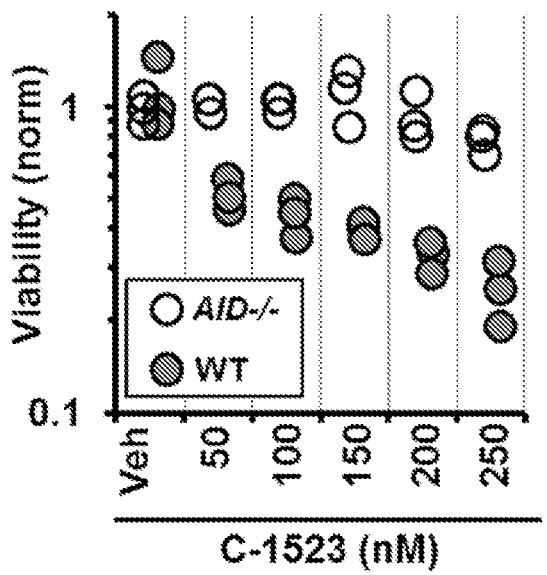
FIG. 19A depicts a graph of dose response data showing a dose dependent reduction in B-cell viability in AID-expressing B-cells exposed to C-1523, but not in AID-negative B-cells. Cells were treated in culture for 3 days with vehicle (DMSO) or 50, 100, 150, 200, or 250 nM C-1523 and viability was scored by Trypan blue exclusion and manual cytometry.
Figure 19B:
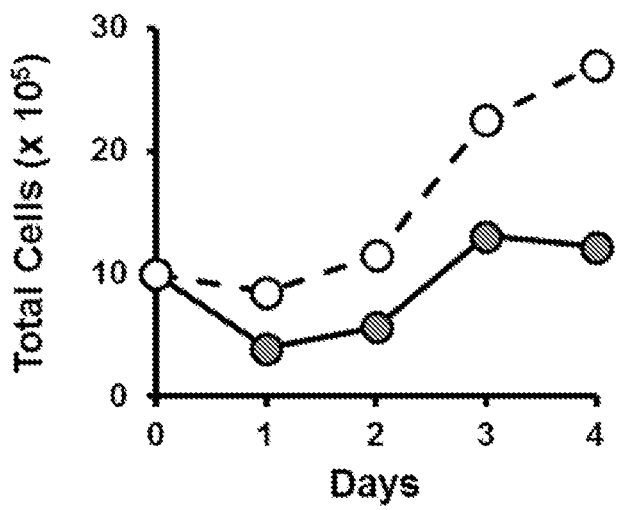
FIG. 19B depicts a graph of growth curves for AID-expressing (filled) and AID-negative (open) B-cells treated with 100 nM C-1523 for the indicated number of days. Viability was determined following staining with Trypan blue.

There is a dose-dependent reduction in B-cell viability in AID-expressing B-cells exposed to C-1523, but not in AID-negative B-cells (FIG. 19A). Cells were treated in culture for 3 days with vehicle (DMSO) or 50, 100, 150, 200, or 250 nM C-1523 and viability was scored by Trypan blue exclusion and manual cytometry. Viability was determined following staining with Trypan blue (FIG. 19B).

Figure 20:
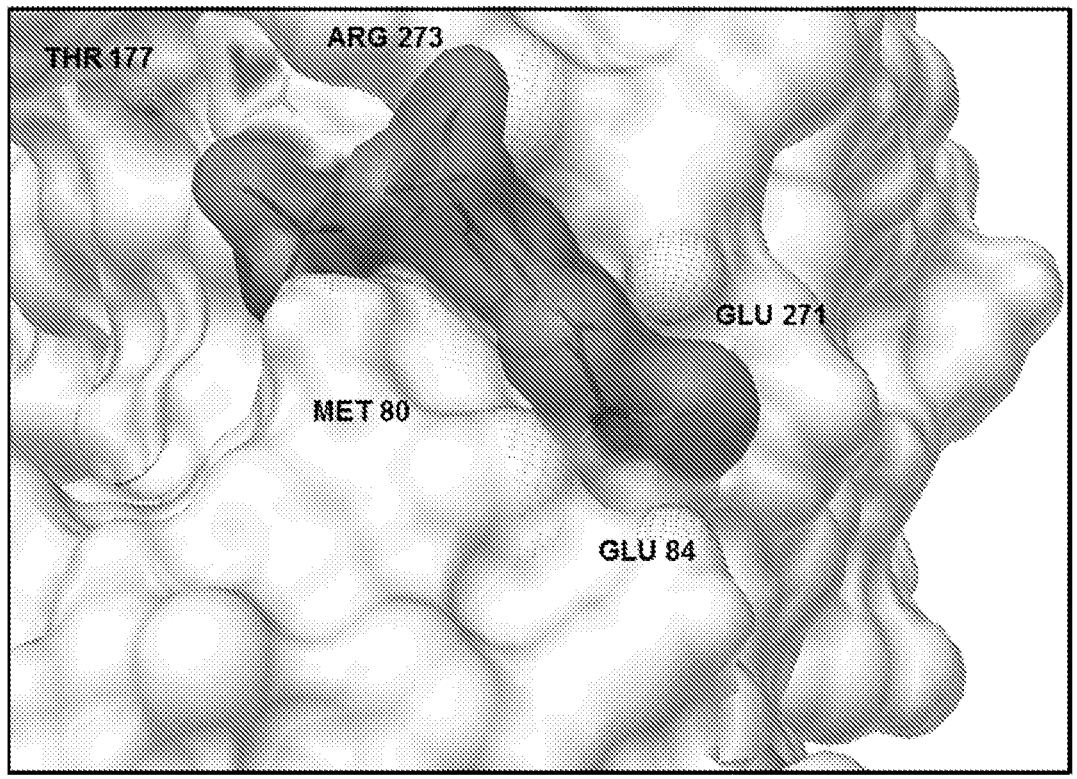
FIG. 20 depicts structural modeling showing C-1523 binding to a surface pocket of RAD51. Predicted amino acid contacts or affected amino acids include MET80, GLU84 THR177, GLU271, and ARG273.

C-1523 binds to a surface pocket of RAD51 and is predicted to contact or affect amino acids including MET80, GLU84 THR177, GLU271, and ARG273 (FIG. 20).

Figure 21:
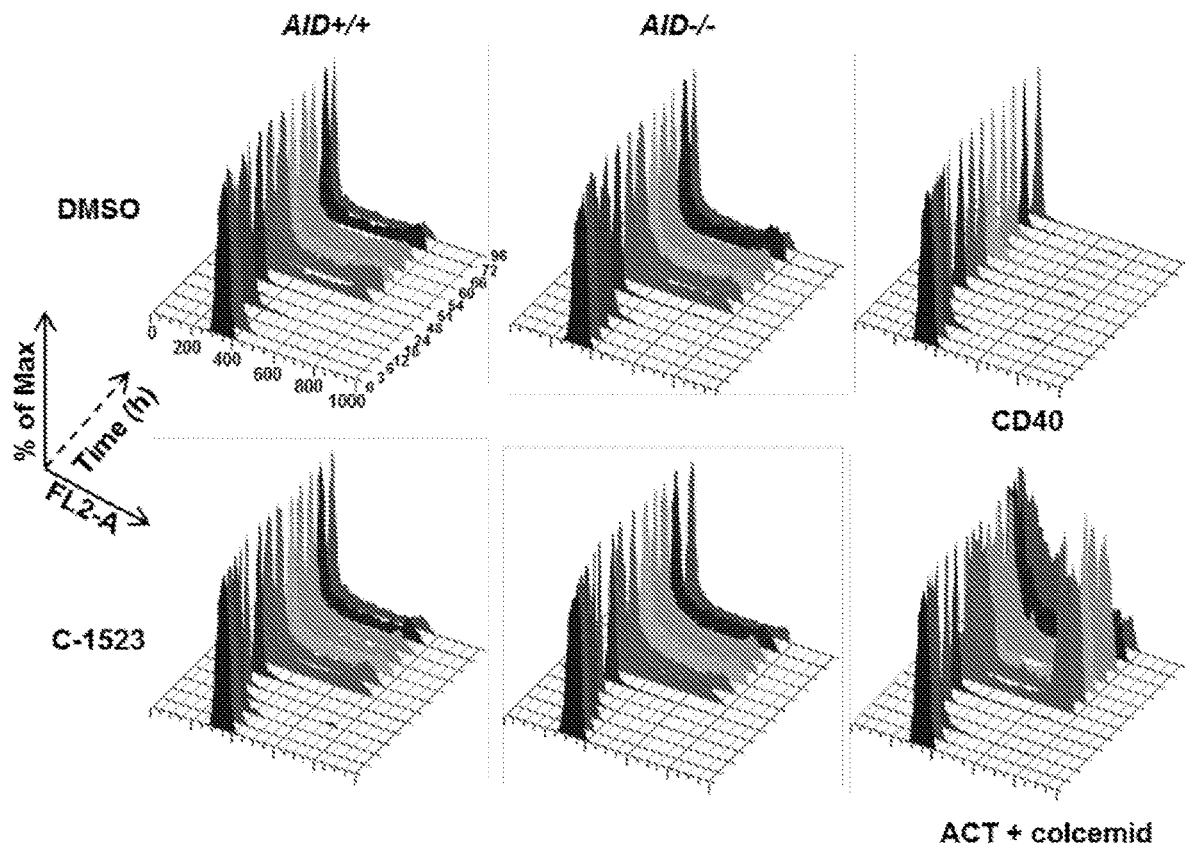
FIG. 21 depicts cell cycle analysis showing minimal differences in vehicle versus C-1523 treated B-cells. AID+/+ or AID−/− B-cells were cultured with 100 nM and cell cycle profiles were determined by propidium iodide staining and flow cyotmetry at intervals up to 96 hours. Non-activated (CD40) cells were used as a negative control; activated cells treated with the microtuble poison colcemid (ACT+colcemid) were used as a positive control.
Figure 22:
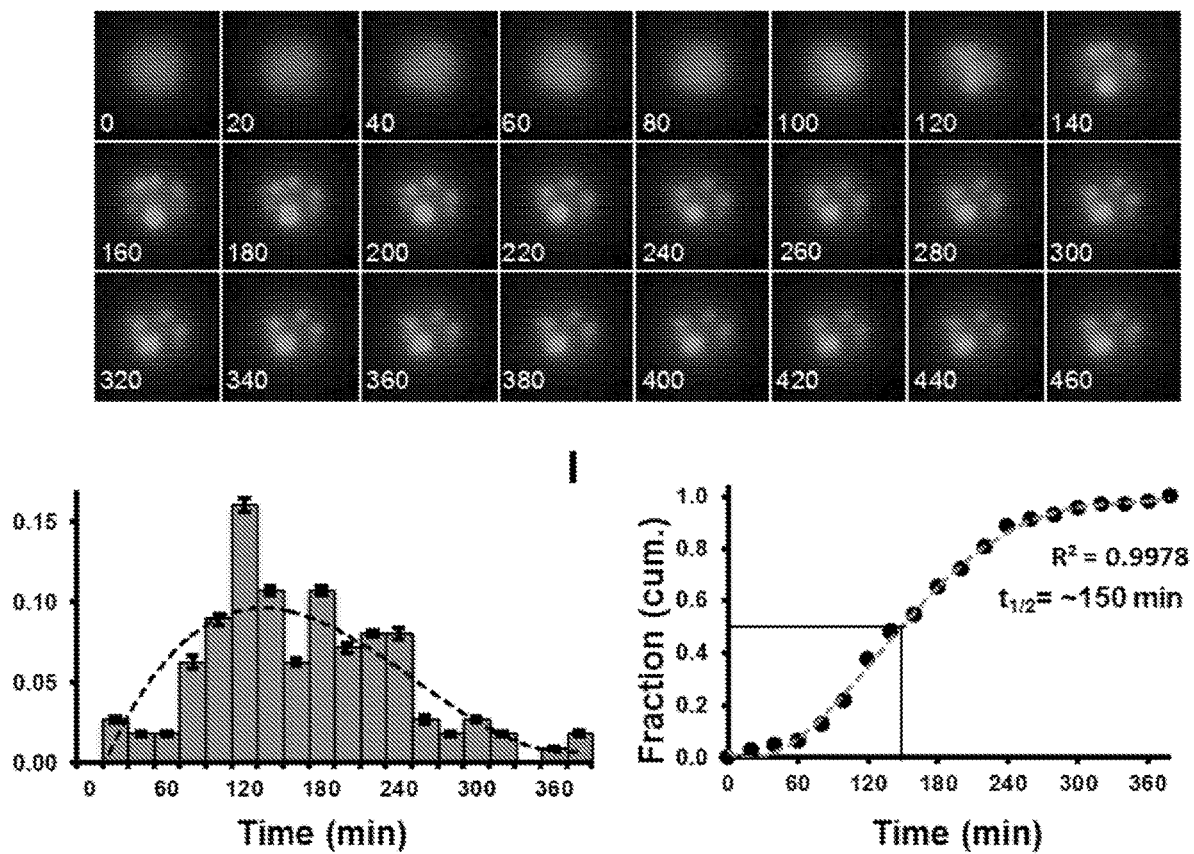
FIG. 22 depicts live cell imaging of primary, AID expressing B-cells treated with 100 nM C-1523. Histone H2B-EGFP transgenic mice were used as a source of B-cells to facilitate imaging of chromatin. The top panel depicts an individual cell imaged at 20 minute intervals for 460 minutes. Images show chromosomal fragmentation commencing at 120 minutes. Data in the bottom panels depict quantification of live cell imaging depicting the fraction of cells that commence fragmentation at each time point (bottom left panel) and the cumulative fraction of fragmented nuclei (bottom right panel).

C-1523 has a minimal effect on cell cycle (FIG. 21). AID+/+ or AID-/- B-cells were cultured with 100 nM and cell cycle profiles were determined by propidium iodide staining and flow cyotmetry at intervals up to 96 hours. Non-activated (CD40) cells were used as a negative control; activated cells treated with the microtuble poison colcemid (ACT+colcemid) were used as a positive control. Nuclei fragmentation analysis of primary, AID expressing B-cells treated with 100 nM C-1523 was conducted (FIG. 22).

Figure 23:
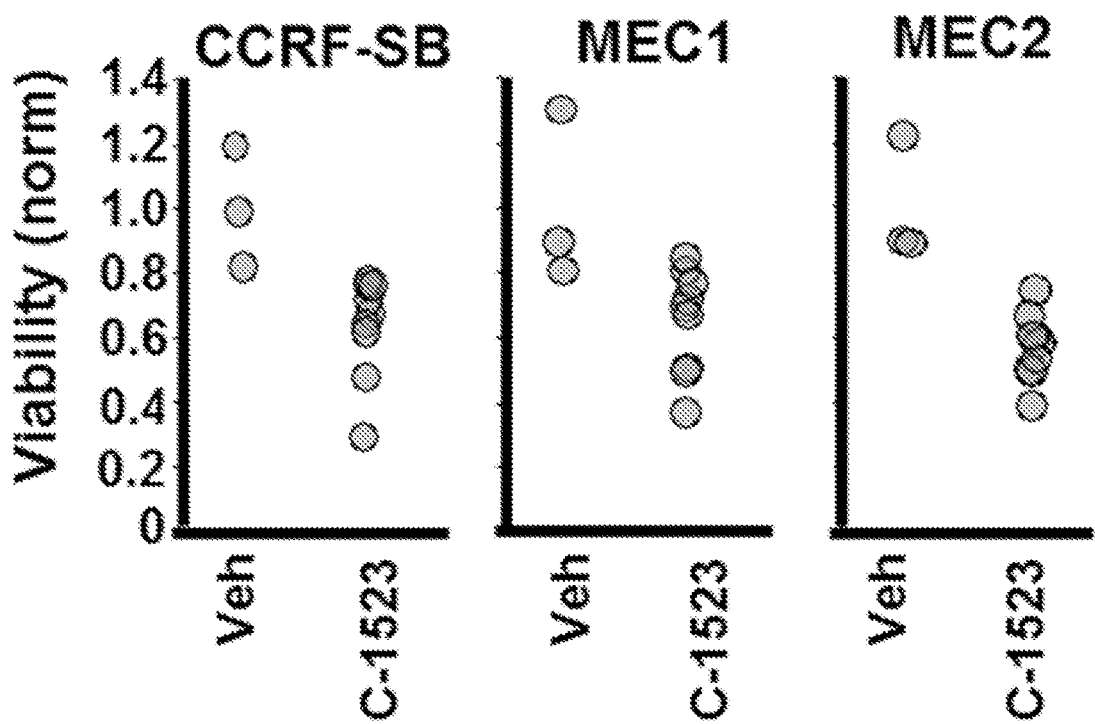
FIG. 23 depicts graphs of viability analysis for human cancer cell lines treated with C-1523. The acute lymphoblastic leukemia (ALL) line CCRF-SB and the chronic lymphocytic leukemia lines MEC1 and MEC2 were treated with vehicle (DMSO) or 100 nM C-1523, and viability was measured by Tyrpan blue exclusion. All three lines express AID and are sensitive to C-1523 treatment.
Figure 24:
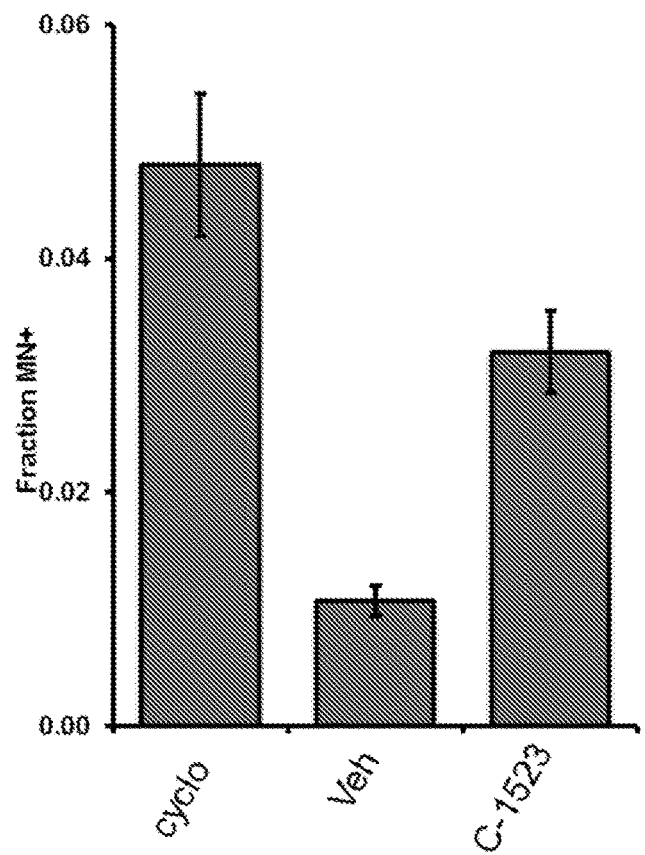
FIG. 24 depicts a graph of the fraction of MEC1 cells showing micronuclei, as evidence of mitotic catastrophe, following treatment with cyclophosphamide (positive control), vehicle (DMSO), or C-1523 (100 nM).

The acute lymphoblastic leukemia (ALL) line CCRF-SB and the chronic lymphocytic leukemia lines MEC1 and MEC2 are sensitive to C-1523 treatment (FIG. 23). MEC1 cells were analyzed for micronuclei levels after C-1523 treatment (FIG. 24).

Figure 25:
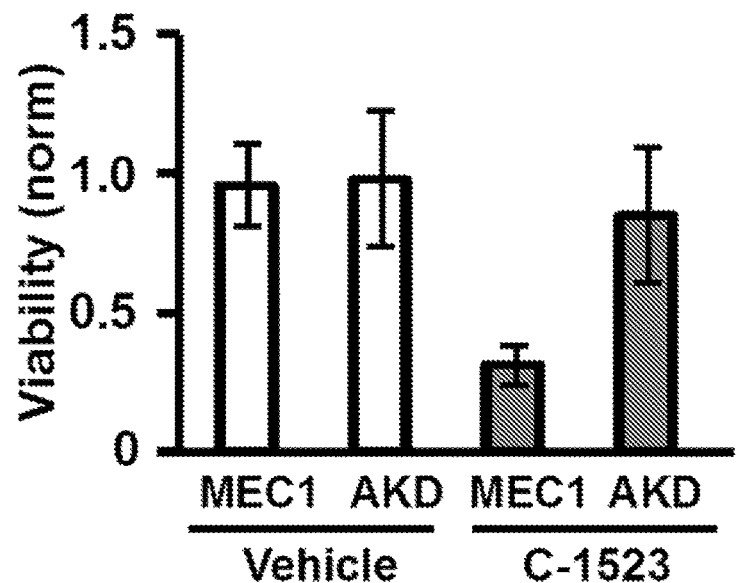
FIG. 25 depicts a graph of the comparative viability of MEC1 versus the isogenic AID-knockdown cell line AKD, treated with vehicle (DMSO) or 100 nM C-1523. MEC1 cells, but not AKD cells, are sensitive to C-1523.
Figure 26:
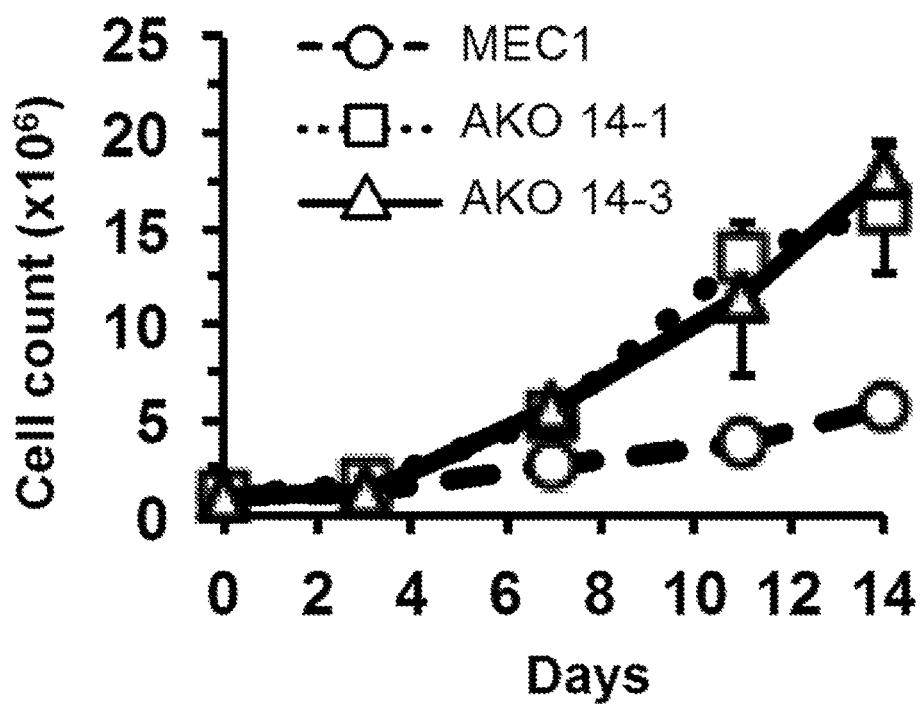
FIG. 26 depicts a graph of the comparative viability of MEC1 versus the isogenic AID-knockout cell lines AKO 14-1 and AKO 14-3, treated with vehicle (DMSO) or 100 nM C-1523. MEC1 cells, but not AKD cells, are sensitive to C-1523.

MEC1 cells, but not the isogenic AID-knockdown cell line AKD, are sensitive to C-1523 (FIG. 25). MEC1, but not the isogenic AID-knockout cell lines AKO 14-1 and AKO 14-3, are sensitive to C-1523 (FIG. 26).

Figure 27:
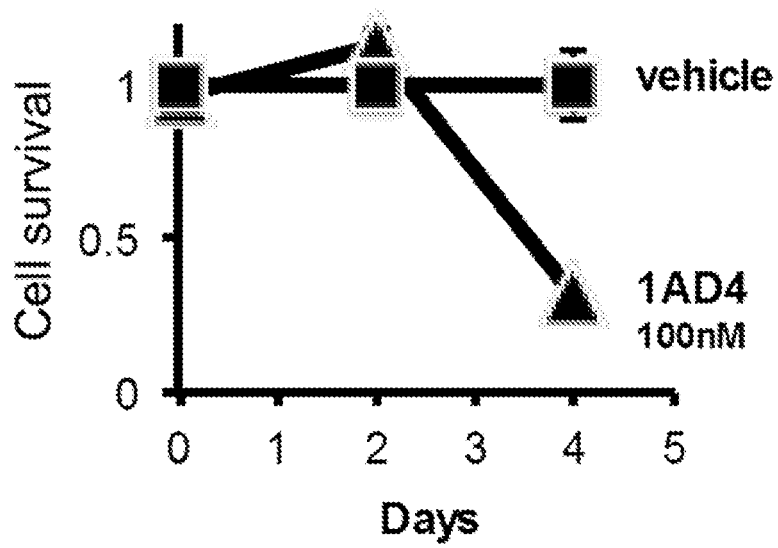
FIG. 27 depicts a graph of cell survival analysis of primary AID-expressing B-cells treated with C-1523-1AD4 (100 nM) versus vehicle (DMSO).

Primary AID-expressing B-cells were sensitive to C-1523-1AD4 (FIG. 27).

What is claimed is:
1. A compound of Formula I

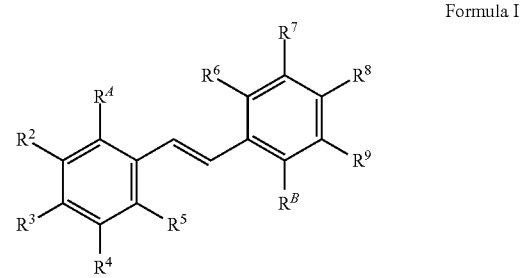

Formula I wherein:
(i)
one of $R^3$ and $R^8$ is $NHC(O)CH_3$ and the other is $NHC(S)NHCH(CH_3)_2$;

$R^A$ and $R^B$ are $SO_2N(R^{22})_2$, or one of $R^A$ and $R^B$ is $SO_3R^{23}$ and the other is hydrogen or $SO_3R^{23}$, or one of $R^A$ and $R^B$ is $SO_3^-Y^+$ and the other is hydrogen, or one of $R^A$ and $R^B$ is $CO_2^-Y^+$ and the other is hydrogen or $CO_2^-Y^+$, or one of $R^A$ and $R^B$ is $P(O)(O^-)_2(Y^+)_2$ and the other is hydrogen or $P(O)(O^-)_2(Y^+)_2$;

$R^2$, $R^4$, $R^5$, $R^6$, $R^7$ and $R^9$ are independently hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl;

$R^{21}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl;

$R^{22}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl or $C(O)(CH_2)_nCH_3$ wherein n=0, 1, 2, 3, 4, 5, or 6, or the two $R^{22}$ together with the nitrogen they are attached to form an optionally substituted 3-8 membered heterocyclyl;

$R^{23}$ is independently for each occurrence optionally substituted linear or branched $C_1$-$C_{10}$ alkyl, or cyclopropyl;

$Y^+$ is for each occurrence a cation; and pharmaceutically acceptable salts thereof;

or (ii) $R^3$ and $R^8$ are $NHC(O)CH_3$;

$R^A$ and $R^B$ are $SO_2N(R^{24})(R^{25})$, or one of $R^A$ and $R^B$ is $SO_3R^{23}$ and the other is hydrogen or $SO_3R^{23}$, or one of $R^A$ and $R^B$ is $SO_3^-Y^+$ and the other is hydrogen, or one of $R^A$ and $R^B$ is $CO_2^-Y^+$ and the other is hydrogen or $CO_2^-Y^+$, or one of $R^A$ and $R^B$ is $P(O)(O^-)_2(Y^+)_2$ and the other is hydrogen or $P(O)(O^-)_2(Y^+)_2$;

$R^2$, $R^4$, $R^5$, $R^6$, $R^7$ and $R^9$ are independently hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl;

$R^{21}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, or optionally substituted heteroaryl;

$R^{22}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted heteroaryl or $C(O)(CH_2)_nCH_3$ wherein n=0, 1, 2, 3, 4, 5, or 6, or the two $R^{22}$ together with the nitrogen they are attached to form an optionally substituted 3-8 membered heterocyclyl;

$R^{23}$ is independently for each occurrence optionally substituted linear or branched $C_1$-$C_{10}$ alkyl, or cyclopropyl;

$R^{24}$ is independently for each occurrence hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted heteroaryl or $C(O)(CH_2)_nCH_3$ wherein n=0,1,2,3,4,5, or 6;

$R^{25}$ is independently for each occurrence hydrogen, or $R^{24}$ and $R^{25}$ together with the nitrogen they are attached to form an optionally substituted 3-8 membered heterocyclyl;

$Y^+$ is for each occurrence a cation; and pharmaceutically acceptable salts thereof.

2. The compound of claim 1, wherein at least one of $R^2$, $R^4$, $R^5$, $R^6$, $R^7$, and $R^9$ is hydrogen.

3. The compound of claim 1, wherein $R^2$, $R^4$, $R^5$, $R^6$, $R^7$, and $R^9$ all are hydrogen.

4. The compound of claim 1, wherein $R^{22}$ is selected independently for each occurrence from the group consisting of hydrogen, methyl, ethyl, propyl, isopropyl, butyl, isobutyl, pentyl, t-butyl, and cyclopropyl; or the two $R^{22}$ together with the nitrogen they are attached to form an optionally substituted 3-8 membered heterocyclyl.

5. The compound of claim 1, wherein $R^{23}$ is independently for each occurrence from the group consisting of methyl, ethyl, propyl, isopropyl, butyl, isobutyl, pentyl, t-butyl, or cyclopropyl.

6. The compound of claim 1, wherein $Y^+$ is selected independently for each occurrence from the group consisting of sodium, potassium, lithium, ammonium, and any combinations thereof.

7. The compound of claim 1, wherein $R^A$ is $SO_3R^{23}$; $R^B$ is hydrogen or $SO_3R^{23}$; each $R^{23}$ is independently isopropyl or t-butyl; and $R^2$, $R^4$, $R^5$, $R^6$, $R^7$, and $R^9$ are hydrogen.

8. The compound of claim 1, wherein one of $R^A$ and $R^B$ is $SO_3^-Y^+$ and the other is hydrogen; one of $R^3$ and R is $NHC(O)CH_3$ and the other is $NHC(S)NHCH(CH_3)_2$; and $R^2$, $R^4$, $R^5$, $R^6$, $R^7$, and $R^9$ are hydrogen.

9. The compound of claim 1, wherein one of $R^A$ and $R^B$ is $CO_2^-Y^+$ and the other is hydrogen or $CO_2^-Y^+$; one of $R^3$ and $R^8$ is $NHC(O)CH_3$ and the other is $NHC(S)NHCH(CH_3)_2$; and $R^2$, $R^4$, $R^5$, $R^6$, $R^7$, and $R^9$ are hydrogen.

10. The compound of claim 1, wherein one of $R^A$ and $R^B$ is $P(O)(O^-)_2(Y^+)_2$ and the other is hydrogen or $P(O)(O^-)_2(Y^+)_2$; one of $R^3$ and R is $NHC(O)CH_3$ and the other is $NHC(S)NHCH(CH_3)_2$; and $R^2$, $R^4$, $R^5$, $R^6$, $R^7$, and $R^9$ are hydrogen.

11. A compound selected from the group consisting of

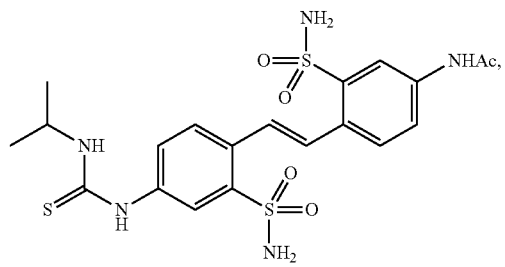

111
-continued
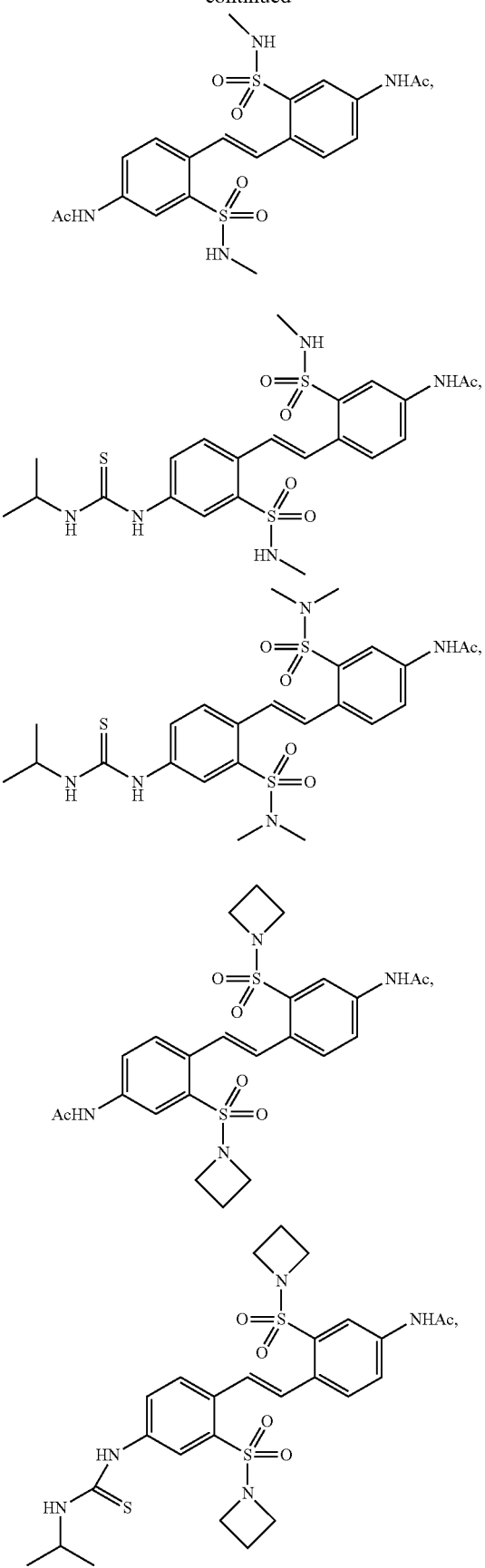
112
-continued
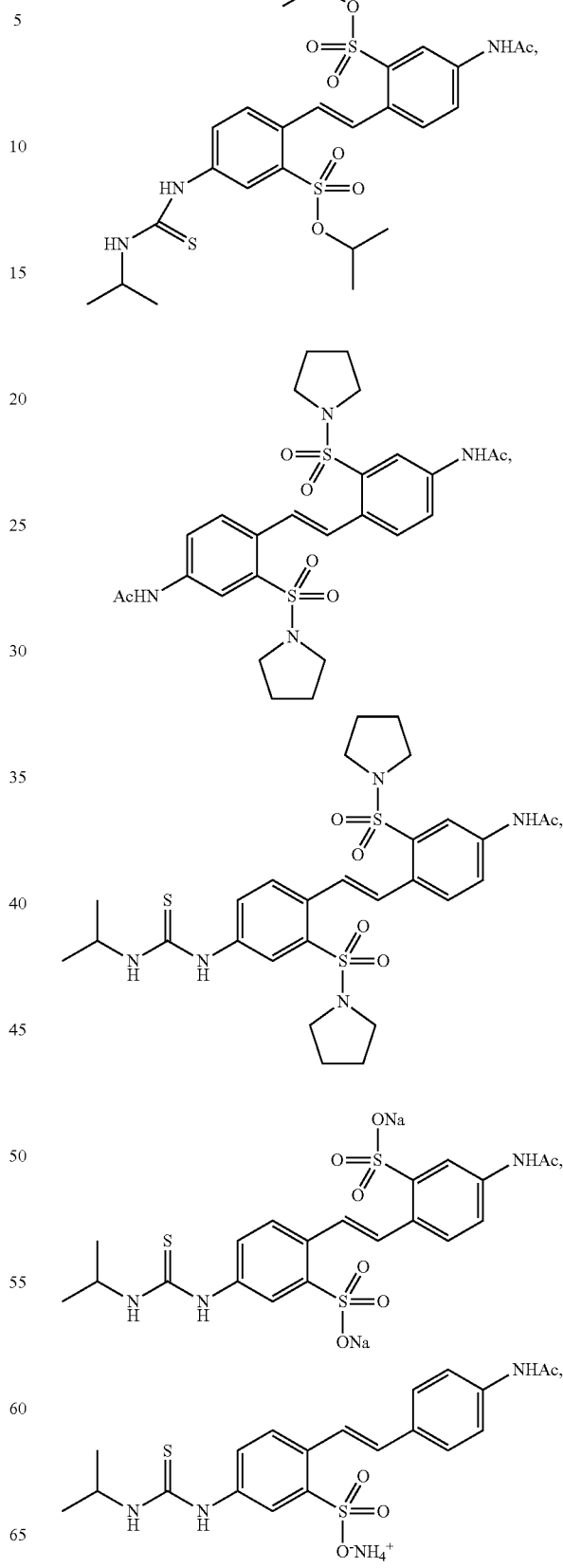

113
-continued

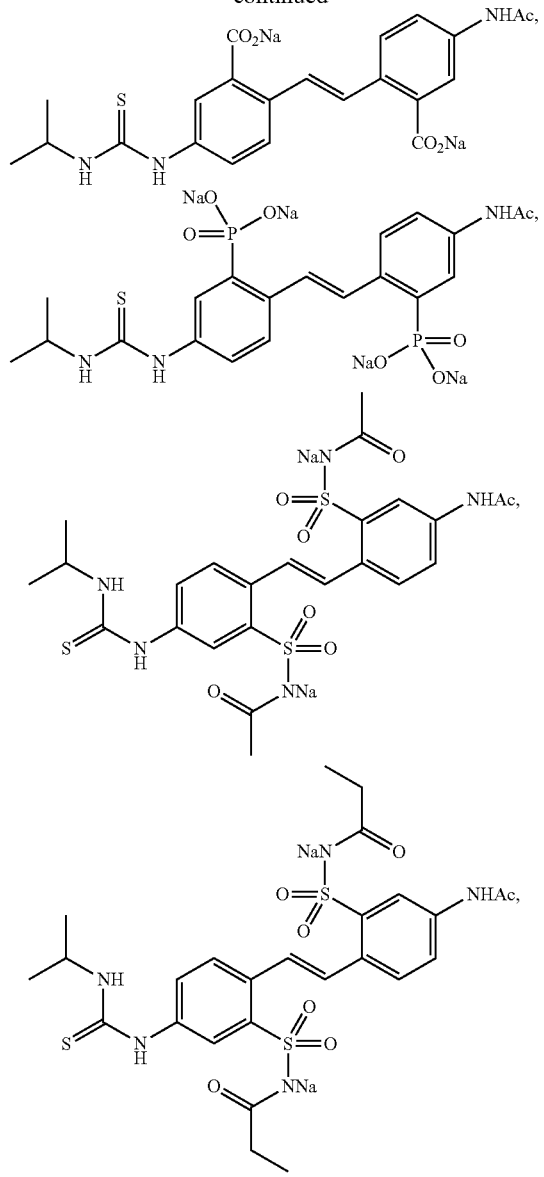

114
-continued

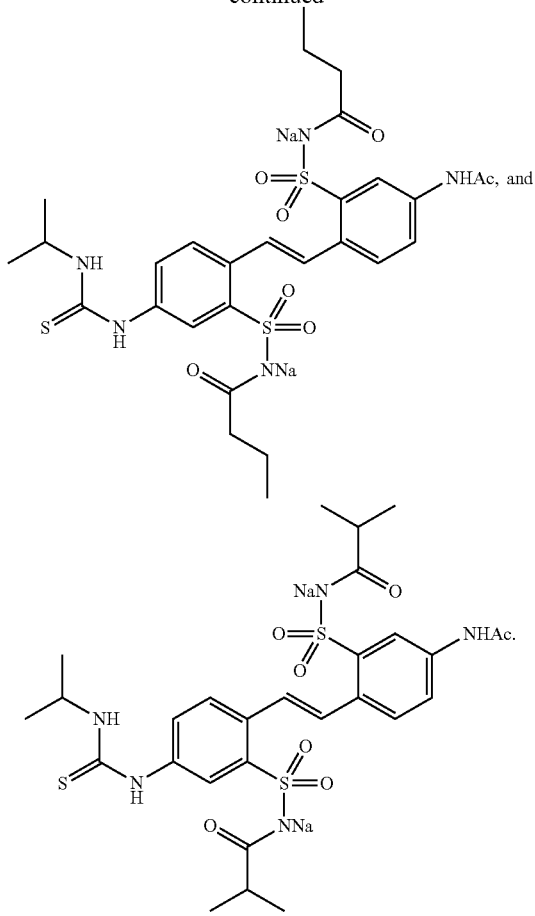

12. The compound of claim 1, where $R^A$ and $R^B$ are $SO_2N(R^{22})_2$.

13. The compound of claim 1, wherein one of $R^3$ and $R^8$ is $NHC(O)CH_3$ and the other is $NHC(S)NHCH(CH_3)_2$.

14. The compound of claim 1, wherein $R^3$ and $R$ are $NHC(O)CH_3$; $R^A$ and $R^B$ are $SO_2N(R^{24})(R^{25})$; and $R^{24}$ and $R^{25}$ together with the nitrogen they are attached to form an optionally substituted 3-8 membered heterocyclyl.

* * * * *